(12) United States Patent
Dai et al.

(10) Patent No.: US 9,823,246 B2
(45) Date of Patent: *Nov. 21, 2017

(54) FLUORESCENCE ENHANCING PLASMONIC NANOSCOPIC GOLD FILMS AND ASSAYS BASED THEREON

(71) Applicant: The Board of Trustees of the Leland Stanford Junior University, Palo Alto, CA (US)

(72) Inventors: Hongjie Dai, Cupertino, CA (US); Scott M. Tabakman, Palo Alto, CA (US); Guosong Hong, Stanford, CA (US); Bo Zhang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 850 days.

This patent is subject to a terminal disclaimer.

(21) Appl. No.: 13/728,798

(22) Filed: Dec. 27, 2012

(65) Prior Publication Data

US 2013/0172207 A1    Jul. 4, 2013

Related U.S. Application Data

(60) Provisional application No. 61/580,883, filed on Dec. 28, 2011.

(51) Int. Cl.
G01N 33/553 (2006.01)
G01N 21/65 (2006.01)

(52) U.S. Cl.
CPC ......... *G01N 33/553* (2013.01); *G01N 21/658* (2013.01); *G01N 2610/00* (2013.01); *Y10T 428/24851* (2015.01); *Y10T 428/24909* (2015.01); *Y10T 428/24917* (2015.01)

(58) Field of Classification Search
CPC .. G01N 33/553; G01N 21/64; G01N 21/6452; G01N 21/648
See application file for complete search history.

(56) References Cited

U.S. PATENT DOCUMENTS

| | | | |
|---|---|---|---|
| 4,816,567 A | 3/1989 | Cabilly et al. | |
| 5,510,270 A | 4/1996 | Fodor et al. | |
| 5,527,712 A * | 6/1996 | Sheehy ............... | G01N 33/533 422/552 |
| 5,556,752 A | 9/1996 | Lockhart et al. | |
| 5,578,832 A | 11/1996 | Trulson et al. | |
| 5,750,341 A | 5/1998 | MacEvicz | |
| 6,306,597 B1 | 10/2001 | MacEvicz | |
| 6,624,886 B2 | 9/2003 | Nathan et al. | |
| 6,755,953 B2 | 6/2004 | Baba | |
| 7,115,400 B1 | 10/2006 | Adessi et al. | |
| 7,179,659 B2 * | 2/2007 | Stolowitz et al. ........... | 436/525 |
| 7,211,390 B2 | 5/2007 | Rothberg et al. | |
| 7,232,656 B2 | 6/2007 | Balasubramanian et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,491,534 B2 | 2/2009 | Collas et al. | |
| 7,824,926 B1 | 11/2010 | Porter et al. | |
| 7,948,015 B2 | 5/2011 | Rothberg et al. | |
| 8,435,738 B2 | 5/2013 | Holmes | |
| 2002/0119118 A1 | 8/2002 | Fong et al. | |
| 2003/0013130 A1 | 1/2003 | Charych et al. | |
| 2003/0108726 A1 | 6/2003 | Schembri et al. | |
| 2003/0218744 A1 | 11/2003 | Shalaev et al. | |
| 2006/0021468 A1 | 2/2006 | Ah et al. | |
| 2007/0122413 A1 | 5/2007 | Sivakumar et al. | |
| 2007/0128189 A1 | 6/2007 | Sivakumar et al. | |
| 2007/0135335 A1 | 6/2007 | Collier et al. | |
| 2007/0141625 A1 | 6/2007 | Santos et al. | |
| 2007/0224638 A1 | 9/2007 | Melanitou-McClymont | |
| 2008/0160580 A1 | 7/2008 | Adessi et al. | |
| 2008/0194474 A1 | 8/2008 | Ildstad | |
| 2008/0198376 A1 * | 8/2008 | Poponin ............... | G01N 21/658 356/301 |

(Continued)

FOREIGN PATENT DOCUMENTS

WO    WO-2014160175 A1    10/2014

OTHER PUBLICATIONS

Leong et al 2010 Adv. Funct. Mater. 20: 2675-2682; epub Jul. 7, 2010.*
Wang et al. (Angew. Chem. Int. Ed. 2007, 46, 9040-9044).*
Gao et al. (Adv. Funct. Mater. 2010, 20, 78-86 ).*
Fu et al. (J. Am. Chem. Soc. 2010, 132, 5540-5541 published Apr. 5, 2010) and supplementary materials.*
Chen et al. (Nature biotechnology 26.11 (2008): 1285-1292).*
Dubertret et al. (Nature biotechnology 19.4 (2001): 365-370).*
Pazos-Perez et al. (Chem. Sci., 2010, 1, 174-178).*

(Continued)

*Primary Examiner* — Chris L Chin
(74) *Attorney, Agent, or Firm* — Brian E. Davy; Bozicevic, Field & Francis LLP

(57) ABSTRACT

Disclosed are nanostructured gold films which may be produced by solution-phase depositions of gold ions onto a variety of surfaces. The resulting plasmonic gold films are used for enhanced spectroscopic-based immunoassays in multiplexed microarray format with detection mechanisms based on either surface-enhanced Raman scattering or near-infrared fluorescence enhancement. The preparation of the films and subsequent modifications of the gold film surfaces afford increased sensitivity for various microarrays. The films are discontinuous, forming gold "islands." Sensitivity, size, shape, and density of the nanoscopic gold islands comprising the discontinuous nanostructured gold film are controlled to enhance the intensity of Raman scattering and fluorescence in the near-infrared, allowing for improved measurements in clinical diagnostic or biomedical research applications.

18 Claims, 18 Drawing Sheets

(56) References Cited

U.S. PATENT DOCUMENTS

| | | |
|---|---|---|
| 2008/0213280 A1 | 9/2008 | Benyunes |
| 2008/0220988 A1 | 9/2008 | Zhou |
| 2008/0221016 A1 | 9/2008 | Byrne et al. |
| 2008/0286795 A1 | 11/2008 | Kawashima et al. |
| 2009/0023166 A1 | 1/2009 | Jeannin et al. |
| 2009/0088329 A1 | 4/2009 | Brennan et al. |
| 2009/0110667 A1 | 4/2009 | Mozaffarian et al. |
| 2009/0130683 A1 | 5/2009 | Gaffney et al. |
| 2009/0142847 A1 | 6/2009 | Geddes et al. |
| 2009/0176217 A1 | 7/2009 | Sella-Tavor et al. |
| 2009/0202469 A1 | 8/2009 | Maruyama et al. |
| 2009/0226440 A1 | 9/2009 | Grey |
| 2009/0263474 A1 | 10/2009 | Banchereau et al. |
| 2009/0305305 A1 | 12/2009 | Van Dongen |
| 2009/0326614 A1* | 12/2009 | El-Sayed ............ A61K 41/0052 607/88 |
| 2010/0075891 A1 | 3/2010 | Ayalon-Soffer et al. |
| 2010/0104579 A1 | 4/2010 | Hubner et al. |
| 2010/0105086 A1 | 4/2010 | Landolfo et al. |
| 2010/0131286 A1 | 5/2010 | Houlgatte et al. |
| 2010/0144055 A1 | 6/2010 | Holzman et al. |
| 2010/0151471 A1 | 6/2010 | Faham et al. |
| 2011/0018948 A1 | 1/2011 | Justice et al. |
| 2011/0250464 A1 | 10/2011 | Wilson et al. |
| 2012/0028823 A1 | 2/2012 | Jung et al. |
| 2012/0235095 A1 | 9/2012 | Vigderman et al. |
| 2013/0102770 A9 | 4/2013 | Geddes |
| 2015/0226738 A1 | 8/2015 | Dai et al. |
| 2016/0146799 A1 | 5/2016 | Robinson et al. |

OTHER PUBLICATIONS

Talapatra et al., "Protein microarrays: challenges and promises", Pharmacogenomics (2002) 3(4) pp. 1-10.

Stranik, et al., "Plasmonic enhancement of fluorescence for sensor applications", Sesnors and Actuators B 107 (2005) 148-153.

Nagao, et al., "Plasmons in nanoscale and atomic-scale systems", Sci. Technol. Adv. Mater. 11 (2010) 054506 (12pp).

Ozturk, "The use of gold and silver nanoparticles for surface enhanced fluorescence (SEF) of dyes", Thesis submitted to the Graduate School of Natural and Applied Sciences of Middle East Technical University, Sep. 2010, 98 pages.

Hong, et al., "Near-Infrared-Flourescence-Enhanced molecular imaging of live cells on gold substrates", Angew. Chem. Int. Ed. 2011, 50, 4644-4648.

Tabakman, et al., "Plasmonic substrates for multiplexed protein microarrays with femtomolar sensitivity and broad dynamic range", Nature Communications, 2:466, Sep. 3, 2011.

Tabakman, et al., "A new approach to solution-phase gold seeding for SERS substrates", Small 2011, 7, No. 4, 499-505.

Fodor, et al. Light-directed, spatially addressable parallel chemical synthesis. Science. Feb. 15, 1991;251(4995):767-73.

Gudmundsson, et al. Genome-wide association and replication studies identify four variants associated with prostate cancer susceptibility. Nat Genet. Oct. 2009;41(10):1122-6. doi: 10.1038/ng.448. Epub Sep. 20, 2009.

International search report and written opinion dated Jun. 30, 2016 for PCT/US2015/059321.

Kohler, et al. Continuous cultures of fused cells secreting antibody of predefined specificity. Nature. Aug. 7, 1975;256(5517):495-7.

Liang, et al. Iron oxide/gold core/shell nanoparticles for ultrasensitive detection of carbohydrate-protein interactions. Anal Chem. Sep. 15, 2009;81(18):7750-6. doi: 10.1021/ac9012286.

Lockhart, et al. Expression monitoring by hybridization to high-density oligonucleotide arrays. Nat Biotechnol. Dec. 1996;14(13):1675-80.

McCafferty, et al. Phage antibodies: filamentous phage displaying antibody variable domains. Nature. Dec. 6, 1990;348(6301):552-4.

Metzker. Sequencing technologies—the next generation. Nat Rev Genet. Jan. 2010;11(1):31-46. doi: 10.1038/nrg2626. Epub Dec. 8, 2009.

Out, et al. Deep sequencing to reveal new variants in pooled DNA samples. Hum Mutat. Dec. 2009;30(12):1703-12. doi: 10.1002/humu.21122.

Pease, et al. Light-generated oligonucleotide arrays for rapid DNA sequence analysis. Proc Natl Acad Sci U S A. May 24, 1994;91(11):5022-6.

Turner, et al. Massively parallel exon capture and library-free resequencing across 16 genomes. Nat Methods. May 2009; 6(5): 315-6. doi: 10.1038/nmeth.f.248. Epub Apr. 6, 2009.

Voelkerding, et al. Next-generation sequencing: from basic research to diagnostics. Clin Chem. Apr. 2009;55(4):641-58. doi: 10.1373/clinchem.2008.112789. Epub Feb. 26, 2009.

\* cited by examiner

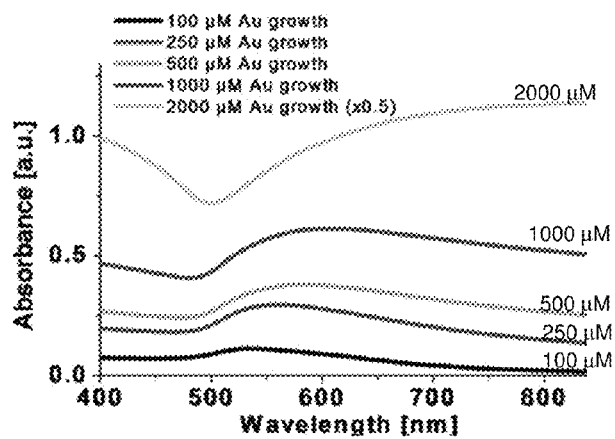
Figure 3A
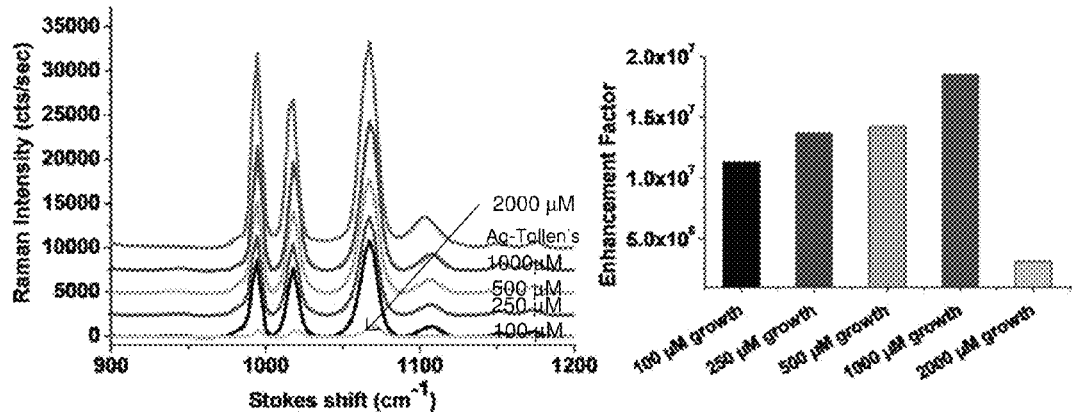
Figure 3B
Figure 3C
Figure 3A, 3B, 3C

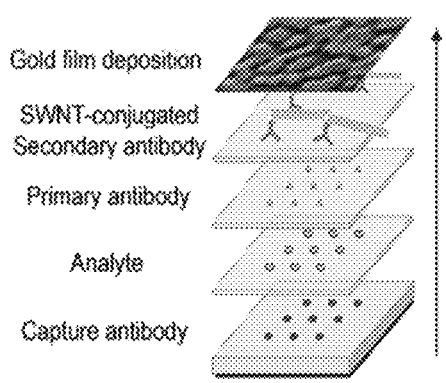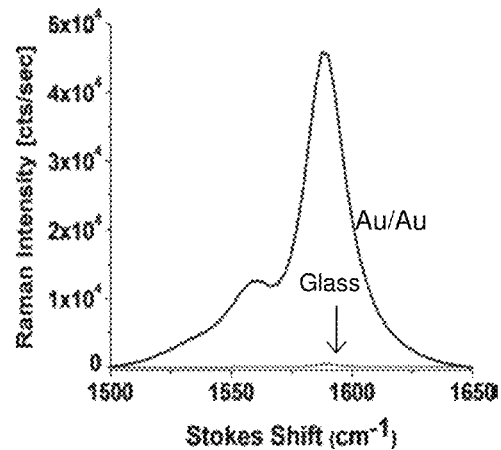
Figure 4A
Figure 4B
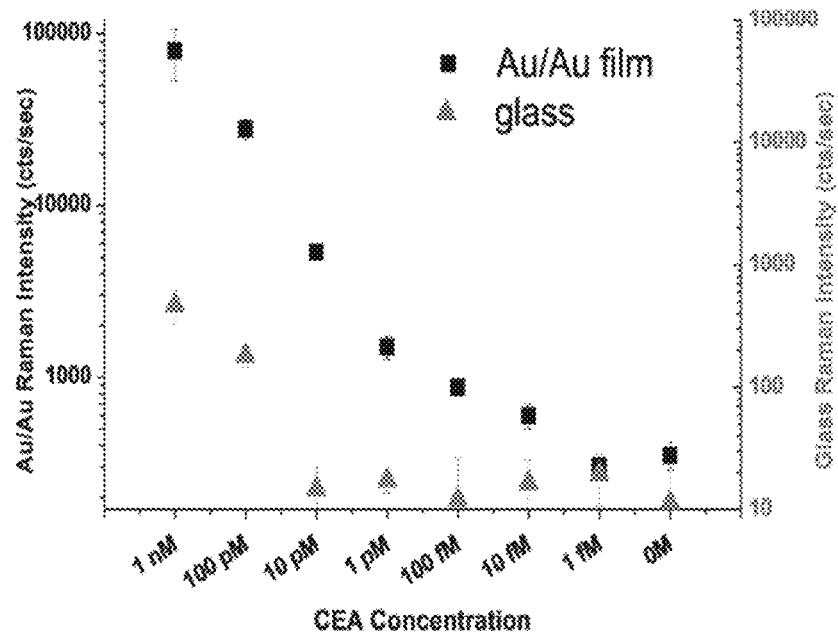
Figure 4C
Figure 4A, 4B, 4C

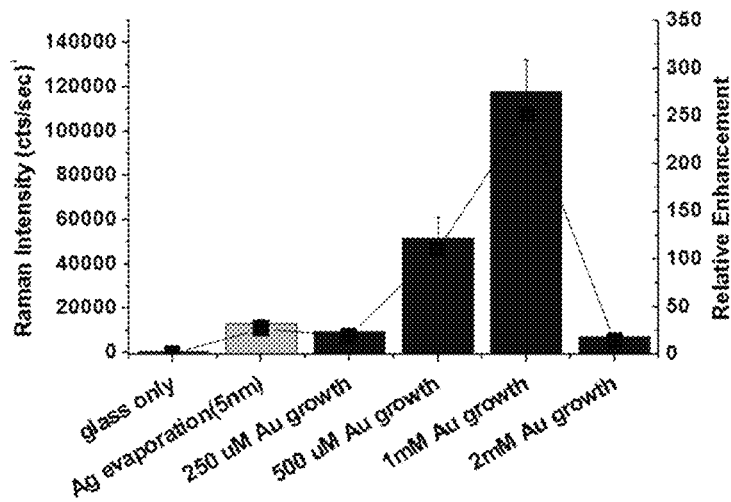
Figure 5A
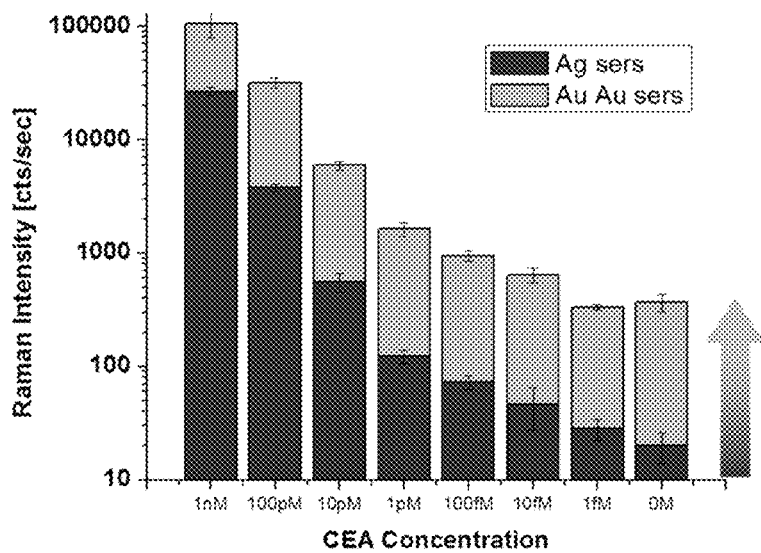
Figure 5B
Figure 5A, 5B

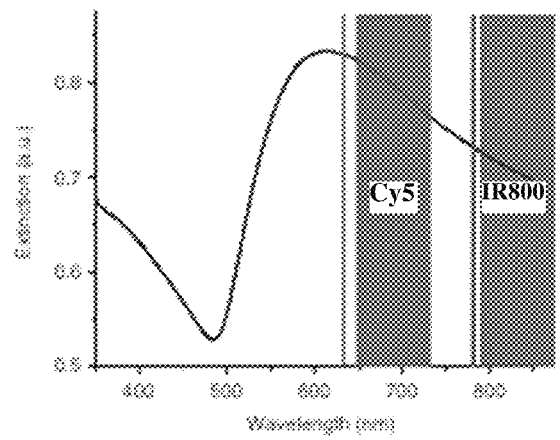
Fig. 6A
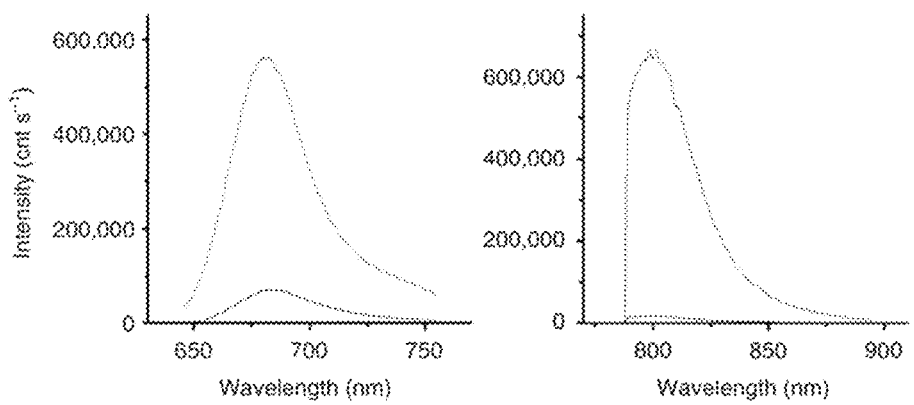
Fig. 6B
Figure 6A, 6B

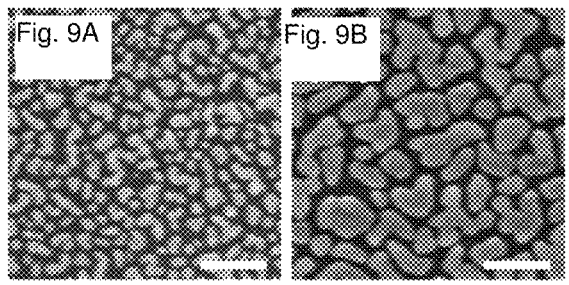
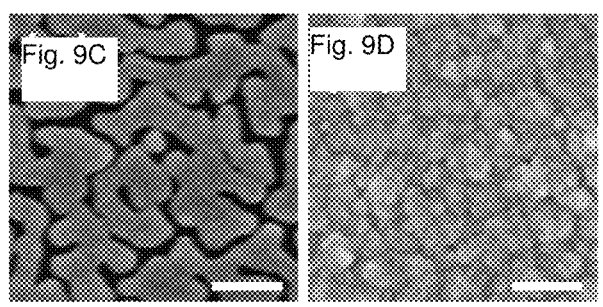
Figure 9A, 9B, 9C, 9D

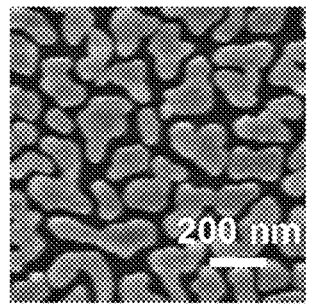 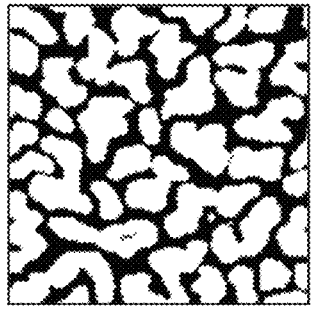 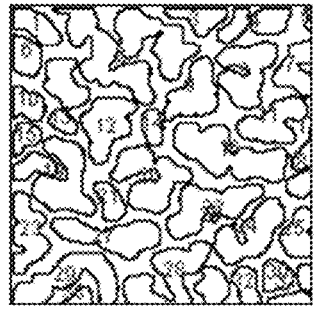
Figure 13 A        Figure 13B        Figure 13C
Figure 13D
Figure 13A, 13B, 13C, 13D

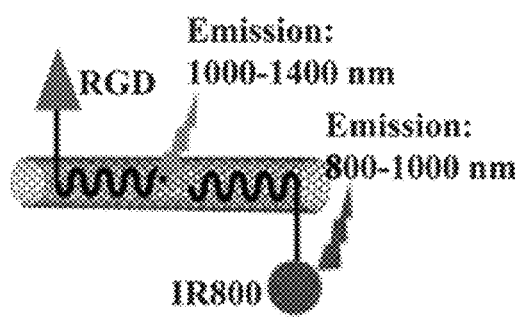
Figure 14A
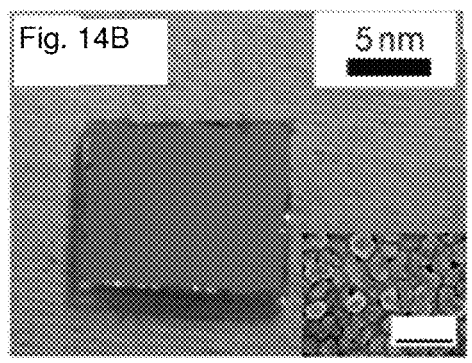
Figure 14B
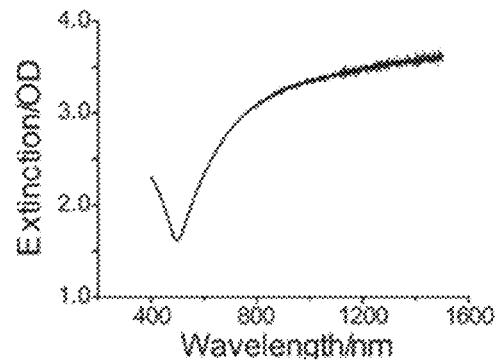
Figure 14C
Figure 14A, 14B, 14C

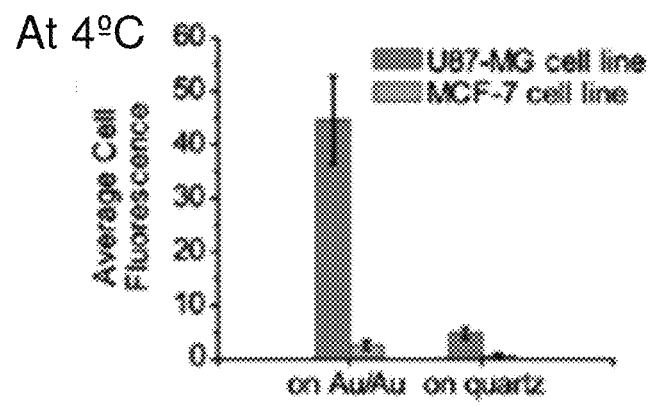
Figure 15A
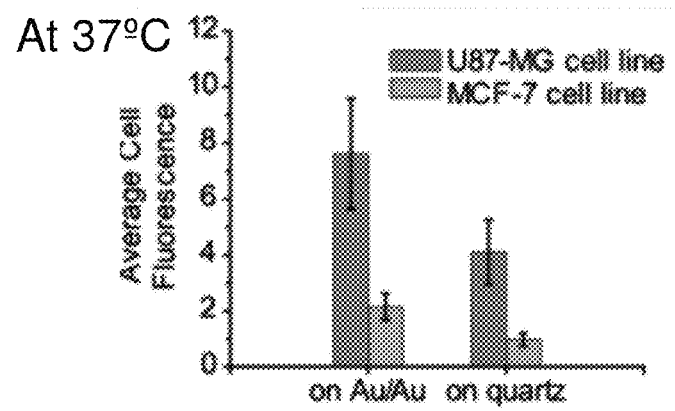
Figure 15B
Figure 15A, 15B

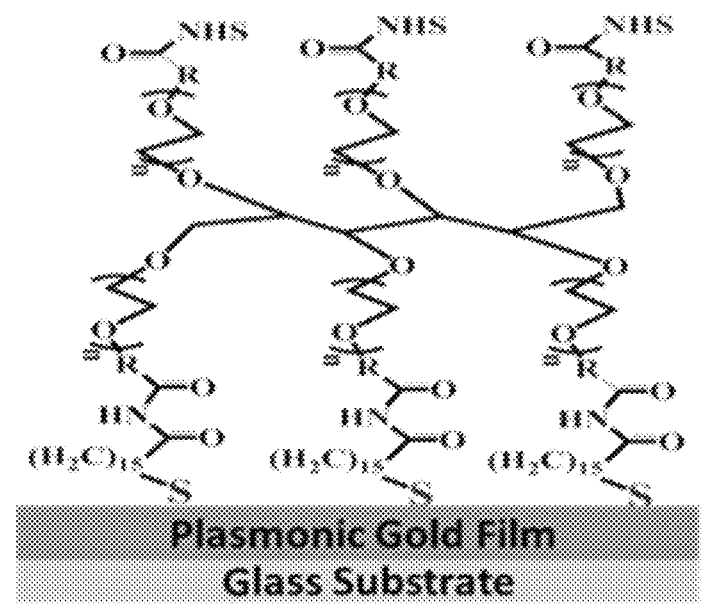
Figure 17A
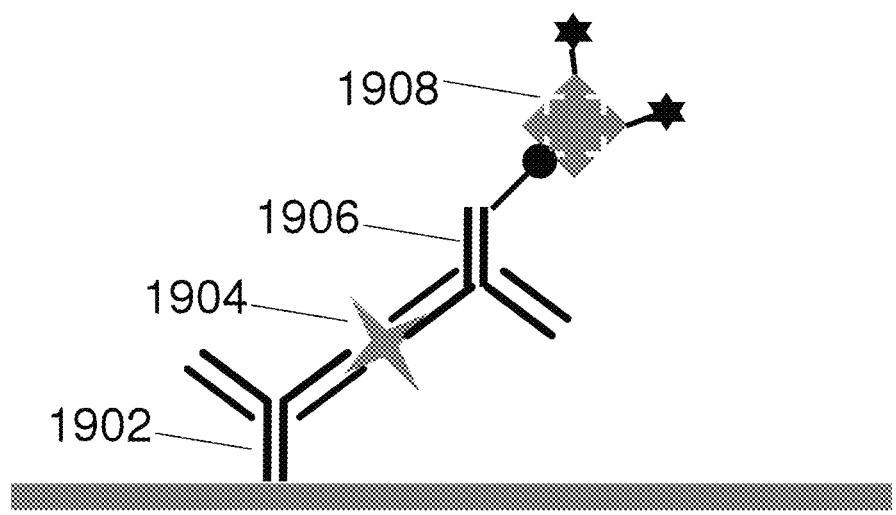
Figure 17B
Figure 17A, 17B

FLUORESCENCE ENHANCING PLASMONIC NANOSCOPIC GOLD FILMS AND ASSAYS BASED THEREON

CROSS-REFERENCE TO RELATED APPLICATIONS

This application claims priority from U.S. Provisional Patent Application No. 61/580,883, filed Dec. 28, 2011, which is hereby incorporated by reference in its entirety.

STATEMENT OF GOVERNMENTAL SUPPORT

This invention was made with Government support under contract CA119367 awarded by the National Institutes of Health and under contract CA135109 awarded by the National Institutes of Health. The Government has certain rights in this invention.

REFERENCE TO SEQUENCE LISTING, COMPUTER PROGRAM, OR COMPACT DISK

None.

BACKGROUND OF THE INVENTION

Field of the Invention

The present invention relates to the formation of nanostructured plasmonic metal films on substrates, where such plasmonic films are useful for spectroscopy and immunoassays, and, in exemplary aspects, to surface-enhanced Raman scattering (SERS) and near-infrared fluorescence enhancing (NIR-FE) gold substrates that can be applied on substrates containing biological, organic, or other molecules to be assayed.

INTRODUCTION

The present invention relates to plasmonic gold substrates are used as microarray platforms for fluorescence enhanced, multiplexed immunoassay of proteins down to 0.01 pg/ml of 1 fM level over 6 logs of dynamic range. The proteins detected include antibodies, autoantibodies, protein biomarkers for diseases such as cancer, cytokines and other biological molecules. Protein microarrays on a nanostructured gold platform with NIR-FE enable rapid, high throughput immunoassays with sensitivities superior to ELISA and RIA. These platforms can be applied to a variety of biological molecules.

Identification of bimolecular interactions and further application of such interactions has and is making great contribution to both scientific research and clinical diagnostics, exemplified by Yalow and Berson's success in measuring insulin level in human serum which was realized through radio immunoassay (RIA) based on insulin-antibody interactions. Applications based on biomolecular interactions have flourished for several decades. For example, measurement of protein biomarkers such as carbohydrate antigen 125 (CA-125) and carcinoembryonic antigen (CEA) are clinically employed for therapeutic monitoring of ovarian cancer. Identification of human antibodies against autoantigens is helping doctors to diagnose/predict autoimmune disease such as rheumatoid arthritis (RA), system lupus erythematosus (SLE), etc. Measurement of human antibodies against certain antigens is also applied as a tool for monitoring human immunity against corresponding disease types, such as Influenza hemagglutination inhibition (HI) assay for evaluation of human immunity against flu.

The first generation of immunoassays for identification of biomolecules interactions was heavily reliant on radioactivity owe to its extraordinary sensitivity, while people are looking for alternatives to bypass the safety issues related to radioisotopes. Based on enzymatic reaction which changes the optical density of the substrate, enzyme-linked immunosorbent assay (ELISA) has become the gold standard for current immunoassays due to its high sensitivity and ease of use. However, accompanied by the quantum leap of genomic and proteomic project, large number screening of biomolecules interactions is becoming a necessity for scientists and clinicians nowadays, requiring a third generation of immunoassays with multiplex ability. Planar microarray assays and Luminex bead suspension assays are emerging as useful tools for high throughput biomolecules interactions screening. For planar substrate supported immunoassays, biomolecules are immobilized on planar substrate as probes and binding of biomolecules is reflected by the fluorescence intensity from the detecting reagent on corresponding probe "spots". For Luminex bead assays, such probes are immobilized on polystyrene beads with unique fluorescence fingerprint and binding of biomolecules is also reflected by the fluorescence intensity from detecting reagent on corresponding bead. However, due to the same physical detection method, the sensitivity of traditional microarray and bead assays are no better than ELISA. Detecting biomarkers in serum resembles detecting needles in a haystack, as concentrations span up to nine orders of magnitude with relevant markers often present from nano-molar to femtomolar levels. Therefore assay sensitivity is an essential factor for evaluation of immunoassays besides multiplicity. Current planar microarray methodology is based largely on glass substrates or nitrocellulose substrates, with insufficient sensitivity for accurate protein marker quantification. Described below is a nanostructured gold (Au)-coated, plasmonic substrate capable of affording near-infrared fluorescence enhancement by ~100-fold. Protein microarrays on such plasmonic Au substrates demonstrated highly sensitive detection of proteins such as carcinoembryonic antigen (CEA) down to ~5 fM in whole serum, with a 6-order dynamic range. This plasmonic Au film is readily produced via a simple chemical method on a variety of substrates such as glass, affording fluorescence enhancement of NIR fluorophores by up to 100-fold. The ease-of-use and potential for rapid translation of this plasmonic protein chip technology may afford improvements in high-throughput screening of biomolecules interactions with great sensitivity.

RELATED ART

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Surface-enhanced Raman scattering (SERS) and near-infrared fluorescence enhancement (NIR-FE) effects provided by plasmonic substrates have been shown to vastly improve signal-to-noise ratios compared to traditional Raman scattering or fluorescence measurements, affording improvements to assays based upon the methodologies. Both enhanced spectroscopies are based on local field enhancement that occurs in the near vicinity of metallic nanoparticles when surface plasmon oscillations are driven for a specific optical wavelength. However, to date, preparation of highly stable plasmonic gold substrates requires complicated and expensive methodologies and instrumentation.

For example, utilizing the advantages of SERS, glucose, oligonucleotides, explosives and other analytes of interest have been detected at high sensitivity.[3-6] Recently, high sensitivity protein detection based upon bioconjugated single-walled carbon nanotube (SWNT) Raman labels and SERS in protein array format has been demonstrated.[7] However, preparation of the SERS-active substrate required undesirable vacuum deposition of gold films and thermal annealing of the assay substrates at 400° C.

Plasmonic SERS and NIR-FE-active substrates are often made by vacuum evaporation or sputtering,[7-9] high temperature annealing,[7] and Langmuir-Blodgett film transfer,[10] amongst other methods.[11-16] For many assays, especially those with biological components, it is desirable to produce plasmonic metal nanostructures without exposing the assay components to harsh conditions, such as high temperatures, organic solvents, and high vacuum. Deposition of desirable films from the aqueous phase circumvents many of the aforementioned problems, yet provides the opportunity to prepare large area, SERS and NIR-FE-active films.

Purely solution phase chemical synthesis of silver substrates has been reported for SERS and NIR-FE applications,[17] but Ag suffers from oxidation and instability problems, especially when reactive species are present, as is the case in bioassays. Gold films are promising as highly stable SERS substrates, and may be prepared from pre-made gold nanoparticle (Au NP) precursor seeds by reduction of chloroauric acid solution by hydroxylamine.[11, 18] However, deposition of pre-made Au NP seeds onto a substrate requires an amino- or mercaptosilane functionalized substrate, and thus the methodology is not directly amenable to polymeric or other complex surfaces, such as protein microarrays.[19]

SPECIFIC PATENTS AND PUBLICATIONS

Nathan et al. U.S. Pat. No. 6,624,886, entitled "SERS Substrates Fformed by Hydroxylamine Seeding of Colloidal Metal Nanoparticle Monolayers," discloses methods for preparing colloidal metal nanoparticles, in which seed colloids are added to a solution of reductant mixed with a solution containing a source of metal ions. A method is disclosed in which the seeds are colloidal gold nanoparticles, the source of gold ions is $HAuCl_4$, and the reductant is $NH_2OH$. This method relies on the immobilization of preformed colloidal gold particles to a functionalized substrate for the initial seeding step.

US 20090142847A1 by Geddes et al., entitled "Metal Enhanced Fluorescence-based Sensing Methods," discloses a detection system for determining unbound bilirubin in neonatal serum, in which the system utilizes a metallic material deposited on a substrate.

Hong et al., "Metal-Enhanced Fluorescence of Carbon Nanotubes," J. Am. Chem. Soc. 132:15920-15923 (published on line Oct. 27, 2010) discloses metal enhanced fluorescence of surfactant-coated, water soluble SWNTs on solution-grown Au films seeded by Au nanoparticles (AuAu films). A decrease in the enhancement factor was observed when the SWNTs were placed further from the AuAu surface when using alkanethiol monolayers or $Al_2O_3$ layers grown on Au by deposition.

Tabakman et al. "Plasmonic substrates for multiplexed protein microarrays with femtomolar sensitivity and broad dynamic range," Nature Communications 2:466 (Sep. 11, 2011) contains a description by the present inventors of protein microarrays on a novel nanostructured, plasmonic gold film with near-infrared fluorescence enhancement of up to 100-fold.

Hong, G. S. et al. "Near-Infrared-Fluorescence-Enhanced Molecular Imaging of Live Cells on Gold Substrates," Angew Chem Int Edit 50, 4644-4648 (Apr. 19, 2011) contains a description by the present inventors of the present Au/Au films prepared on quartz through solution phase growth, and or SWBT-IR800-RGD conjugates.

Hong, G. et al. "Three-dimensional imaging of single nanotube molecule endocytosis on plasmonic substrates," Nat Commun 3, 700 (Feb. 28, 2012) contains a description by the present inventors of near-infrared fluorescence enhancement of carbon nanotubes on a gold plasmonic substrate Tabakman, S. M., Chen, Z., Casalongue, H. S., Wang, H. L. & Dai, H. J. "A New Approach to Solution-Phase Gold Seeding for SERS Substrates," Small 7, 499-505 (3 Jan. 2011) contains a description by the present inventors of the presently used solution phase gold seeding to create a highly stable SERS-active gold substrate.

BRIEF SUMMARY OF THE INVENTION

The following brief summary is not intended to include all features and aspects of the present invention, nor does it imply that the invention must include all features and aspects discussed in this summary.

The present invention comprises, in certain aspects, a method for spectroscopically detecting an analyte in a sample, using a specially prepared nanostructured plasmonic gold film interacting with said sample. As described below, the gold film may be applied to a variety of substrates and provides a SERS (surface-enhanced Raman Spectroscopy) substrate and/or NIR-FE (near-infrared fluorescence enhancement) for spectroscopic detection of analytes applied to the surface. The substrate will have a solid surface, preferably an inert surface, to support the assay materials and the gold film. The substrate supports a gold film, coupled to said sample, and applied using certain steps. The gold film is plasmonically active and spectroscopically interacts with the analyte and/or a label on the analyte.

The method is particularly well suited to detection of biological or chemical analytes, using a soluble near-infrared label for detection. The film is referred to as "discontinuous" in the sense that it presents "isolated island areas," as described below, where the islands are separated from each other by gaps in the material (gold) forming the islands.

In certain aspects of the invention, the plasmonic properties of the film comprise a NIR fluorescence enhancement (NIR-FE) activity; the analyte is labeled with an organic dye that is enhanced by the NIR-FE. In certain aspects of the invention, the dye fluoresces in the NIR (600 nm-2 μm).

In certain aspects of the invention the step of applying the gold film occurs either (i) after application of the sample, and the gold film is applied to the sample; or (ii) before application of the sample, and the sample is applied to the gold film.

In certain aspects of the invention, isolated areas ("isolated island areas") are produced to maximize the signal being detected through NIR-FE. Au(0) (Au$^0$, i.e. oxidation number of zero) isolated island areas are used. The Au(0) clusters (isolated island areas) may be about 20-30,000 nm$^2$ in area, with a distance between clusters of between about 10 and 60 nm. In certain embodiments, the isolated island areas may be between about 100 nm$^2$ and 250000 nm$^2$ in area; the gaps may be between 1-1000 nm; and the height of the isolated island areas may be 5-500 nm.

In certain aspects of the invention, there is provided a biosensor for use in a SERS or fluorescent spectroscopic detection system, comprising (a) a substrate for supporting samples; (b) a discontinuous gold film applied directly or indirectly to said substrate, said gold film having isolated island areas of gold grown on gold seeds; and (c) an array of biological samples disposed in contact with the gold film. The gold substrates are used as microarray platforms for fluorescence enhanced, multiplexed immunoassay of proteins down to 0.01 pg/ml of 1 fM level over 6 logs of dynamic range. The proteins include antibodies, autoantibodies, protein biomarkers for diseases, cytokines and other biological molecules.

In certain aspects, the present invention comprises a microarray comprising: (a) a substrate; (b) a discontinuous gold film applied to said substrate, said gold film having isolated island areas of between about 100 nm$^2$ and 250,000 nm$^2$ configured to enhance plasmonic near-infrared fluorescence; and (c) an array of biological molecules, for use as capture agents specifically binding to an analyte, disposed as different molecular species (i.e. different specific proteins, different cytokines, different DNA sequences, antibodies of different specificities, etc.) in discrete locations on the discontinuous gold film and coupled to the discontinuous gold film, whereby near-infrared fluorescence emission caused by an analyte captured by a capture agent is enhanced by the discontinuous gold film.

In certain aspects, the present invention comprises a microarray as described above wherein the isolated island areas are separated by gaps of between 5 and 100 nm.

In certain aspects, the present invention comprises a microarray as described above wherein the isolated island areas are between 10,000 nm$^2$ and 25,000 nm$^2$ in area.

Other aspects of certain embodiments of the invention are as follows: The isolated island areas may be formed by one of (a) separated gold seeds from a solution phase deposition, (b) separated gold islands etched on the film; (c) discrete gold particles or (d) gold nanorods or nanoplates. The microarray may further comprise a self-assembled monolayer between the discontinuous gold film and the biological molecules. The microarray may further comprise a branched PEG layer between the gold film, the self-assembled monolayer and the analyte capture agents.

In certain aspects, the present invention comprises a microarray as described above further comprising an avidin or streptavidin layer between the discontinuous gold film, and the biological molecules. In certain aspects, the present invention comprises a microarray as described above wherein the biological molecules are one of proteins, peptides, antigens, antibodies, nucleic acids, polysaccharides, or cells. In certain aspects, the present invention comprises a microarray as described above wherein the proteins are cytokines. In certain aspects, the present invention comprises a microarray as described above wherein the gold film is over the array of biological molecules.

In certain aspects, the present invention comprises a microarray as described above wherein the gold film is under the array of biological molecules.

In certain aspects, the present invention comprises a microarray as described above wherein a self-assembled monolayer is applied on the discontinuous gold film, a hydrophilic polymer is linked to a self-assembled monolayer on the discontinuous gold film, and the biological molecules are linked to the hydrophilic polymer.

In certain aspects, the present invention comprises a method for preparing a microarray, comprising: (a) applying to a substrate a solution containing gold ions; (b) precipitating the gold ions from solution onto the substrate using a basic solution; (c) reducing the gold ions precipitated onto the substrate in step (b) to produce on the substrate Au(0) seed particles; (d) adding gold ions from solution to the gold seeds from step (c) together with a reducing agent to grow isolated island areas in a discontinuous film; and (e) applying to the discontinuous gold film an array of biological for use as capture agents specifically binding to an analyte, disposed as different molecular species in discrete locations on the discontinuous gold film and coupled to the discontinuous gold film, whereby near-infrared fluorescence emission caused by an analyte captured by a capture agent is enhanced by the discontinuous gold film.

In certain aspects, the present invention comprises a method as described above wherein the Au(0) seeds are between 0.1 nm$^2$ and 100 nm$^2$ in area and between about 10 nm and 100 nm apart. In certain aspects, the present invention comprises a method as described above wherein the isolated island areas are between 100 nm$^2$ and 250,000 nm$^2$ in size.

In certain aspects, the present invention comprises a method as described above wherein the gaps between isolated island areas are between about 1 nm to 1000 nm. In certain aspects, the present invention comprises a method as described above wherein the gaps are about 10 nm.

In certain aspects, the present invention comprises a method as described above wherein the isolated island areas produce plasmonic modes in the 500-2000 nm NIR range.

In certain aspects, the present invention comprises a method as described above further comprising the step of modifying the gold film for attachment of the biological molecule by applying to the gold film a material selected from the group consisting of thiol, mercaptan, poly-L lysine, dextran, amino dextran, carboxy-methyl dextran and polyethylene ethylene glycol. In certain aspects, the present invention comprises a method as described above wherein the material is branched polyethylene glycol. In certain aspects, the present invention comprises a method as described above further comprising the step of coating the gold film with a layer of an avidin material.

In certain aspects, the present invention comprises a method as described above comprising the step of applying biotinylated biological molecules to the avidin material.

In certain aspects, the present invention comprises a method as described above further comprising the step of applying a self-assembled thiol containing monolayer directly on the gold film, applying a layer of polyethylene glycol to the self-assembled monolayer via covalent reactions with the terminal groups of the SAM, and applying the analyte capture agents to the terminal groups of polyethylene glycol layer.

In certain aspects, the present invention comprises a method as described above wherein the isolated island areas have at least one of the following properties: (a) about 100

$nm^2$ and 250,000 $nm^2$ in area, (b) a gap distance between about 1 and 1000 nm, and (c) heights of 5-500 nm.

In certain aspects, the present invention comprises a method as described above wherein the isolated island areas have heights of between 5 and 500 nm, or between 30 nm and 100 nm.

In certain aspects, the present invention comprises a method as described above wherein the reducing step is carried out using one of ascorbic acid, hydrazine, hydroxylamine, ammonium borohydrate, formic acid and a hydrogen gas atmosphere. In certain aspects, the present invention comprises a method as described above wherein the substrate is one of glass, polyvinyl chloride, polydimethyl siloxane, quartz, silicon, silicon dioxide and other solid substrates.

In certain aspects, the present invention comprises a method of detecting one or more analytes in a sample, comprising: (a) providing a microarray having (i.) a substrate; (ii.) a discontinuous gold film applied to said substrate, said gold film having nanometer sized islands of between about 100 $nm^2$ and 250,000 $nm^2$ configured to enhance plasmonic near-infrared fluorescence; and (iii.) an array of biological molecules, for use as capture agents specifically binding to an analyte, disposed as different molecular species in discrete locations on the discontinuous gold film and coupled to the discontinuous gold film, whereby near-infrared fluorescence emission caused by an analyte captured by a capture agent is enhanced by the discontinuous gold film; and (b) applying to said microarray said sample and a near-infrared fluorphore label for said one or more analytes.

In certain aspects, the present invention comprises a method as described above wherein the label emits in the 500-1000 nm range. In certain aspects, the present invention comprises a method as described above wherein the label emits in the NIR, including the NIR range of 650-900 nm. In certain aspects, the present invention comprises a method as described above wherein the label is one of IRDye 800, Cy7, or Cy5. Other NIR dyes may be used.

In certain aspects, the present invention comprises a method as described above wherein the step of applying a label comprises applying multiple fluorophores with non-overlapping fluorescence in the 500-1000 nm range to detect different analytes. In certain aspects, the present invention comprises a method as described above wherein the biological molecules are purified proteins. In certain aspects, the present invention comprises a method as described above wherein the biological molecules are antibodies. In certain aspects, the present invention comprises a method as described above wherein the antibodies are antibodies to cytokines.

BRIEF DESCRIPTION OF THE DRAWINGS

FIG. 1 is a series of images showing gold-on-gold film (Au/Au) formation on glass.

FIG. 3A shows an absorbance spectra of Au/Au films seeded at a fixed concentration of 5 mM $HAuCl_4$, and grown at the indicated concentrations of $HAuCl_4$ and $NH_2OH$; FIG. 3B is a graph showing benzenethiol Raman scattering spectra of self-assembled monolayers formed on the various Au/Au films at the indicated concentrations of $HAuCl_4$ and $NH_2OH$, shown with a benzenethiol spectrum obtained from a silver minor (Tollen's) substrate.[17] FIG. 3C is a graph showing the estimated enhancement factors for benzenethiol monolayers on the various Au/Au films at the indicated concentrations of $HAuCl_4$ and $NH_2OH$.

FIG. 4A is a schematic diagram of a microarray immunoassay performed on glass, with Au/Au film deposited atop the bioassay substrate, from the solution phase, to provide SERS of SWNT Raman labels. FIG. 4B a Raman scattering spectrum of SWNT G-band with and without Au/Au film deposition demonstrating the SERS effect where deposition of the Au/Au film from solution onto the SWNT-labeled protein assay yields a G-band enhancement of ~200-fold. FIG. 4C is a scatter plot showing the observed G-band Raman intensity for 1 nM-1 fM CEA (scarcinoembryonic antigen) spiked into dilute serum with and without Au/Au SERS, along with blank control ("0M").

FIG. 5A is a bar graph showing the average G-band scattering intensities recorded following SWNT immunoassay of 1 nM CEA as described in FIG. 3. FIG. 5B is a bar graph showing SWNT G-band Raman intensities following CEA immunoassay for Au/Au films (recorded at 8 mW) compared with 5 nm-silver on glass substrates (recorded at 20 mW).

FIG. 6A shows a graph showing the extinction spectrum of Au/Au film overlaid with the excitation (line) and emission (shaded area) regions of Cy5 and IR800 dyes. FIG. 6B is a pair of line graphs showing the fluorescence emission spectra of IgG-bound Cy5 (left) and IR800 (right) dried onto the Au/Au film from (a) as well as glass for comparison.

FIG. 9 is a set of scanning electron microscope (SEM) images of gold-on-gold (Au/Au) films of various thickness used for near-infrared fluorescence enhancement. FIG. 9A is of gold-on-gold (Au/Au) films of 3 mM seeding and 250 µM growth. FIG. 9B is of gold-on-gold (Au/Au) films of 3 mM seeding and 750 µM growth. FIG. 9C is of gold-on-gold (Au/Au) films of 3 mM seeding and 1000 µM growth. FIG. 9D is of gold-on-gold (Au/Au) films of 3 mM seeding and 3 mM growth. Scale bars represent 250 nm. Gold nano-islands ("isolated island areas") grow and coalesce with neighboring nanoparticles at increasing growth concentrations.

FIG. 13A is a SEM images of 3 mM/750 μM Au/Au film. FIG. 13B is a corresponding ImageJ particle analysis mask FIG. 13A. FIG. 13C is a corresponding ImageJ particle analysis outline of FIG. 13A. FIG. 13D is a similar Au/Au film showing Au island height. Extracted island perimeters and film height were used to estimate available surface area for protein binding.

FIG. 14A is a diagram showing the SWNT-IR800-RGD conjugate, with the emission ranges of SWNTs and IR800 dye labeled. FIG. 14B a digital photograph of a typical Au/Au substrate used for NIR-FE imaging of cells plated on this substrate. FIG. 14C is a UV-Vis-NIR extinction spectrum of the Au/Au film.

FIG. 15A is a bar chart of average cell fluorescence in SWNT-IR800-RGD stained U87-MG cells and in similarly treated MCF-7 cells at 4° C. on Au/Au film and on quartz respectively. FIG. 15B is a bar chart of average cell fluorescence in SWNT-IR800-RGD stained U87-MG cells and in similarly treated MCF-7 cells at 37° C. on Au/Au film and on quartz respectively.

FIG. 17A is a schematic diagram of a multilayer surface chemistry on gold film, showing a glass substrate with a plasmonically active gold film thereon. Attached to the film are a self-assembled monolayer and a hydrophilic polymer. FIG. 17B is a schematic diagram of a four layer (antibody-antigen-antibody-label) antibody based cytokine microarray assay strategy.

FIG. 18A shows the averaged fluorescence intensity over spots in each row of capture antibodies when only IL-1β was incubated on the antibody microarray at 1 pM. FIG. 18B shows the averaged fluorescence over spots in each row when a cocktail (without IL-1β) of VEGF, IL-4, IL-6, IFN-γ, and TNF were incubated on the microarray at 1 pM each (10 pM for VEGF). FIG. 18C shows the averaged fluorescence intensity over spots in each row of capture antibodies when only IFN-γ was incubated on the antibody microarray at 1 pM. FIG. 18D shows the averaged fluorescence over spots in each row when a cocktail (without IFN-γ) of VEGF, IL-1β, IL-4, IL-6, TNF were incubated on the microarray at 1 pM each (10 pM for VEGF).

DETAILED DESCRIPTION OF THE PREFERRED EMBODIMENTS

Definitions

Figures 1A, 1B, 1C, 1D:
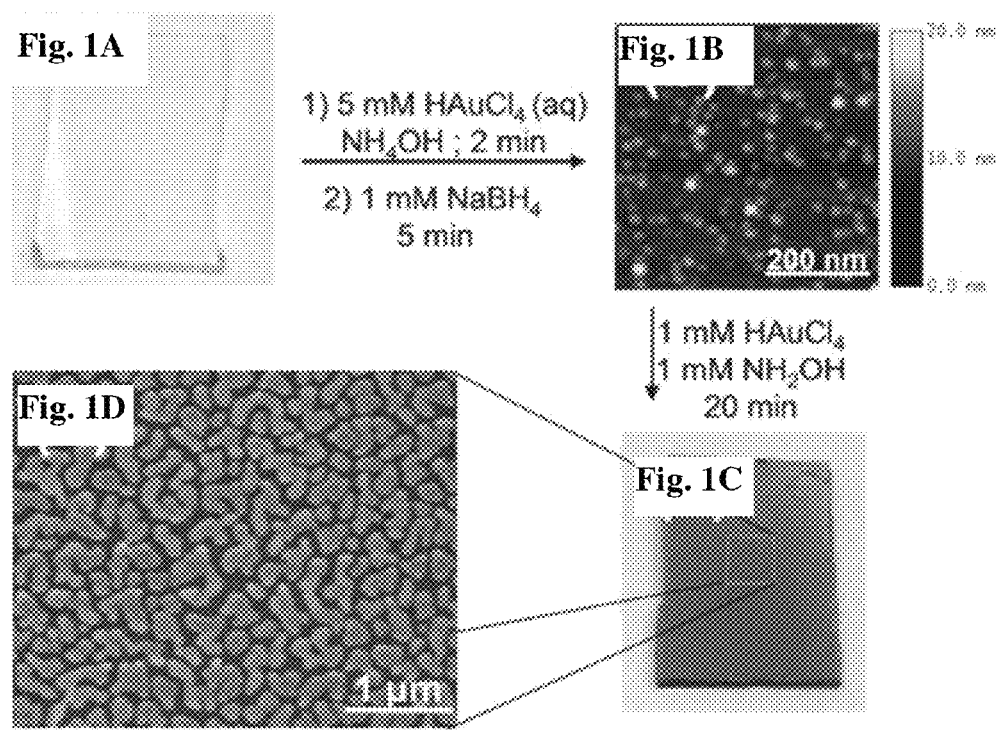
FIG. 1A shows a glass slide.
FIG. 1B is a tapping mode AFM image showing subsequent reduction rapidly yields densely packed $Au^0$ nanoparticles on a variety of substrates.
FIG. 1C shows subsequent reduction and additional chloroauric acid by hydroxylamine "grow" the gold nanoparticles into a uniform gold-on-gold film with nanoscale structure.
FIG. 1D is a SEM imaging showing isolated island areas separated by small gaps.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, physics and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. A subrange is to be included within a range even though no sub-range is explicitly stated in connection with the range. As a nonlimiting example, a range of 120 to 250 includes a range of 120-121, 120-130, 200-225, 121-250 etc.

The term "about" has its ordinary meaning of approximately and may be determined in context by experimental variability. In case of doubt, "about" means plus or minus 5% of a stated numerical value.

The term "protein" has the art-recognized meaning of a polymer of amino acids without regard to the length of the polymer, provided that the protein has specific binding properties. This term also does not specify or exclude chemical or post-expression modifications of the polypeptides of the invention, although chemical or post-expression modifications of these polypeptides may be included or excluded as specific embodiments. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 112, 1983; Seifter et al., *Meth Enzymol* 182:626

646, 1990; Rattan et al., Ann NY Acad Sci 663:48 62, 1992). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

Many proteins are antigens known for use in immunoassays. For example, carcinoembryonic antigen CEA is a glycoprotein involved in cell adhesion and a cancer biomarker. Included specifically within this definition and contemplated for use herein are serum proteins, human proteins, and human serum proteins.

The term "antibody" has the art-recognized meaning of several classes of structurally related proteins, also known as immunoglobulins, that function as part of the immune response of an animal, which proteins include IgG, IgD, IgE, IgA, IgM and related proteins which specifically bind to their cognate antigens. The term "antibody" here refers to an antibody specifically binding to a single antigen specificity rather than a mixed population of antibodies. Antibodies as contemplated herein are any antibody-like molecule useful in an immunoassay, including known direct and indirect ("sandwich") immunoassays.

The term "autoantibody" has the art-recognized meaning of an antibody that is or was present in a subject and is directed to an antigen present in the subject. Exemplary autoantibodies are those associated with diabetes, as described e.g. in Pihoker et al. "Autoantibodies in Diabetes," Diabetes 2005 December; 54 Suppl 2:S52-61 and those listed in U.S. Pat. No. 7,491,534, "Methods for altering cell fate to generate T-cells specific for an antigen of interest."

The term "specific binding" means that binding which occurs between such paired species as enzyme/substrate, receptor/agonist or antagonist, antibody/antigen, complementary polynucleotides (polynucleic acids) and lectin/carbohydrate which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two, which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The term "cytokine" has the art-recognized meaning of a protein which is part of a class of low molecular weight nonantibody proteins released by one cell population on contact with specific antigen, which act as intercellular mediators, as in the generation of an immune response. These proteins are secreted by various cell types and involved in cell-to-cell communication, coordinating antibody and T cell immune interactions, and amplifying immune reactivity. Cytokines include colony-stimulating factors, interferons, interleukins, and lymphokines, which are secreted by lymphocytes. Specific examples include IL-1α/β, IL-2, IL-4, IL-6, IL-8, TNF-α, IFN-γ, G-CSF, GM-CSF, EGF, MIF, MIP-1, MCP-1, RANTES, TIMP-1, and VEGF.

The term "polynucleotide" or "polynucleic acid" has the art-recognized meaning of a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Polynucleotides typically range in size from a few monomeric units, e.g., 5-40, when they are usually referred to as "oligonucleotides," to several thousand monomeric units. Polynucleotides are contemplated as analyte for detection in the present assays, and may be also used as part of a labeling step, through specific hybridization.

The term "plasmonically active" in reference to a material means a material which supports plasmons, particularly surface plasmons, thereby exhibiting plasmonic properties. Surface plasmons have been used to enhance the surface sensitivity of several spectroscopic measurements including fluorescence, Raman scattering, and second harmonic generation. The term may be more fully understood by reference to Wilson et al. "Directly fabricated nanoparticles for Raman scattering," US Pub. 20110250464.

The phrase "plasmonic properties" refers to properties exhibited by surface plasmons, or the collective oscillations of electrical charge on the surfaces of metals. In this sense, plasmonic properties refers to measurable properties, as described e.g. in Nagao et al. "Plasmons in nanoscale and atomic-scale systems," Sci. Technol. Adv. Mater. 11 (2010) 054506 (12 pp), describing plasmonic sensors, such as those used for surface-enhanced IR absorption spectroscopy (SEIRA), surface-enhanced Raman scattering (SERS). Another plasmonic property is plasmon-enhanced fluorescence, described e.g. in Sensors and Actuators B 107 (2005) 148-153. That study presented a combination of a nanosphere lithography technique and a surface-enhanced fluorescence technique as a strategy to increase the sensitivity of biochips based on the fluorescent dye Cy5.

The term "nanometer sized" refers a size that is generally less than a uM in length, or 1 uM squared in area.

The term "islands" or "isolated island areas" is used herein to refer to nanometer-sized gold islands, or discontinuous gold nanostructures. The islands may be a variety of shapes and configurations that provide nanometer sized raised areas of material (e.g. gold) separated by gaps without such material. The isolated island areas may be particle or rod like shapes. When formed by etching, they may be squares, circles, rectangles, triangles, hexagons, or other irregular shapes. When formed by growth from solution, they will be randomly shaped. In certain embodiments, the present isolated island areas are various shapes in a single film, meaning that the isolated island areas differ in size and shape within a single film. This term is also used to refer to separated structures such as gold nanorods, or nanospheres, such as described e.g. in "High-yield synthesis of gold nanorods with optical absorption at wavelengths greater than 1000 nm using hydroquinone," US 2012/0235095, "Gram-Scale Synthesis of Well-Defined Gold Nanorods," US 2011/

018948, "Gold nanoparticles and method of synthesizing the same," US 2006/0021468, etc.

The term "NIR fluorescence enhancement" or "NIR-FE" is used to mean an enhancement of near-infrared fluorescent intensity of a fluorophore in proximity to a metal where fluorophores in the excited state undergo near-field interactions with the metal particles to create plasmons. The enhancement results from plasmon-coupling and amplification.

The term "sample" is used in a broad sense to include any material, including an organic material, serum, plasmas, whole blood, saliva, living, or non-living, that may exist in nature, or be created by a natural process. A sample may be synthetic, e.g. when one wishes to measure the amount of or presence of an inorganic substance in a mineral sample. The sample will be presumed to contain an analyte, that is, the chemical or biological substance that undergoes analysis or detection in an assay.

The term "self-assembled monolayer" (SAM) refers to a spontaneously adsorbed monolayer film as is known to assemble onto a gold surface. This has been demonstrated for a wide variety of functional groups such as sulfides, phosphines, thiols, and disulfides. Particularly included are SAMs that reveal a SERS signal, such as 4-mercaptobenzoic acid (4-MBA) self-assembled monolayers on gold substrates. Also preferred is a benzenethiol SAM. Benzenethiol is also a Raman-active molecule capable of forming a SAM. Like 4-MBA, it's useful for probing the extent of SERS from the gold film in a controllable way. Benzene thiol SAMs are further described e.g. in U.S. Pat. No. 6,755,953, entitled "Method for forming ordered structure of fine metal particles," issued Jun. 29, 2004.

The term "NIR label" means a near-infrared label with fluorescence emission wavelength >~600 nm, such as carbocyanine dye (for example, an indocyanine dye), that optically comprises a functional group, for example, a succinimidyl ester, that facilitates covalent linkage to a cellular component. Exemplary dyes include, for example, Cy5, Cy5.5, and Cy7, each of which are available from GE Healthcare; VivoTag-680, VivoTag-5680, VivoTag-5750, each of which are available from VisEn Medical; AlexaFluor660, AlexaFluor680, AlexaFluor700, AlexaFluor750, and Alexa Fluor790, each of which are available from Invitrogen; Dy677, Dy676, Dy682, Dy752, Dy780, each of which are available from Dyonics; DyLight547 and DyLight647, each of which are available from Pierce; HiLyte Fluor 647, HiLyte Fluor 680, and HiLyte Fluor 750, each of which are available from AnaSpec; IRDye 800, IRDye800CW, IRDye 800RS, and IRDye 700DX, each of which are available from Li-Cor; and ADS780WS, ADS830WS, and ADS832WS, each of which are available from American Dye Source. NIR labels can be enhanced by NIR fluorescence enhancement (NIR-FE), whereby gold nanostructures favorably modify the spectral properties of fluorophores and alleviate some of their more classical photophysical constraints.

The term "NIR" means near-infrared, particularly in the sense of NIR fluorescence. The term also means the near-infrared region of the electromagnetic spectrum (from 0.6 to 3 μm).

The term "SERS" refers to surface enhanced Raman spectroscopy, as described in detail below. This is a surface-sensitive technique that enhances Raman scattering by molecules adsorbed on rough metal surfaces. SERS employs surfaces prepared using a distribution of metal nanoparticles on the surface as well as using lithography. The shape and size of the metal nanoparticles strongly affect the strength of the enhancement because these factors influence the ratio of absorption and scattering events. SERS relies heavily on plasmon resonances resulting from optical properties of metallic structures, such as gold or silver colloids or surfaces.

The term "Raman label" means a reagent that provides a strong Raman signal, particularly in SERS. Examples are given in U.S. Pat. No. 7,824,926, such as dithiobisbenzonic acid, 4-mercaptobenzoic acid, 2-naphthalenethiol, thiophenol, 4,4'-dithiobis(succinimidylbenzoate), direct red 81, Chicago sky blue, p-dimethylaminoazobenzene, 4-(4-Aminophenylazo)phenylarsonic acid monosodium salt, 1,5-difluoro-2,4-dinitrobenzene, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles. Carbon nanotubes are also known for use as Raman labels.

The term "spectroscopic" or "spectroscopically" refers to a method to study a sample based on the interaction between matter and radiated energy. A light is applied to a sample area and effect of the light on the sample area is determined. This may include analysis of the reflected or refracted light, or the effect of the light on the sample area, which varies depending on the state of the sample. Spectroscopic methods may be distinguished from chemical or biological methods in which modulation of light does not play a role.

The term "avidin material" includes avidin and related molecules such as streptavidin.

I. Overview

One aspect of the invention described herein relates to development of a new generation of sensitive microarray for high-throughput screening of various proteins including cancer biomarkers, cytokines and autoantibodies over a large concentration span, utilizing gold enhanced NIR-fluorescence of fluorophore labels on plasmonic Au films formed on glass. A platform is based on developing optimal gold coating on glass that can afford ~100 fold fluorescence enhancement for a set of NIR fluorophores for arrayed assays. Novel chemistry on Au is developed for immobilization of biomolecules such as proteins including antibodies as probes on plasmonic substrate. Applying the microarrays on Au, we can simultaneously measure large numbers of low abundance proteins including cancer biomarkers and cytokines with down to femto molar sensitivity. The new microarray platform can be used to screen the protein profiles in the sera of cancer and autoimmune diseases for research and potential clinical applications. The platform can also be used to develop the first multi-color microarray platform for simultaneously detecting different classes of proteins in the same array. The new microarray assay on gold films is more sensitive and specific for disease diagnosis at low costs of time, labor, reagent and samples than existing ELISA, RIA and microarrays on glass or nitrocellulose.

The present methods and materials employ solution phase growth of plasmonic Au films in a method that begins with rapid, in situ "seeding" of gold nanoparticles by deposition/precipitation of $Au^{3+}$ ions onto unmodified surfaces, followed by solution-phase reduction of the ions to $Au^0$. Subsequently, the gold seeds are "grown" into a film by the hydroxylamine reduction of $HAuCl_4$,[18] and the resulting films are referred to as gold-on-gold (Au/Au) films. Essentially, there is described a three step process in the preparation of the present nanoscopic ("Au/Au") films:

(1) seeding of gold onto a substrate by precipitation out of solution of Au3+ ions. The ions are precipitated from HAuCl$_4$ by raising its pH with a nitrogenous base, such as with NH4OH, urea, etc;

(2) reducing the ions precipitated in step (1) to Au$^0$ clusters on the substrate by a reducing agent such as NaBH$_4$, heat or H$_2$; and (3) growing seeds from step (2) by selectively adding gold to the initial seeds by reduction of an Au$^{3+}$ halide in a second solution to form "islands." This can be done by a reducing agent such as hydroxylamine. The additional gold in step (3) only attaches to the previously deposited seeds, leading to the present so-called "Au/Au" or gold-on-gold construction.

The initial seeding (precipitation) step can be carried out on a variety of substrates by immersing the substrate in the ionic gold solution. The substrate does not need to but can be pretreated in any way to increase gold adhesion. The ionic concentration of the gold salt is selected to control the size and spacing of the "seeds." The final size of and distance between islands will control the NIR-FE properties of the substrate and can be optimized to maximize NIR-FE. As described below, near-infrared fluorescence from an infrared fluorophore (IRDye800) was increased 100 fold by controlling the nanoisland size to be on the order of hundreds of nanometers spaced at several to tens of nanometer gaps.

The present methods and materials also comprise assays, such as bioassays, based or SERS, NIR-FE, or other plasmonic activity of the Au films. The present Au/Au (gold on gold) plasmonic films are described, and subsequently optimized for the preparation of a number of assays as described in Sections I-III.

The NIR-FE described below relates to enhanced fluorescence in the NIR range, 600-2000 nm including the NIR-II range of 1000-2000 nm. NIR-II fluorophores are coupled to the present plasmonic surfaces in assay formats such as described below.

NIR-FE is achieved here by design of the gold isolated island areas with sizes and gaps that enhance the local excitation of electric fields, thus enhancing excitation. The plasmonic modes in the gold islands are also tuned to couple resonantly to the emission dipoles of the fluorophores, leading to enhanced radiative decay and thus increased fluorescent quantum yield. Fluorescence enhancement by ~100-fold or even greater can be achieved. The plasmonic resonance wavelengths of the gold film were tunable by the precipitation, seeding and nanoisland growth parameters and can span from ~500 nm to ~2 µm, which overlaps with the excitation and emission energies of many NIR fluorophores. Due to the enhanced excitation electric fields by nanogaps and resonant fluorophore emission coupling to the plasmonic modes, the fluorescence of several NIR agents on top of the gold film was physically enhanced by ~15- to 100-fold or higher for several fluorophores, including Cy5 and IRdye-800. The present AuAu methods produce random gold isolated island areas at ~10-100 nm nano-gap spacing, and plasmonic peaks in the 525-1400 nm range useful for NIR fluorescence enhancement. Regular arrays of gold isolated island areas can be made by lithographic patterning to achieve even higher NIR-FE Au films are known to exhibit plasmon resonances at longer wavelengths than silver (Ag) due to higher dielectric constants. Gold films will afford at least NIR-FE of at least 2-fluorophores or 2-colors with non-overlapping emission in the 700-900 nm emission range. For the short wavelength emitting dyes such as Cy3, films with mixed Ag and Au nanostructures on a substrate may be prepared, in self-assembled arrangement or by lithographic patterning techniques. It is possible to pattern Ag and Au in regular arrays at designed locations for making Ag/Au plasmonic films on glass for fluorescence enhancement in a wide spectral range of 500-1000 nm, or even from the 1000-200 nm NIR-II range.

The present assays can be highly multiplexed by depositing on the substrate different antigens or other types of capture agents such as antibodies, peptides, cytokines, nucleic acids and whole cells. It can enable multiplexed detection of up to hundreds or thousands of cytokines (and other proteins) in an array with down to 0.01 pg/mL (~1-10 fM) minimum detectable concentration, by using a sandwich assay format. Different fluorophores with non-overlapping emission wavelengths can be used in the same assay to label different classes of proteins or antibodies to achieve multi-color differentiation of protein or antibody subtypes such as IgG, IgM, or IgA in the same assay.

For instance, an Au-film for enhancing IRDye800 with a ~100-fold fluorescence enhancement (emission ~800 nm) relative to arrays prepared on glass has been prepared. The same Au film enhanced Cy5 by ~15 fold. At least 3 dyes (e.g., Cy3, Cy5, and IRDye800) can be identified to have little overlap in emission spectra. This can be utilized to build multi-color microarrays for the first time capable of measuring different sub-types of proteins with low and high abundances in human serum, with the maximally enhanced fluorophore for reporting the least abundant molecule.

Figure 10:
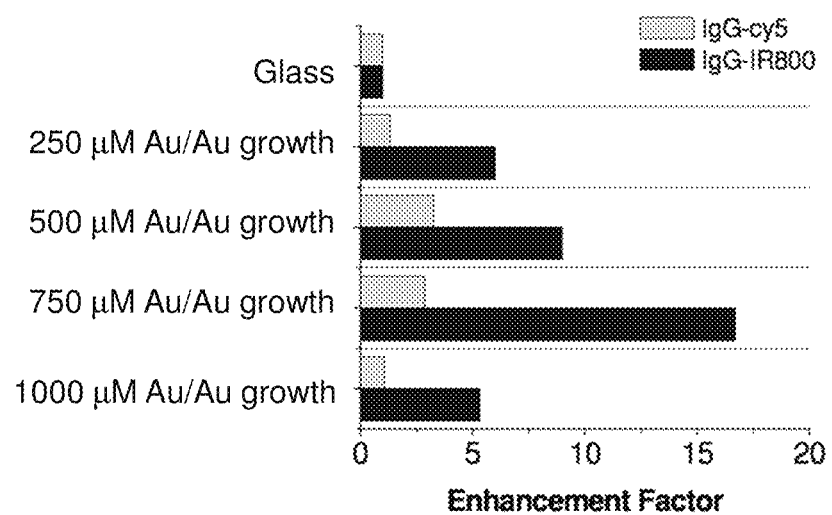
FIG. 10 is a diagram showing calculated enhancement factors of Au/Au films relative to the glass sample when Au/Au film was used to maximize fluorescence enhancement of Cy5 and IR800.
Figure 11:
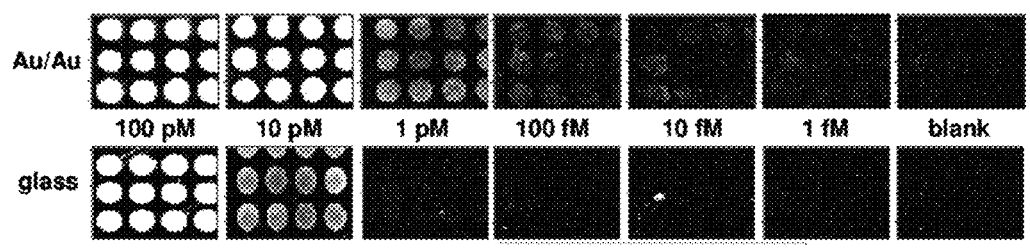
FIG. 11 shows the comparison of fluorescence maps generated on a Near-infrared fluorescence enhanced protein microarrays (μArray/Au) versus generated on a glass substrate. Top panel: μArray/Au fluorescence maps generated by integration of goat anti-rabbit IgG-Cy5 fluorescence emission at 633 nm excitation for different concentrations (12 duplicate spots for each concentration) of the analyte, carcinoembryonic antigen (CEA) spiked into whole, undiluted serum. Lower panel: fluorescence maps on the same intensity scale as the top panel for comparison, generated in an identical fashion on a glass substrate.
Figure 12:
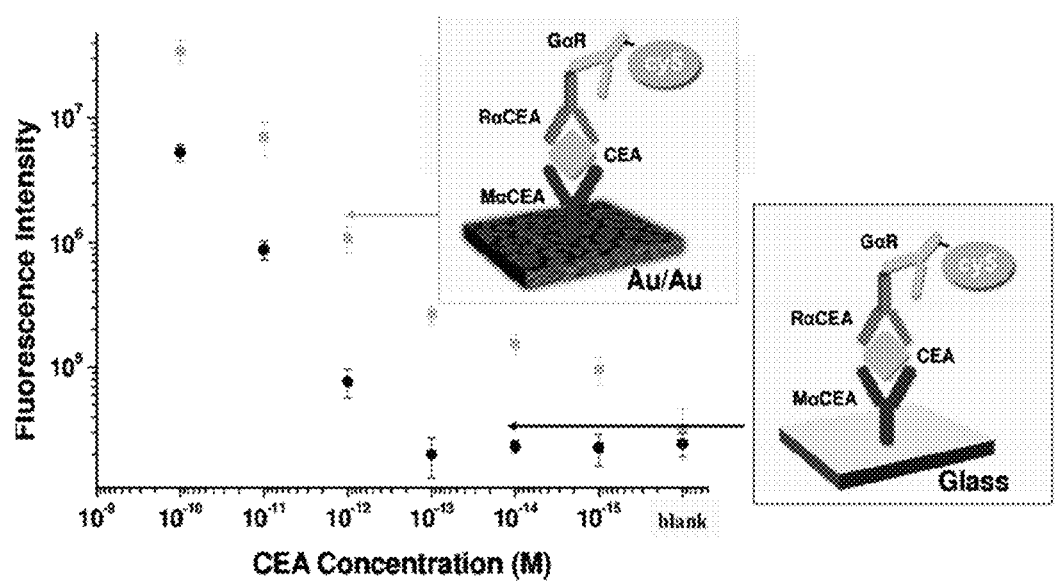
FIG. 12 shows calibration curves for CEA quantification were generated by averaging the integrated fluorescence intensity of goat anti-rabbit IgGCy5 emission over the twelve duplicate microarray spots for each CEA concentration on a μArray/Au assay as well as a protein microarray on glass as shown in schematics.

As noted, the structure of the AuAu films are controlled for plasmonic properties. This is illustrated in FIG. 10. As shown there, the optimal conditions for near-infrared fluorescence enhancement of near-infrared fluorophores were 3 mM HAuCl$_4$ during seeding and 750 uM HAuCl$_4$/NH$_2$OH during growth. As another, comparative example, one could use, as in the Hong et al. JACS paper, 3 mM HAuCl$_4$ for seeding and 3 mM HAuCl$_4$/NH$_2$OH for growth, but this produces a thick gold, and continuous film that is favored for NIR-FE in the long wavelength 1000-2000 nm NIR-II region. On the other hand, the conditions for optimal surface-enhanced Raman scattering are different (3 to 5 mM HAuCl4 for seeding and 1 mM HAuCl4/NH2OH during growth). It's expected that there will be different optimal gold film conditions for different applications such as enhanced fluorescence or SERS because the mechanisms of these phenomena are different. The optimal conditions for microarray applications based on NIR fluorophores like Cy5 or IR800 would be around 3 mM HACl$_4$ for seeding and 750 µM HAuCl$_4$ for growth. While variations in experimental conditions could lead to different metal film nanostructures, the desired gold nanostructure for optimal NIR-FE is as described above, containing abundant nanogaps for electrical field enhancement and gold surface plasmons in resonance with the NIR fluorophores.

The present description is organized as follows:

Section I (examples 1-5): an immunoassay, using the present nanoscopic gold film in a surface-enhanced Raman Scattering (SERS) substrate;

Section II (examples 6-13): an NIR-fluorescence metal-enhanced assay where a capture molecule is attached to the present nanoscopic gold film and its binding labeled with an NIR dye in a sandwich assay format; and Section III (examples 14-17): imaging of live cells on the present nanoscopic gold film, where the substrate produces NIR-FE fluorescence in the NIR range.

Section I. Solution Phase Method Gold Film Deposition for SERS-Based Immunoassay (FIGS. 1-5), Examples 1-5

These examples pertain to the preparation of the solution phase gold films. Briefly, gold-on-gold (Au/Au) substrates were produced in the following general manner. The substrate of choice was submersed in a solution of chloroauric acid, to which ammonium hydroxide was added at 20 μL/mL (0.6% ammonia), under vigorous agitation for one minute. Following incubation in the seeding solution, the substrate was washed by sequential immersion into two water baths. Immediately following the wash steps, the $Au^{3+}$ seeded substrate was submersed into a solution of 1 mM sodium borohydride at room temp on an orbital shaker or agitated manually. Reduction was allowed to proceed for 1-5 minutes, followed by two submersions of the substrate in water baths. Au nanoparticle-seeded substrates were moved directly from wash water baths to a 1:1 (by concentration) solution of $HAuCl_4$ and $NH_2OH$ under vigorous agitation to initiate growth. Growth proceeded at room temperature on an orbital shaker at 100 RPM or under manual agitation until obvious development of the film ceased, 15-20 minutes. The Au/Au film was deposited on a bioassay substrate, as shown in FIG. 4, where an inert substrate (glass slide) was printed with an antibody (mouse anti-CEA) in discrete spots; exposed to a sample containing antigen (CEA); exposed to a capture antibody (rabbit anti-CEA); and exposed to a detection antibody labeled with a Raman label (anti-rabbit antibody conjugated to a nanotube (single walled carbon nanotube). This multilayered array was then coated with the Au/Au gold film, and the binding of detection antibody was measured by Raman scattering using a Raman spectrometer.

Thus there is represented in these examples a completely solution phase, seed-based approach, capable of producing plasmonic gold films, for both surface-enhanced Raman scattering (SERS) and NIR fluorescence enhancement (NIR-FE) applications, on a variety of substrates, without requiring pre-existing surface modification or functionalization. SERS enhancement factors of $\sim 10^7$ were observed. Moreover, solution-phase gold film deposition on highly complex surfaces, such as protein-coated bioassays, is demonstrated. Protein bioassays coated with such SERS-active gold films were combined, for example, with bioconjugated single-walled carbon nanotube Raman labels, affording high sensitivity detection of the cancer biomarker, carcinoembryonic antigen in serum, with a limit of detection of ~5 fM (1 pg/mL).

The in situ Au seeding step is a critical step in to the entire Au/Au film synthesis process. This step controls the initial density (seeds/mm$^2$) and size of the seeds first deposited on the substrate. It was hypothesized that the addition of ammonium hydroxide to chloroauric acid in basic pH leads to ligand exchange of chloride for ammine (or amino) ligands around the $Au^{3+}$ center, with a general form $Au(NH_3)_2(H_2O)_{2-x}(OH)_x^{(3-x)}$.[22] The resulting amine-gold complexes do not rapidly hydrolyze in basic solutions[23] and aggregate into clusters. In moderately basic pH, the low-solubility, cationic clusters are then deposited onto negatively charged substrate surfaces. The deposited gold precipitates are subsequently reduced into $Au^0$ nanoparticles by sodium borohydride in aqueous solution (step (2) above). The Au nanoparticle seeding methodology presented here appears to be very broadly applicable to a variety of substrates. Unlike previous reports of solution-phase gold film growth, the present method is not restricted to surfaces bearing amino- or mercapto-functionality[18, 19].

Gold cluster seeding density was varied to obtain conditions that yielded uniform and dense seed distribution. Seeding density increased with increasing $Au^{3+}$ concentration (FIG. 2A-2C), thus allowing one to control the film density and morphology. Seeding of cationic Au clusters was also found to be dependent on pH, resulting in a uniform seed layer only at pH 8-10. Replacement of ammonium hydroxide with sodium hydroxide in the seeding step led to colorless cationic Au solutions and failed to produce Au NP seeding, thus exemplifying the role of nitrogen-containing basic ligands in the precipitation and deposition process. Direct seeding of $Au^0$ nanoparticles by addition of sodium borohydride to a solution of $HAuCl_4$ containing a substrate (e.g. glass slide) also led to formation of Au NPs on the substrate surface, but subsequent $Au^{3+}$ reduction by hydroxylamine produced a non-uniform, and thus undesirable, plasmonic film.

Reduction of the deposited small clusters of gold cations by $NaBH_4$ was necessary prior to the "growth" of the final Au/Au film, without which, no reduction of $Au^{3+}$ by hydroxylamine was observed. Following reduction of the seeds, AFM confirmed the presence of nanoscopic spheres with heights 5-10 nm (FIG. 1B), and absorbance spectroscopy revealed a plasmon resonance at 525 nm confirming conversion of the cationic clusters to nanoscale $Au^0$ particles.

Growth of the Au film occurred by hydroxylamine reduction of additional chloroauric acid onto the "seeds." The rate of $HAuCl_4$ reduction by hydroxylamine is much greater for surface-bound $Au^{3+}$ ions than those in solution, and thus $Au^0$ formation is specific to the seed layer.[18] Optimal synthesis conditions for SERS-active Au/Au films were identified by independently varying the $Au^{3+}$ concentrations during both seeding and growth (FIG. 3). The $Au^{3+}$ concentration during growth had a profound effect on the resulting plasmon peak and particle morphology (FIG. 3). The heights of the Au/Au isolated island areas, comprising the overall film thickness, were also dependent upon the concentration of $HAuCl_4$ employed during growth, yielding heights ranging from 10 to 200 nm, where isolated island areas of 30-100 nm in height (from the substrate) were found to maximize NIR-FE. Morphology of the Au/Au films imaged by SEM shows individualized Au nanoparticles at low concentrations, growing into isolated island areas at higher concentrations, and finally forming a continuous rough gold film at very high $Au^{3+}$ concentrations. Growth in the lateral dimension of the Au isolated island areas proceeds faster than growth away from the surface (height) as a result of the fusion of neighboring isolated island areas during growth.

The ability to chemically control gold nanoparticle island sizes, as well as inter-particle spacing, is key to optimizing the ensemble surface plasmon of the resulting film for SERS and NIR-FE applications. Gold nanoparticle seed density, controlled by the $HAuCl_4$ concentration during precipitation/deposition, and the final island size, controlled by both the seed density as well as the concentration of $Au^{3+}$ ions present during the film growth step, allow relatively precise control over inter-island gap spacing. The coupling of proximal plasmonic gold nanoparticle isolated island areas is likely to be a key parameter determining both the energy of the ensemble plasmon resonance, and the magnitude of the local electric field enhancement, and thus SERS effect, provided by the film.

The synthetic conditions may be varied systematically to afford a library of plasmonic substrates. The density of Au seeds will be varied by the concentration of the initial chloroauric acid. The concentration of Au3+ ions during the second step of hydroxylamine-mediated growth will determine the nanogap distance between the Au nanoislands, ranging from isolated small isolated island areas to islands with 5-10 nm gaps, and to continuous rough films without any gaps. At low growth concentration of HAuCl4, a substrate seeded at low density will not produce a network of interacting plasmonic gold structures with a plasmon resonance at ~525 nm, typical of non-interacting Au nanoparticles. Under identical growth conditions, a substrate seeded at increasingly higher density of Au seeds will yield network of interacting plasmonic nano-islands, with progressively red-shifted plasmon resonance all the way to the NIR up to ~1500 nm. This simple solution phase synthesis will produce a library of plasmonic (visible-NIR) Au substrates with ~10-100 nm nano-gap spacing, and plasmonic peaks in the 525-1400 nm range useful for fluorescence enhancement in the broad visible-NIR range.

Although the present solution-phase method of making Au isolated island areas is advantageous, other methods may be employed to arrive at isolated island areas with the properties of size and spacing as described herein. For example, plasmonic substrates can be based on chemical synthesis of Au nanoplates (e.g., single crystal nano-triangles, -hexagons, etc) on substrates or in solution phase. Once regularly shaped and sized Au nanoplates are synthesized as a uniform suspension in solution, the Au nanoplates can be functionalized with thiol molecules and then one can perform self-assembly and/or Langmuir Bloddget assembly to form monolayers of closely packed films of gold-nanoplates. The chain length of the thiol molecules will be used as a natural spacer between the plates for controlling the gap distance between the plates, thus controlling the electric field enhancement factor and the plasmonic coupling between plates. One may synthesize Au nanoplates using established methods by reducing Au ions on pre-formed Au nanoparticle seeds under conditions that promote the anisotropic growth of Au.

Alternatively, patterning methods may be used to produce plasmonic Au substrates containing regularly spaced Au nanostructures with more controlled sizes, which could provide further enhancement effects. In particular, nanosphere lithography, block-copolymer lithography as well as semiconductor lithographic patterning methods can be employed o generate plasmonic gold-films that can give the maximal fluorescence enhancement of fluorophores. Nanosphere lithography and block-copolymer templates based lithography could produce Au nanostructures with various gaps between Au particles or isolated island areas.

Optimal synthesis conditions for SERS-active Au/Au films were identified by independently varying the $Au^{3+}$ concentrations during both seeding and growth (FIG. 3), with a self-assembled monolayer (SAM) of benzenethiol employed as the Raman-reporter. Au/Au film SERS enhancement factors of $10^6$-$10^7$ were observed for benzenethiol (at 785 nm excitation) chemisorbed onto Au/Au films grown on unfunctionalized glass and polymeric substrates (FIG. 3), in good agreement with expected values.[10, 17, 24, 25] SERS enhancement factors increased with increasingly red-shifted plasmons and increasing film thickness up to a point, followed by a rapid drop in enhancement factor, resulting from complete coalescence of the gold film under very high concentration $Au^{3+}$ growth condition. This behavior is consistent with previous reports that have suggested that maximal SERS may be obtained within in the gaps between separated plasmonic particles, owing to vastly increased electric fields resulting from coupled localized surface plasmons.[26, 27] Thus, for Au/Au films, employed in SERS assays and grown onto glass substrates, the optimal $HAuCl_4$ concentration for seeding was found to be 5 mM, while the optimal $HAuCl_4$ concentration during the growth step was 1 mM.

Beyond unmodified inorganic and polymeric substrates, the broad applicability of Au NP seeding by precipitation was tested by depositing Au precursor seeds onto a protein bioassay in order to obtain a SERS effect of underlying SWNT Raman labels.[7, 28-30] Precipitation and deposition of cationic gold clusters onto the protein-coated assay slide was successful, as evidenced by a uniform color change upon reduction of the gold seeds to $Au^0$. It is plausible that proteins on the bioassay surface contained negatively charged domains or functional groups that promote seeding of $Au^{3+}$ clusters. Growth of the Au seeds by hydroxylamine-mediated $Au^{3+}$ reduction led to uniform Au/Au film growth and enhanced the Raman scattering intensity of the SWNT labels by 250-fold. (FIG. 5). The improved signal-to-noise ratio of surface-enhanced SWNT Raman-label scattering afforded detection of the protein biomarker carcinoembryonic antigen (CEA) in serum at concentrations as low as 5 fM (1 pg/mL). To our knowledge, this is the first time that plasmonic film substrates were formed atop protein microarrays by solution phase chemistry.

Precipitation of cationic Au by ammonium hydroxide is shown here to be a powerful and general method to generate uniform Au NP seeds onto a wide variety of unmodified or complex substrates that can be coupled with selective reduction of $Au^{3+}$ by hydroxylamine, Au/Au films optimized for surface-enhanced Raman scattering have been generated on unfunctionalized glass, quartz, and $SiO_2$, as well as on polymeric, flexible substrates such as poly(vinyl chloride) and poly(dimethylsiloxane).

Section II. Nanostructured Gold Films Used as Plasmonic Substrates for Multiplexed Microarray Assays Using NIR Labels and NIR-FE (FIGS. 6-13, FIGS. 17-18), Examples 6-13

These examples pertain to protein microarrays prepared on a similar nanostructured, plasmonic gold film to that described in Section I, optimized to provide, rather than a surface-enhanced Raman scattering effect, near-infrared fluorescence enhancement, of up to 100-fold, extending the dynamic range of protein detection by three orders of magnitude towards the fM regime. This is termed NIR fluorescence enhancement (NIR-FE). NIR-FE is a physical phenomenon similar to surface enhanced Raman scattering (SERS) but remains much less well known or studied than SERS for biology and medicine.

Plasmonic protein microarrays are demonstrated for use in early detection of a cancer biomarker, carcinoembryonic antigen, in the sera of mice bearing a xenograft tumor model. Further exemplified is a multiplexed autoantigen array for human autoantibodies implicated in a range of autoimmune diseases with superior signal-to-noise ratios and broader dynamic range compared to commercial nitrocellulose and glass substrates. Further exemplified is a cytokine assay on a plasmonic gold substrate, which uses microarray printing onto NHS-activated gold slides of anti-cytokine antibodies. The high sensitivity, broad dynamic range and easy adaptability of plasmonic protein chips present new opportunities in proteomic research and diagnostics applications.

To date, fluorescence enhanced multiplexed microarray assays have not been demonstrated, and sensitive and quantitative measurements of disease biomarkers have been hampered by the inability to produce fluorescence-enhancing substrates that are uniform over large areas and stable over time.

The present protein microarrays on plasmonic gold substrates enable multiplexed protein assays affording detection limits as low as a few fM, with six orders of magnitude dynamic range. A nanostructured gold film prepared by uniform, solution-phase growth onto whole glass slides affords near-infrared fluorescence enhancement (NIR-FE) of up to 100-fold, useful for significant improvement of protein microarray detection assays. The resulting microarray substrates (μArray/Au) are compatible with standard microarray scanners and afford highly sensitive measurements over a broad dynamic. Compared to standard glass-supported microarrays, the present arrays afford an expansion of dynamic range of protein microarrays by up to three orders of magnitude. In these examples, The femtomolar detection limit and broad dynamic range allow for quantification and monitoring of CEA in serum samples of mice during the early-stage growth of xenograft LS174T tumors, opening the possibility of NIR-FE protein microarrays for early disease detection and therapeutic monitoring. Finally, the broadened dynamic range afforded by the present array is employed for multiplexed detection of human autoantibodies, demonstrating the potential for NIR-FE protein microarrays to serve not only as sensitive diagnostic assays, but also as tools to expand the capabilities of proteomic research into the pathogenesis and pathophysiology of disease states.

The present simple and scalable solution-phase growth methodology affords uniform, plasmonic, nanostructured gold films on glass slides, capable of intensifying the emission of near-infrared fluorophores. Fluorescence enhancement is found to be dependent upon plasmon resonance, gold film structure, and the fluorophores used to probe the fluorescence enhancement phenomenon. Employment of μArray/Au assays for quantification of protein biomarkers results in significantly improved detection limits and broader dynamic ranges than traditional protein microarrays and ELISA. Moreover, multiplexed protein microarrays performed on μArray/Au benefit from enhanced feature intensity and low autofluorescence background, compared to commercially available glass and nitrocellulose substrates, thus providing a broader dynamic range with increased sensitivity for protein microarrays.

Figure 8:
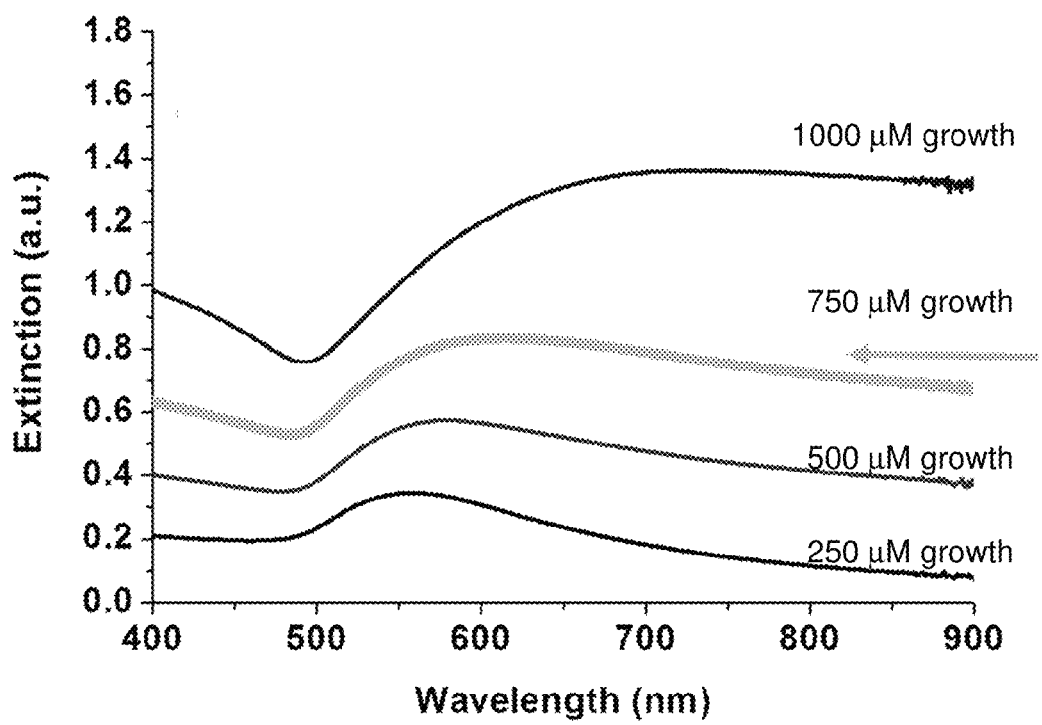
FIG. 8 is a graph showing the extinction spectra of Au/Au films. Increased growth concentrations of $HAuCl_4$ and $NH_2OH$ lead to increasing extinction and monotonically red-shifted plasmon resonance. Arrow indicates Au/Au film growth condition used for µArray/Au assays.

Excitation field enhancement, resulting in an increased optical transition rate, is believed to be a contributing factor to our observations of NIR-FE. Synthesis conditions of plasmonic gold films providing optimal fluorescence enhancement for two commercially available and often used fluorophores, Cy5 and IR800, were identified by systematically varying the $HAuCl_4$ and $NH_2OH$ concentrations during seeding and growth of the Au/Au film (FIG. 10). In comparison with emission of these fluorophores from a bare glass slide, maximal relative fluorescence enhancement was observed with a seeding concentration of $HAuCl_4$ of 3-5 mM and $HAuCl_4$ and $NH_2OH$ concentrations between 0.5 and 1 mM during the growth step. Under these conditions, the gold nanoisolated island areas form a dense, yet noncontinuous film (FIG. 9), with strong inter-particle plasmonic coupling (described in Section I), resulting in high scattering efficiency for wavelengths from about 550 nm into the near-infrared (FIG. 8). As described in the examples, optimal NIR-FE is provided by Au/Au films containing dense gold isolated island areas with an average inter-island gap distance of ~36 nm, optimally between about 13 and 59 nm, or between 10 and 60 nm. On the other hand, thick Au/Au films containing a semi-continuous layer of gold (few gaps present) yielded little fluorescence enhancement relative to a bare glass substrate, while completely continuous gold films (no gaps present) resulted in quenching of fluorescence. We therefore attribute the nanoscale gaps in our Au/Au films, and the resulting enhanced excitation electric fields, as one of the causes of fluorescence enhancement on our μArray/Au platform (see Corrigan, T., Guo, S., Phaneuf, R. & Szmacinski, H. Enhanced Fluorescence from Periodic Arrays of Silver Nanoparticles. *Journal of Fluorescence* 15, 777 (2005)).

Proximity of a fluorophore to a metal structure could quench fluorescence emission due to a greater enhancement of the non-radiative decay rate $k_{nr}$ than the radiative decay rate $k_{rad}$. Fluorophore coupling to the scattering component of plasmonic extinction is responsible for increased radiative decay rates resulting in fluorescence enhancement, while the absorption component is responsible for enhancing the rate of non-radiative decay and thus, fluorescence quenching. The magnitude of absorption and scattering components of the optical spectra of metal nanoparticles depends on both the size and shape of the metal structures, as described by Mie theory. Significantly increased non-radiative decay rates could be the cause of fluorescence quenching, rather than enhancement, on continuous films. The NIR fluorophore should be spaced from the gold to prevent quenching. In the case of a sandwich assay, described here, the spacing will result from intermediate layers of proteins between the fluorophore-bearing molecule and the substrate. For example, the labeled protein may be a secondary antibody bound to a detection antibody, bound to an antigen, bound to a capture antibody on the substrate. Because of the many layers of proteins involved, the fluorophore is positioned 10's of nm away from the surface. For direct measurements of fluorescence enhancement, protein-fluorophore conjugates were drop-dried onto the film, such that the fluorophores likely have displacement from film surface of at least a few nm (due to the size of the protein).

The scattering (re-radiating) efficiency of the present Au/Au film for fluorescence enhancement is large in the near-infrared where the plasmonic peaks of the Au/Au films overlap with the fluorescence emission wavelengths of the IR800 and Cy5 fluorophores. The plasmonic resonance peaks of the present Au/Au films reside in this NIR region due to the wavelength-dependent dielectric constant of gold, suitable sizes of the gold isolated island areas, and possibly the elongated shapes of the isolated island areas in the Au/Au films. We attribute NIR-FE of IR800 and Cy5 labels in our μArray/Au to the optimal gold island size (on the order of $10^4$ $nm^2$ optimum range) and the coupling of the dipolar components of the plasmonic modes of these nanoislands to the emission of fluorescence. The suitable Au isolated island areas sizes and plasmonic coupling in these nanostructured Au/Au films may have led to an increase in $k_{rad}$ that outweighed $k_{nr}$ enhancement of the near-infrared fluorophores used herein for microarray protein assays, contributing to an increased apparent quantum yield and improved signal-to-noise ratios for protein detection. Additional research into the effect of our nanostructured Au/Au film on radiative and non-radiative decay rates of IR800 and Cy5 is underway.

The observed variation in enhancement factor between Cy5 and IR800 on a given Au/Au film is likely due several contributing factors. First, because the observed quantum yield scales with the ratio of radiative decay rate to total decay rate, the radiative decay rate could be enhanced relatively more than the non-radiative decay rate for inherently low quantum yield emitters[12] (η~7% for IR800 vs. ~20% for Cy5). Also, the different excitation and emission energies of the fluorophores may interact differently with absorbance and scattering components of an Au/Au film with fixed plasmon resonance. It is presumed that only the scattering component of metal nanoparticles contributes to far field radiation, which is greater at longer wavelengths, such as those characteristic of IR800. Finally, the incident field enhancement efficiency of metal nanostructures is dependent upon both nanoparticle spacing as well as wavelength. Peak field enhancements are obtained at longer wavelengths when nanoparticle separation distances are small.

Combined with the benefit of low biological autofluorescence in the near-infrared excitation/emission region and increased surface area, the improved signal-to-noise ratios of μArray/Au assays provide improved sensitivity for quantification of disease biomarkers in biological media. Unlike chemical amplification methods, metal-enhancement of NIR fluorescence emission increases signal without creating undesirable background or additional noise. μArray/Au assays afford increased signal-to-noise ratios by ~15-fold for Cy5-labeled sandwich assays and ~100-fold for IR800-labeled sandwich assays relative to identical protein microarray sandwich assays on glass slides. For detection and quantification of CEA spiked into 100% serum, such gains in signal-to-noise resulted in improved detection limits to 5 fM with a dynamic range over six orders of magnitude.

As described in the examples below, detection of CEA in the serum of xenograft mouse models bearing LS174T tumors was accomplished by use of μArray/Au assays. In comparison to a calibration curve, serum CEA concentrations in the range of ~30 fM to 100 fM were detectable when tumor volumes were well below 100 mm³. With detection limits in the range of 1-5 pM, commercially available CEA ELISA kits fail to provide adequate sensitivity to detect or quantify CEA in the majority of the ex vivo serum samples analyzed in the present study. Moreover, protein diagnostics based upon highly sensitive μArray/Au assays require far less sample volume than ELISA and may be multiplexed to analyze a variety of protein biomarkers at once.

Also, to demonstrate the multiplexing capabilities of μArray/Au substrates, a panel of human autoantigens was printed onto μArray/Au substrates, as well as commercially available nitrocellulose membrane substrates and glass slides. The autoantigens printed represent both well characterized and poorly characterized targets of human autoantibodies implicated in a range of autoimmune diseases including systemic lupus erythematosus (SLE), Sjögren syndrome, mixed connective tissue disease, systemic sclerosis, celiac disease, Goodpasture syndrome, and others. Incubation of a mixture of human sera as described below containing known reactivity towards several autoantigen targets led to the observation of a broad range of reactivities, represented as microarray feature intensities, with which the various assay substrates could be compared and contrasted.

Nitrocellulose-based substrates were often used for protein microarrays because they provide a high surface area, 11 μm thick, three dimensional polymer layer for capture reagent immobilization, with a protein binding capacity[34] of ~4000 ng/mm³. In contrast, planar surfaces, such as μArray/Au and glass, provide binding capacities in the range of 10-100 ng/mm². Therefore, protein microarrays, such as autoantigen arrays, on nitrocellulose membranes yield high feature intensities through increased capture efficiency (vide supra). On the other hand, nitrocellulose films are known to exhibit high autofluorescence in the visible, limiting their dynamic range and utility. Autofluorescence of nitrocellulose is mitigated to an extent by employing fluorescence excitation and emission energies in the near-infrared (e.g. Cy5 and IR800 dyes), however we have observed that sufficient background intensity remains, even at emission wavelengths from 700-800 nm emission (FIG. 7), to prevent identification of dilute or low reactivity autoantibodies. The dynamic range of this IR800-labeled autoantigen array on nitrocellulose was half an order of magnitude, while the background intensity and maximum observed feature intensity of an autoantigen array labeled by Cy5 differed only by a factor of 2.

In contrast, μArray/Au substrates afford higher positive signals due to fluorescence enhancement as well as 10-fold lower autofluorescence backgrounds compared to nitrocellulose. With a much broader fluorescence intensity range (~2 orders of magnitude) than nitrocellulose (~half of an order of magnitude) in this multiplexed autoantigen array, μArray/Au substrates identified not only the highly reactive autoantibodies in the serum mixture, but also other autoantigen features with non-negligible reactivity towards the autoantibody-containing serum. μArray/Au also outperformed planar glass substrates, with vastly increased positive intensities and higher signal-to-noise ratios owing to NIR-FE.

All assay substrates exhibited positive feature intensities for highly reactive markers of autoimmune conditions such as Lupus (e.g. systemic lupus erythematosus, SLE, and subacute cutaneous lupus erythematosus, SCLE), Sjögren Syndrome, systemic sclerosis, poly- and dermato-myositis, and thyroiditis. The sample of mixed autoimmune serum employed here included well characterized autoantibodies targeting Ro/SS-A, Jo-1, centromere protein B, thyroglobulin, and DNA topoisomerase-1 (scl-70), all of which were detected with high intensity as expected on their conjugate antigen feature (see Table 1 in Example 11). The serum sample also contains autoantibodies towards myeloperoxidase, proteinase 3, histones, and mitochondrial antigen, where were not included in the autoantigen array. Moreover, it is expected that the serum mixture also includes uncharacterized autoantibodies and other human immunoglobulin Gs which may contribute to intermediate and low levels of array feature intensity. For example, non-negligible intensity was observed on both nitrocellulose and μArray/Au representing reactivity of the serum mixture towards thyroperoxidase, Sm protein B/B', measles antigen, glomerular basement membrane (GBM) antigen, complement complex C1q, and components of the U1-snRNP complex (e.g. U1-C, U1-A, sm/RNP).

Autoantibodies of PCNA (proliferating cell nuclear antigen, further described in Int J Radiat Biol. 2001 October; 77(10):1007-2), implicated in SLE (systemic lupus erythematosus), were not observed on any of the substrates tested. However, the μArray/Au substrate revealed slight reactivity, not known a priori, of the incubated autoimmune sera towards autoantigens including double stranded DNA, PL-12, and PM/Scl-75, which, on nitrocellulose, did not present feature intensity of significant difference from the background. These antigens are implicated in autoimmune disorders such as SLE, polymyositis, and polymyositis-systemic sclerosis overlap syndrome respectively. This shows that in addition to improved detection limits for protein-based diagnostics (e.g. early cancer detection), μArray/Au protein assays could significantly enhance our ability to elucidate intermediate and low level autoantibody reactivity in autoimmune diseases. In general, the higher sensitivity and broader dynamic range afforded by μArray/Au substrates will benefit high-throughput proteomics research, as well as diagnostics, for a wide range of diseases throughout various biological fields.

Using the multiplexed cytokine detection protocol illustrated in FIG. 17, sensitive detection of cytokines was demonstrated. The present micro-array is prepared with a plasmonic gold film on a glass or other inert substrate. A plasmonic gold film was attached to a glass substrate. A glass substrate as shown in FIG. 17A. Antigens of choice are printed on the substrate, e.g. insulin, GAD65, ICA 512 membrane protein, islet cell autoantigens such as IA-2, etc. The antigens are incubated with plasma or serum from a subject, then labeled secondary antibodies are added, which will bind to any human antibodies bound to the antigens. The labeled secondary antibodies may be, for example anti-human Fc antibodies. covalently conjugating 6-arm branched poly(ethylene glycol) (PEG)-amine polymer stars to a self-assembled monolayer of mercaptohexadecanoic acid on the gold surface Referring now to FIG. 17B, a capture antibody 1902 is attached to the slide. Antigen 1904 will bind to this antibody during the assay. The antigen is also bound to biotin conjugated detection antibody 1906, which in turn is bound by streptavidin-IRdye 1908.

Currently, enzyme-linked immunosorbent assay (ELISA) has been the gold standard for protein quantification with sensitivity down to pg/ml level[33-34]. However, ELISA requires relatively large sample volumes and cannot be used for multiplexed high-throughput screening. In addition, due to the vast library of cytokines and their low level in human serum, cytokine is near or below the detection limit for ELISA[35].

These disadvantages are overcome by cytokine detection on plasmonic gold films. The plasmonic, nanostructured gold films can afford fluorescence enhancement of near-infrared fluorophores, useful for vastly improving the sensitivity of microarray as says[36]. The emission of fluorophores positioned in proximity to plasmonic metal nanostructures can be enhanced due to amplified excitation electric fields between nanogaps, and increased radiative decay of excited states due to resonance coupling between surface plasmonic modes and fluorescent emission dipoles[37-39]. With up to 100-fold fluorescence enhancement, detection of a cancer biomarker, carcinoembryonic antigen has reached low femtomolar detection limit on plasmonic gold films[36].

We performed multiplexed cytokine detection on plasmonic gold substrates and focused on investigating the selectivity of detection. Capture antibodies (FIG. 17B, 1902 for VEGF, IL-1β, IL-4, IL-6, IFN-γ, and TNF were printed in a 6×8 spot matrix format with each row containing one type of capture antibody in replicates of 8 (FIG. 18). Following incubation of a single cytokine or a cocktail of mixed cytokines spiked into 10% FBS/PBS solution as analytes, a mixture of biotin conjugated detection antibodies for VEGF, IL-1β, IL-4, IL-6, IFN-γ and TNF were incubated on the cytokine chip. IRDye800-labeled streptavidin was then applied as the last layer for fluorescence labeling and detection.

The multiplexed protein microarray on a plasmonic gold substrate can be also applied to rapid identification of diabetes autoantibodies. The current standard for differentiating type 1 (autoimmune) from type 2 (and other non-autoimmune forms of diabetes) is to test for the presence of one or more diabetes autoantibodies. Exemplary antibodies are antibodies to IA2 (insuloma antigen 2), described, e.g. in Batstra et al., "Low prevalence of GAD and IA2 antibodies in schoolchildren from a village in the southwestern section of the Netherlands," Hum Immunol. 2001 October; 62(10): 1106-10, antibodies to ICA512 (islet cell autoantigen 512, described e.g. in Solimena et al., "ICA 512, an autoantigen of type I diabetes, is an intrinsic membrane protein of neurosecretory granules, EMBO J. 1996 May 1; 15(9): 2102-2114.), antibodies to GAD65 (glutamic acid decarboxylase-65, UNIPROT entry Q99259 or Q05329), antibodies to ZnT8 (zinc transporter 8, described e.g. in Eneeet al., "ZnT8 is a major CD8+ T cell-recognized autoantigen in pediatric type 1 diabetes," Diabetes. 2012 July; 61(7):1779-84. Epub 2012 May 14.

The present point-of-care microarray assays on plasmonic gold allows rapid, reliable, affordable, and multiplexed detection of diabetes autoantibodies diagnostic for type 1 etiology in symptomatic children and adults. A prototype has overcome previous commercial challenges of poor sensitivity, and will allow simultaneous testing for other human autoimmune diseases known to have increased prevalence in patients with type 1 diabetes. The present microarray assay technology will also provide screening to test the risk of developing diabetes in a person without symptoms of diabetes.

The present gold film ("μArray/Au") assays afford a significant improvement in signal-to-noise ratio, resulting in multiplexed microarray protein sandwich assays possessing a broad dynamic range and high sensitivity, with detection limits ~1000 to 5000-fold lower than traditional techniques, yet they require no additional assay steps and are compatible with standard protein microarray processing and equipment. The NIR-FE μArray/Au assays rely on physical principles, namely an enhancement in excitation field strength, reduction in excited state lifetime, and overall apparent increase in fluorescence quantum yield to significantly improve the signal-to-noise ratio over standard protein microarrays.

The solution phase, bottom-up growth procedure of Au/Au films for fluorescence enhancement applications is scalable, simple and fast. The Au/Au film substrates for NIR-FE applications are stable over time and in biological media, and moreover are uniform enough to provide quantitative analysis with a dynamic range of over 6 orders of magnitude. In addition to affording biomarker quantification at low concentrations, high-throughput screening methods may benefit from the expanded dynamic range afforded by multiplexed μArray/Au assays, where concentrations of analytes, as well as binding constants, may span a significant and unknown range. The present near-infrared fluorescence enhancement based upon Au/Au films may also find additional applications as an in vitro imaging tool. For example, fluorescent agents bound to the membrane of live cells have been enhanced by Au/Au films.[35] Coupled with the simplicity afforded by physical signal enhancement and compatibility with existing microarray tools, μArray/Au assays are expected to find broad use in disease diagnosis and protein biomarker discovery applications.

Near-infrared enhancement according to the present methods may also be carried out with NIR-II fluorescence agents such as quantum dots (QDs) and organic dyes (IR-26, IR-1051, IR-1061) with high, ~15% quantum yield. Tunable plasmonic modes in the Au films are achieved by designing the size and shape of the Au nanostructures as described below, resulting in resonant coupling to the emission dipoles of fluorophores to enhance fluorescence radiative decay.

The present microarrays may be formed as arrays using biological molecules that are one of proteins, peptides, antigens, antibodies, nucleic acids, polysaccharides, carbohydrates or biomolecules in whole cells. See, for examples on techniques employing carbohydrates, "Preparing carbohydrate microarrays and conjugated nanoparticles," US 2008/0220988. Multiple types of NIR labels can be used to detect the binding of an analyte to the biological molecule on the array. For example, suitable labels include IRDye 800® infrared dye, a fluorescent dibenzyl compound commercially available from LI-COR Biosciences, Cy7, Cy5, or other dyes with fluorescence emission between 600 nm and 2000 nm.

Section III. Plasmonic Gold Substrates Used to Perform NIR Fluorecence Enhanced Molecular Imaging of Cells (FIGS. 14-16), Examples 14-17

The following examples describe the use of the Au/Au films for the imaging of cells using near-infra red fluorescence. A common caveat of NIR fluorophores is the relatively low quantum yields compared to their counterparts (including organic dyes and quantum dots) with shorter emission wavelengths in the visible, which limits their imaging capabilities. For example, the IR800 dye (with a peak emission wavelength of 800 nm) exhibits a ~10% quantum yield, and the indocyanine green (ICG) dye exhibits only ~4.3% quantum yield at the emission wavelength of 805 nm.[22] In contrast, molecules fluorescing at shorter wavelengths typically exhibit much higher quantum yields (IR700~24% at 700 nm emission cyanine-5~30% at 660 nm emission; fluorescein ~91% at 521 nm emission). SWNTs exhibit quantum yield ranging from 0.1% to 3%, due to intrinsic low-energy excitons that are optically forbidden, and extrinsic quenchers such as metallic SWNTs in bundles and oxygen in acidic environment. To fully utilize the spectral advantages of NIR fluorophores, it is desirable to develop a general approach to enhancing the photoluminescence (PL) in the NIR, thus enhancing the biological imaging capability in this important spectral region.

The examples below demonstrate the Au/Au substrate as a platform for NIR fluorescence enhanced (NIR-FE) cellular imaging using both SWNT and organic fluorescent labels. We used SWNTs functionalized by the cyclic pentapeptide containing a arginine-glycine-aspartic acid sequence (RGD) to selectively tag U87-MG brain cancer cells over MCF-7 breast cancer cells, plated the cells on the Au/Au substrate, and observed a ~9-fold increase in SWNT fluorescence on U87-MG cells. This enabled high quality NIR molecular imaging of molecularly targeted cells using much shorter exposure times (~300 ms) than previously possible with nanotube fluorophores. With NIR-FE imaging, we were able to push the detectable limit of SWNT staining of cells down to an ultralow concentration of ~50 pM. Further, we observed different degrees of fluorescence enhancement for endocytosed, intracellular SWNTs vs. nanotubes on the cell membrane at the cell/gold interface, suggesting the possibility of observing transmembrane endocytosis of live cells based on the degree of fluorescence enhancement.

Also important is the present NIR-FE imaging of biological system is general for commonly used low quantum yield organic dyes including IR800. To our knowledge, this is the first fluorescence enhanced imaging of cells on Au nanostructures in the NIR. Previously, Ag substrates were used for fluorescence enhanced biological imaging in the visible with organic dyes.

Cell-type selective staining and subsequent imaging of cells were carried out with RGD and IR800 conjugated SWNTs, water-solubilized by 25% DSPE-PEG(5 k)-NH$_2$ (1,2-distearoyl-sn-glycero-3-phosphoethanolamine-N-[amino(polyethyleneglycol) 5,000]) and 75% C18-PMH-mPEG(90 k) (poly(maleic anhydride-alt-1-octadecene)-methoxy(polyethyleneglycol)90,000). The RGD peptide ligand was linked to the amine groups on SWNTs for selectively binding to $\alpha_v\beta_3$-integrin positive U87-MG cells over the $\alpha_v\beta_3$-integrin negative MCF-7 cells. Meanwhile, we also covalently attached IR800 dye molecules onto SWNTs to afford SWNT-IR800-RGD conjugates (FIG. 14A). Upon excitation at 658 nm, the SWNT-IR800-RGD conjugate emitted in the range of 1000-1400 nm, due to the intrinsic bandgap photoluminescence of SWNTs. Upon excitation at 785 nm, the conjugate emitted fluorescence in the 800-1000 nm range due to the attached IR800 molecules. This unique SWNT-IR800 conjugate allowed for tagging of cells using two NIR fluorophores in two different imaging windows in the 800-1400 nm range. Atomic force microscopy (AFM) imaging showed the SWNT conjugates with lengths ranging from 100 nm to 3 μm and an average length of ~1.0 μm.

We synthesized Au/Au films on quartz (FIG. 14B) via solution phase growth, with optical extinction in the NIR (FIG. 14C) for the highest fluorescence enhancement of both SWNTs and IR800 placed on top of the gold film. It was empirically determined that 3-5 mM HAuCl$_4$ was optimal for seeding while HAuCl$_4$ and NH$_2$OH concentrations of 2-3 mM were ideal for the growth step, yielding a broad plasmon resonance into the NIR at wavelengths even >1 μm. For SWNT-IR800-RGD conjugates drop-dried from a solution onto both bare quartz and Au/Au film on quartz, photoluminescence versus excitation (PLE) spectra revealed fluorescence enhancement of both IR800 and SWNTs on the Au/Au film. The average enhancement of SWNT photoluminescence was ~10 times, and the enhancement was ~5 times for the IR800 dye attached to SWNTs. This result clearly showed the excellent capability of fluorescence enhancement by the Au/Au film for fluorophores emitting in the 0.8-1.4 μm NIR window including IR800 and SWNTs.

For targeted cell staining and imaging, U87-MG cells and MCF-7 cells were trypsinized and mixed with SWNT-IR800-RGD conjugates at a concentration of ~30 nM of SWNTs at 4° C. for 1 h to prevent endocytosis during staining. The cells were split into two groups and placed onto a quartz microscope slide and Au/Au film respectively for immediate fluorescence imaging using an InGaAs camera. The $\alpha_v\beta_3$-integrin positive U87-MG cells treated with the SWNT-IR800-RGD conjugate showed ~9-fold higher SWNT fluorescence signal on Au/Au than on quartz, excited at 658 nm under a short exposure time of ~300 ms. Much longer exposure times (1~3 s) were needed to obtain high quality SWNT-stained cell images on quartz, similar to previous biological imaging with SWNT fluorophores. The $\alpha_v\beta_3$-integrin negative MCF-7 cells on both Au/Au and quartz showed little SWNT fluorescence signal. The selectivity of RGD-SWNT labeling of cells, defined as the ratio of SWNT emission intensity of $\alpha_v\beta_3$-integrin positive U87-MG cells compared to that of $\alpha_v\beta_3$-integrin negative MCF-7 cells, was as high as ~17 for cells on Au/Au substrate (FIG. 15A), suggesting highly selective staining and molecular imaging of cells with NIR-FE on the gold films.

We also trypsinized and mixed cells with SWNT-IR800-RGD conjugates at 37° C. (instead of 4° C. as above) for 1 h, a condition known to afford endocytosis of carbon nanotubes inside cells. The U87-MG and MCF-7 cells thus treated were plated onto Au/Au and quartz for NIR imaging. In contrast to the ~9-fold enhancement observed for cells stained at 4° C., nanotube fluorescence in the $\alpha_v\beta_3$-integrin positive U87-MG cells treated at 37° C. was enhanced by only ~2-fold on Au/Au film compared to on quartz substrate. Also noticeable was the higher false-positive signal intensity in the $\alpha_v\beta_3$-integrin negative MCF-7 cells, due to the expected increase of non-specific uptake of SWNTs by cells at 37° C. than at 4° C.

The fluorescence enhancement of the molecularly selective SWNT labels on U87-MG cells may be attributed to coupling between the emissions of SWNT tags and surface plasmon modes in the Au/Au substrates. Resonance coupling between SWNT emission and re-radiating plasmonic modes in the Au/Au films shortened the radiative lifetimes of SWNTs, affording higher fluorescence quantum efficiency. It was found that surfactant-coated SWNTs closer to the Au/Au surface exhibited higher fluorescence enhancement, decaying when SWNTs were placed away from the surface with a half-decay distance of ~5 nm, on the same order of cell membrane thickness. At 4° C., most of the SWNTs were blocked from endocytotic uptake by the U87-MG cells, and SWNTs on the cell membrane interfacing with the Au/Au substrate were strongly coupled to the surface plasmonic modes in the gold film and thus responsible for the large, ~9-fold enhancement in fluorescence compared to on quartz (FIG. 15A). On the other hand, when incubated at 37° C., SWNTs were endocytosed into the cytoplasms of the cells and hence spatially separated from the gold surface, giving a reduced fluorescence enhancement of ~2-fold (FIG. 15B). The SWNT-Au distance dependent fluorescence enhancement could also explain the measured increase in cellular targeting selectivity with cells on Au/Au vs. quartz substrate (FIG. 15A). For integrin negative MCF-7 cells, the fluorescence signals detected were due to autofluorescence inside the cells and non-specific uptake effects, which were distributed through the cells in three dimensions. These non-specific signals were barely enhanced by the Au/Au substrate, while the specific SWNT signals on the integrin-positive U87-MG cells at the cell-gold interface were enhanced to the maximum degree due to proximity to Au. Thus, preferential enhancement of specific cell membrane surface fluorescence afforded more sensitive and selective imaging of cell membrane receptors. This effect was consistent with little enhancement in the cell labeling selectivity observed on Au/Au substrate for cells treated by SWNT-RGD at 37° C. (FIG. 15B). Interestingly, these results suggested that the distance dependent fluorescence enhancement effect could be used for tracking transmembrane behavior in live cells, since the thickness of cell membrane was on the same order of magnitude as the enhancement decay distance (~5 nm).

Figure 16:
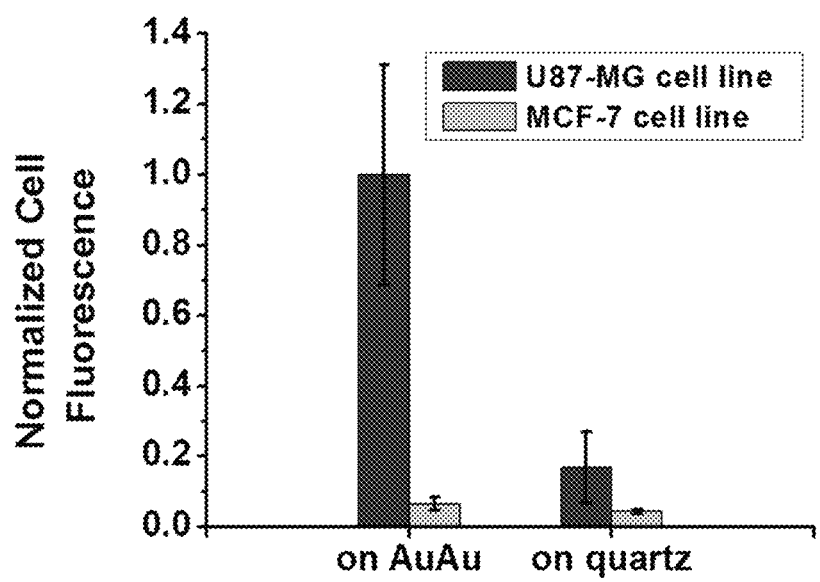
FIG. 16 is a bar chart of normalized cell fluorescence in SWNT-IR800-RGD stained U87-MG cells and in similarly treated MCF-7 cells on Au/Au film and on quartz respectively.

Our NIR-FE imaging of cells was general for various NIR fluorescent organic dyes. We chose IR800 as a representative organic dye due to its wide use for biological imaging. The IR800 dye molecules (shown as a circle in FIG. 14A) bound to SWNTs deposited on the same Au/Au film exhibited a fluorescence enhancement by ~5-fold. We used SWNT-IR800-RGD conjugates to target $\alpha_v\beta_3$-integrin positive U87-MG cells and performed cell fluorescence imaging in the IR800 fluorescence channel. Comparing SWNT-IR800-RGD stained U87-MG and MCF-7 cell lines respectively, resulted in images (not shown) in which the $\alpha_v\beta_3$-integrin positive U87-MG cells showed significantly higher positive IR800 fluorescence signal in the 790-820 nm region upon 785 nm excitation, while the $\alpha_v\beta_3$-integrin negative MCF-7 cells showed little IR800 signal under the same imaging condition. This again confirmed high specificity of molecular imaging and the coexistence of IR800 and RGD on SWNTs. A significant fluorescence enhancement on Au/Au vs. quartz by ~6-fold for IR800 labels on cells, with a positive/negative selectivity ratio of ~16 on Au/Au film vs. ~4 on quartz was also shown (FIG. 16). These results demonstrated the generality of NIR-FE imaging of cells for high molecular sensitivity and selectivity.

Thus these examples show plasmonic gold substrates to perform near-IR fluorescence enhanced molecular imaging of cells in the 0.8-1.4 μm spectral window based on carbon nanotubes and organic fluorophores. The novel solution-grown gold substrate was general in enhancing both carbon nanotubes and infrared dye IR800, by ~9 times and ~6 times respectively, affording higher sensitivity and specificity of molecular cell imaging in the advantageous 0.8-1.4 μm spectral window. Cell labeling at different incubation temperatures blocked or allowed endocytosis of nanotube fluorophores, leading to observation of a distance dependent fluorescence enhancement inside cells. This effect could be used to observe transmembrane behavior of single NIR fluorophores in live cells when the fluorescence enhancement decay distance matches cell membrane thickness. Further possibilities with NIR-FE imaging include single molecule imaging and tracking of SWNTs or other NIR dyes on cell membrane, molecular imaging of low abundance cell membrane proteins, and even some in vivo NIR-FE imaging using smaller yet enhancing Au nanostructures as enhancing platform to serve in a fluidic system.

Section IV. Protein Microarrays and Other Biosensors

Methods of preparing Au/Au films for SERS substrates; Au/Au films for NIR fluorescence enhancement in immunoassays; and NIR enhancement of living cells are described in detail herein, and it is understood that the materials and devices described are adaptable to a number of biosensor formats. That is, contemplated and described below are various biosensors for use in a SERS or fluorescent spectroscopic detection system. The detection systems, such as a Raman microscope, are commercially available. The samples may comprise a substrate for supporting samples; a gold film applied to said substrate, said gold film having plasmonic nano-islands of gold grown on a gold seed layer; and (c) an array of biological samples disposed in contact with the gold film. In certain preferred embodiments, the nano-islands are separated by gaps of between 10 and 100 nm and/or the nano-islands are between 10,000 and 25,000 $nm^2$ in area. The biological samples may be proteins, nucleic acids, carbohydrates, or cells. The various self-assembled monolayers (SAMs) described below may be part of the biosensors, and may be applied to chips having sample spots applied using known methods, and methods described below. The present Au/Au gold film may be applied in solution phase either over or under the array of biological samples. The samples may be conveniently arrayed in a microarray format, where the samples are spotted onto a chip. The samples may comprise antigen-antibody complexes and an antibody has been labeled for spectroscopic detection. The biological samples have been labeled for NIR detection.

SERS spectroscopy and metal-enhanced NIR can be carried out on the unique sample configurations provided here. The inert substrate is treated to contain the sample and the analyte, and the solution based method is sued to create the present Au/Au non-islands on the substrate. The substrates may be prepared efficiently simply by the various coating, rinsing and spotting steps described. No etching steps are required, no individual nanoparticles need to be created and treated, and no harsh high temperature deposition methods are needed.

The present plasmonic substrates are used as microarray platforms for fluorescence enhanced, multiplexed immunoassay of proteins down to 0.01 pg/ml of 1 fM level over 6 logs of dynamic range. The proteins that can be included in the microarrays include antibodies, autoantibodies, protein biomarkers for diseases, cytokines and other biological molecules.

Protein microarrays can be prepared in a number of ways by spotting the desired proteins onto the present NIR-FE active plasmonic gold substrates. Exemplary methods are described e.g. in Charych et al. US 2003/0013130, Schembri et al. US 2003/108726, and Brennan et al. US 2009/0088329. In particular, Talapatra et al., "Protein microarrays: challenges and promises," Pharmacogenomics 3(4)

1-10 (2002) describes the preparation of protein microarrays on gold surfaces and glass slides. The novel surfaces described here are shown below to be adaptable to microarray creation.

A protein microarray provides a two dimensional array of addressable "spots" of protein, having a known quantitation. The spots comprise immobilized, purified capturing molecules (antigens for protein biomarkers and autoantibodies; antibodies for cytokines) and prevent non-specific binding, thus optimizing positive binding and reducing background and false signal. One may chemically modify the plasmonic gold film for immobilization of multiplexed capturing proteins (antigens or antibodies) by first making self-assembled monolayers (SAM) of thiol-containing molecules terminated with carboxylate groups. Branched hydrophilic polymers of 6-arm-poly(ethylene glycol) (PEG)-NH2 can then be grafted to SAMs, followed by reaction with succinic anhydride to obtain carboxylic acid groups off the 6-arm-PEG. Multiplexed capture antigens and antibodies (targeting protein biomarkers, antibodies and cytokines) can then be immobilized on different spots of the same Au substrate with a robotic arrayer through covalent linkage between NH2 groups on the proteins and carboxylic acid groups on Au activated by EDC/NHS. This protein immobilization method utilizes the unique thiol-Au chemistry (not possible on glass or other conventional substrates) and branched-PEG to impart highly effective immobilization of capturing molecules and to prevent non-specific binding of target analytes.

Materials for Solution Phase Gold Seeding

Superfrost Plus glass slides and quartz slides were purchased from Fisher Scientific and rinsed with acetone, IPA, and methanol prior to use. Silicon wafers with native oxide layers were purchased from the Center for Integrated Systems at Stanford University. Poly(vinyl chloride) coverslips were purchased from Ted Pella, Inc. Sylgard 184 was purchased from Dow Corning and cured by standard procedures. Chloroauric acid trihydrate, hydroxylamine HCl, sodium borohydride and benzenethiol were purchased from Sigma-Aldrich. Ammonium Hydroxide (30% ammonia) was purchased from Fisher Chemicals. Raw single-walled carbon nanotubes (SWNTs) were purchased from Unidym, and DSPE-PEG(5000)-amine was purchased from NOF corp. Purified carcinoembryonic antigen (CEA) was purchased from R&D systems, monoclonal mouse anti-CEA (5910) was purchased from Medix Biochemica (Biospacific) and polyclonal rabbit anti-CEA (ab15987) was purchased from Abcam. Goat anti-Rabbit IgG was purchased from Jackson Immunoresearch.

Solution Phase Au/Au Film Synthesis

Figures 2A, 2B, 2C, 2D, 2E, 2F, 2G, 2H, 2I, 2J, 2K:
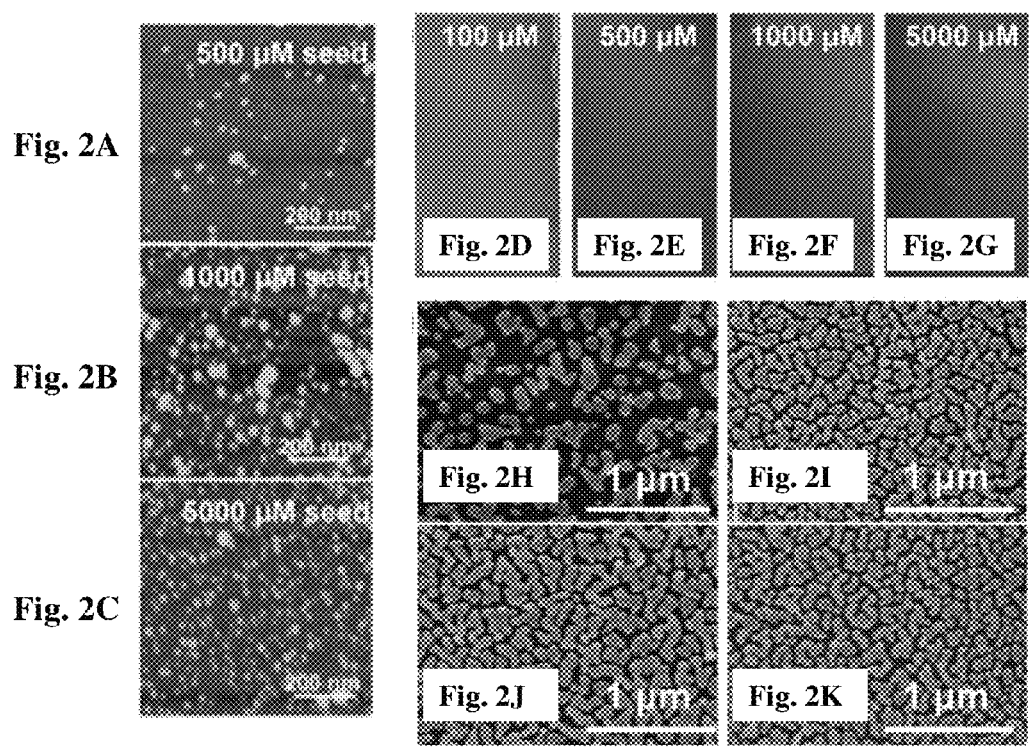
FIGS. 2A, 2B, and 2C shows atomic force microscopy topography images of $Au^0$ seeds deposited on $SiO_2$ demonstrating the dependence on seeding density with $HAuCl_4$ concentration.
FIGS. 2D, 2E, 2F and 2G shows digital photographs of Au/Au films grown on glass at the indicated $HAuCl_4$ seeding concentration, following reduction and growth at a fixed $HAuCl_4$ and $NH_2OH$ concentration of 500 µM.
FIGS. 2H, 2I, 2J and 2K shows the SEM images of Au/Au films grown on glass at the indicated $HAuCl_4$ seeding concentration.

Deposition/Precipitation of $Au^{3+}$ onto Glass, Quartz, Silicon, and Bioassay Susbstrates The substrate of choice was submersed in a solution of chloroauric acid ranging in concentration (0.5 mM, 1 mM, and 5 mM), to which ammonium hydroxide was added at 20 µL/mL (0.6% ammonia) under vigorous agitation. Similar deposition/precipitation of $Au^{3+}$ onto metal oxide surfaces has been reported for use in catalytic applications.[1-3] A kinetics study revealed no obvious change in seeding density or particle size at soaking times up to 20 minutes based upon AFM data, UV-vis-NIR absorbance and benzenethiol Raman scattering measurements. Variation from 0.5 mM to 5 mM showed marked increases in surface coverage and particle uniformity on $SiO_2$ as evidenced by AFM (FIG. 2A-2C). Estimated enhancement factors at 785 nm excitation for benzenethiol on the substrates show $5 \times 10^6$ enhancement for 100 µm seed and about $1.5 \times 10^7$ enhancement for 500, 1000, and 5000 µM seeds. As expected from their similar plasmon resonances and structural features, the densely seeded Au/Au films demonstrated similar EFs, ~$10^7$, as measured by benzenethiol (BT) at 785 nm excitation, where as lower seeding density led to lower EFs. Additionally, adjustment of ammonium hydroxide solution to pH 5, 7, and 11 prior to addition of $HAuCl_4$ (in order to change the final seeding solution pH) failed to produce uniform seeds. Replacement of $NH_4OH$ with NaOH resulted in a colorless solution and similarly failed to produce adequate seeding. Following incubation in the seeding solution, the substrate was washed by sequential immersion into two water baths.

Solution Phase Reduction of Seeded $Au^{3+}$

Immediately following wash steps, the $Au^{3+}$ seeded substrate was submersed into a solution of 1 mM sodium borohydride at room temp on an orbital shaker. The reduction was nearly immediate, and resulted in a faint pink color formed on the surface of densely seeded substrates, and was accompanied by development of a plasmon absorbance at 525 nm suggesting nanoparticle formation. AFM confirmed the presence of nanoscopic spheres with heights 5-10 nm (FIGS. 1B and 2A). Reduction was allowed to proceed for 1-5 minutes, followed by two submersions of the substrate in water baths. Heating of the substrate to high temperatures (>80° C.) also caused a reduction to $Au^0$ without the need for a reducing agent, likely due to decomposition of the Au-containing cluster.

Growth of Au Films by Hydroxylamine Reduction of $HAuCl_4$

Hydroxylamine reduction of chloroauric acid has been described previously by Natan and co-workers[4]. Au reduction is specific to the $Au^0$ seeds, because the rate of $HAuCl_4$ reduction by hydroxylamine is much greater for adsorbed $Au^{3+}$ ions than those in solution. Film growth was first studied as a function of seeding density, by varying the $Au^{3+}$ concentration during seeding ($Au^{3+}$ concentrations of 0.1 mM-5 mM), and performing growth under fixed conditions (500 µM $Au^{3+}$ and $NH_2OH$). Au/Au films were obtained by varying the concentration of $HAuCl_4$ during "seeding," and fixing the hydroxylamine-mediated growth conditions. Very low density Au nanoparticle seeding results in mostly individualized Au nanoparticles after film growth at 500 µM $Au^{3+}$, where as higher density seeding (>500 µM) yields a semi-contiguous sub-monolayer. Seeding concentrations above 0.5 mM $Au^{3+}$ showed similar Au/Au film formation following 500 µM Au growth, with broad plasmons centered between 575 nm and 600 nm, where as lower seeding densities formed sharper plasmon absorbances, centered around 525 nm. As inferred from the absorbance spectra, SEM imaging confirmed that dense seeding layers led to Au particle coalescence following growth, whereas low density seeding led to mostly individual or twinned particles. Next, the concentration dependence of the growth solution (FIG. 3) was varied (100 µM-2000 µM) at a fixed seeding condition (5 mM $Au^{3+}$). In all cases, reduced, Au nanoparticle-seeded substrates were moved directly from wash water baths to a solution of $HAuCl_4$, and $NH_2OH$ was added 1:1 with $Au^{3+}$ under vigorous agitation to initiate growth. Growth proceeded at room temperature with manual agitation or on an orbital shaker at 100 RPM until obvious development of the film ceased, 15-20 minutes.

Seeding concentrations above 0.5 mM $Au^{3+}$ showed similar Au/Au film formation following 500 µM Au growth, with broad plasmons centered between 575 nm and 600 nm, where as lower seeding densities formed sharper plasmon absorbances, centered around 525 nm. As inferred from the absorbance spectra, SEM imaging confirmed that dense seeding layers led to Au particle coalescence following growth, whereas low density seeding led to mostly individual or twinned particles. Optimal growth conditions led to the formation of nano-island films with gap spacing of 10-100 nm.

Gold concentration variations during growth had a large effect on Au/Au films resulting from high density seeded substrates (5 mM $HAuCl_4$). Increasing $Au^{3+}$ concentrations of 100 µM, 250 µM, 500 µM, 1000 µM, and 2000 µM led to progressively red-shifted and broadened plasmon resonances (FIG. 3), and increased film thickness (monitored as extinction and reflectance) as observed previously.[4] Morphology of the resulting Au/Au film by SEM shows individualized Au nanoparticles at 100 µM $Au^{3+}$ eventually coalescing at higher concentrations, and finally forming a continuous rough gold film at 2000 µM with OD~2 (FIG. 3). Optimal seeding and growth concentrations of $HAuCl_4$ was 3 mM/1 mM for SERS substrates and 3 mM and between 0.5 and 0.75 mM for fluorescence enhancing substrates.

Electron-Beam Silver Evaporation

E-beam evaporation of silver onto glass slides has been described previously (including by our group[5]). Briefly, substrates were loaded into a cryo-vacuum chamber and the pressure was reduced below $5 \times 10^{-7}$ torr. A silver source was irradiated by an e-beam gun and 5 nm of Ag was evaporated at a rate of 0.2 nm/sec.

UV/Vis/NIR Absorbance Measurements

Plasmon resonances of Au/Au films on glass substrates, as well as silver-coated glass, were measured by UV-vis-NIR absorbance spectroscopy by a Cary 300 spectrophotometer, background-corrected for any glass contribution.

AFM Imaging of Gold Seeds on $SiO_2$

Seeded gold substrates were prepared at varying $HAuCl_4$ concentrations as described above on ~0.25 cm$^2$ $SiO_2$ substrates. Following reduction, the substrates were dried and directly imaged in tapping mode by a Nanoscope III multimode AFM (Veeco) with Nanoscope 5 software for height analysis.

SEM imaging of Au/Au Films on Glass

Au/Au films grown on glass and $SiO_2$ were imaged via scanning electron microscopy due to high surface roughness not amenable to AFM. Images were acquired on an FEI XL30 Sirion SEM with FEG source at 5 kV acceleration voltage.

Benzenethiol SAM Formation, Raman Measurement, and Enhancement Factor Calculation Benzenethiol (BT) was used as a reporter molecule for surface-enhanced Raman scattering of Au/Au films in addition to silver-coated substrates. Substrates were immersed in a 1 mM solution of BT in ethanol overnight at room temperature, and then rinsed gently with ethanol and dried. Raman scattering spectra of adsorbed and bulk BT were acquired on a Horiba LabRam HR800 microRaman spectrometer with 785 nm excitation and Rayleigh rejection edge filter. BT-coated substrates were irradiated at 80 mW, 785 nm through a 10× objective lens with the excitation laser raster-scanned over a 50×50 µm$^2$ area (Horiba DuoScan) within the 1 second integration time per pixel. At least twenty spectra were acquired on each substrate to assure uniformity of the substrate and the resulting spectra were baseline corrected and averaged. The Raman scattering spectrum of a bulk solution of BT was acquired by drawing the solution into a glass capillary tube and measuring 10 Raman scattering spectra under identical excitation conditions. Enhancement factors were calculated as previously described.[6]

$$EF(\lambda) = \frac{\frac{I_{SERS}}{N_{SERS}}}{\frac{I_{bulk}}{N_{bulk}}}$$

Where $I_{SERS}$ and $I_{bulk}$ are the Raman scattering intensity of the ~1000 cm$^{-1}$ BT scattering peak intensity and $N_{SERS}$ and $N_{bulk}$ are the number of BT molecules sampled in the measurement. The excitation volume was estimated by the 1/e$^2$ method over a silicon edge to be 6.6 um in diameter and 900 um in height. Calculation of $N_{bulk}$ follows directly from the solution density, however $N_{SERS}$ requires knowledge of the film surface area (estimated from SEM imaging) and packing density of BT on gold, which was assumed to be $6.8 \times 10^{14}$ BT molecules/cm$^2$.[6]

It was noted that very high power densities (~10$^7$ W/cm$^2$) attained at 80 mW excitation through a 100× objective lens caused non-linear effects in the Raman scattering intensities of both BT and SWNTs. Cycling of high and low power acquisitions led to decreases in scattering intensity, attributed to morphology changes associated with heating of the substrate. Raman scattering acquisition power densities were selected throughout to avoid such effects (i.e. excitation power was reduced 10-fold for Raman scattering collection through high magnification objective lenses).

A variety of materials may be applied to the present Au/Au films. This may be done to enhance the signal obtained from activity of the plasmonic film, and/or to facilitate attachment of biomolecules to the film. For example, one may apply thiol, mercaptan, poly-L lysine, dextran, amino dextran and carboxy-methyl dextran to the film. Further description of chemical modifications that can be applied to gold films in biosensors may be found in U.S. Pat. No. 7,842,498, entitled "Hydrophobic surface chip."

SWNT Bioconjugate Preparation

Bioconjugated single-walled carbon nanotubes suspended by non-covalent surfactants have been described in detail previously.[5, 7] Briefly, Raw HiPCO SWNTs were suspended in water by bath sonication for one hour in 1,2-Disteroyl-sn-glycero-3-phophoethanolamine-[(polyethylene glycol)$_{5000}$]-amine (DSPE-5 kPEG-NH2) and DSPE-PEO (branched mPEG$_{8000}$). The resulting suspension was centrifuged at 22,000 g for 6 hrs to remove poorly suspended SWNTs and impurities, and was then filtered 6 times through a 4 mL volume, 100 kDa MWCO centrifugal filter (Amicon Ultra). Approximately 800 nM of SWNTs were mixed with 1 mM of sulfo-SMCC (pierce) in PBS at RT for 2 hours, followed by another round of filtration (6 times) through 100 kDa MWCO centrifugal filters. Affinity purified goat anti-rabbit IgG was mixed at a 1:10 mole ratio with 2-immunothiolate (Traut's reagent, pierce) in PBS with 5 mM EDTA added for 1 hour at room temp, followed by two rounds of filtration through a 500 uL volume 100 kDa MWCO filter. Finally, the thiolated anti-rabbit IgG was mixed with SMCC-activated SWNTs at a 1:2 ratio (Ab: SWNT) and allowed to react for 48 hours at 4° C. The product was used directly.

Au/Au Film Optimization for Deposition onto Raman Bioassay

Au seeding by deposition/precipitation appears to be very general, and is even able to uniformly coat a protein bioassay slide. Optimization of both seeding and growth parameters for Au/Au film deposition was performed by subjecting duplicate immunoassays on glass to various deposition conditions (FIG. 5). Seeding and growth concentrations of HAuCl$_4$ were varied precisely as above with slightly different results. Indeed, Au/Au films were deposited uniformly on top of the protein-coated assay substrate (a 75 mm by 25 mm slide), with slightly different morphology than on bare glass, likely due to different surfaces charge properties and surface roughness. High density seeding (5 mM HAuCl$_4$) combined with 1000 μM HAuCl$_4$:NH$_2$OH growth yielded the greatest relative enhancement factor for SWNTs.

CEA Assay Procedure & Raman Measurement

In step 1, CEA immunoassays were performed on superfrost plus glass slides that were cleaned with acetone, IPA, and methanol prior to robotic, contact microarray printing of 1 uM mouse anti-CEA. At least 9 duplicates microspots of mouse anti-CEA were printed per "well", defined by application of hydrophobic marker (super PAP pen mini, Cedarlane). The substrate was blocked overnight in PBS with 3% fetal bovine serum and 0.05% tween-20 added (3% FBS in PBST) at 4° C.

For step 2, the substrate was rinsed with PBST and then varying concentrations of CEA from 1 nM to 1 fM (and a blank control) spiked into 3% FBS in PBS were incubated in the "wells" for 6 hours in a humid atmosphere at room temp on an orbital shaker. The substrate was then carefully washed to avoid mixing of the wells, twice with PBST and once with PBS.

In step 3, 20 nM of rabbit anti-CEA in PBS was incubated in the "wells" for 1.5 hours at room temp on an orbital shaker, followed by the same washing procedure.

In step 4, 4 nM of anti-rabbit-conjugated SWNTs were incubated in the "wells" for 20 minutes at room temp on an orbital shaker, followed by washing 3× in PBST, once in PBS, and briefly in water before drying.

Finally, in step 5, a gold-on-gold film was then deposited onto the assay substrate by seeding at 5 mM Au$^{3+}$ and growth at 1000 μM Au$^{3+}$.

Raman scattering measurements of SWNT labels bound to CEA immunoassay protein spots were taken with a Horiba Labram HR800 equipped with a 300 line/mm grating set to pixel binning of 2, with 8 mW (10% power) 785 nm excitation laser, through a 100× objective. Integration times were 100 msec, or 10 msec as noted, with the laser beam rastered over an area of 5×5 μm$^2$ within the integration time (Horiba DuoScan). Maps of the microarray spots were generated by taking 30 μm steps, and the average intensity of the SWNT G-band was calculated following baseline correction. Error bars represent the standard deviation of the means for at least 9 duplicated assay spots. At 100 msec integration, a complete calibration curve measurement requires ~2 hours, where as at 10 msec integration, this time is reduced to about 20 minutes accompanied by increased noise and loss of some sensitivity.

EXAMPLES

Example 1: Seeding of Gold Precursors onto Unmodified Substrates

Preparation of Au/Au films involves three steps: seeding of gold precursors, reduction into Au$^0$ clusters, and selective growth by hydroxylamine reduction of HAuCl$_4$ (FIG. 1). Seeding was accomplished by addition of ammonium hydroxide into a solution of chloroauric acid containing the substrate of choice (see Methods). Immediately following ammonium hydroxide addition, the transparent yellow, acidic HAuCl$_4$ solution became cloudy and orange-yellow, with pH~9. The deposition rate of the Au$^{3+}$ species onto the substrate was found to be rapid. Increased exposure times from one minute to twenty minutes did not significantly affect the density or size of gold seeds immobilized on the substrate.

Seeding density of Au seeds was dependent upon the initial concentration of HAuCl$_4$ into which the substrate was submerged prior to precipitation by ammonium hydroxide. For inorganic substrates such as glass and SiO$_2$, an increase of HAuCl$_4$ from 0.5 mM to 5 mM led to significantly increased density and uniformity of Au NP precursor seeds (FIG. 2A-2C). Polymeric substrates such as poly(vinyl chloride), PVC, and poly(dimethylsiloxane), PDMS, required slightly Au$^{3+}$ concentrations of 10 mM in order to obtain high density seeing.

Example 2: Solution Phase Reduction of Gold Precipitate Precursors Enables Gold Film Growth Following the deposition of Au seeds by precipitation onto the substrate of choice, the substrate was immersed into a 1 mM solution of sodium borohydride, which led to rapid formation of Au$^0$ nanoparticles, evidenced by a faint pink-purple color change of the substrate. Atomic force microscopy revealed formation of Au NPs with diameters of 5-10 nm (FIG. 1b), and UV/Vis absorption spectroscopy revealed a weak surface plasmon resonance at 525 nm, typical of Au NPs in this size range.

Example 3: Selective Reduction of Au$^{3+}$ onto Precursor Au Seeds Yields Plasmonic Gold-on-Gold (Au/Au) Films Submersion of the seeded substrate into an aqueous solution of chloroauric acid and hydroxylamine initiated selective reduction of Au$^{3+}$ onto the seed layer, and thus the Au precursor seeds were grown into plasmonic nano-islands (i.e., "isolated island areas") (FIG. 1D). Hydroxylamine-mediated gold reduction led to a color change of the substrate from pink to blue-purple, and finally a golden color was observed on the substrate as the film thickened (FIG. 1C). SEM imaging revealed that the Au nano-islands formed on the substrate were separated by ~10-100 nm gap spacing, a morphology desirable for local electrical field enhancement and SERS.[20]

The resulting Au/Au film thickness and structure depended on both the density of gold precursor seeding and the concentration of Au$^{3+}$ ions during hydroxylamine-mediated growth. At a "growth" concentration of 500 uM HAuCl$_4$, a substrate seeded at very low density failed to produce a network of interacting plasmonic gold structures, evidenced by SEM imaging, and a surface plasmon resonance at ~525 nm, typical of non-interacting Au NPs. Under identical growth conditions, however, a substrate seeded at higher density yielded a network of interacting plasmonic nano-islands, exhibiting a red-shifted plasmon resonance and higher optical density (FIG. 2D-2K). Au/Au films were obtained by varying the concentration of HAuCl$_4$ during "seeding," and fixing the hydroxylamine-mediated growth conditions. Very low density Au nanoparticle seeding results in mostly individualized Au nanoparticles after film growth at 500 μM Au$^{3+}$, where as higher density seeding (>500 μM) yields a semi-contiguous sub-monolayer. Seeding concentrations above 0.5 mM Au$^{3+}$ showed similar Au/Au film formation following 500 μM Au growth, with broad plasmons centered between 575 nm and 600 nm, where as lower seeding densities formed sharper plasmon absorbances, centered around 525 nm. As inferred from the absorbance spectra, SEM imaging confirmed that dense seeding layers led to Au particle coalescence following growth, whereas low density seeding led to mostly individual or twinned particles. As expected, increasing the concentration of $HAuCl_4$ during growth at a fixed seeding density led to thicker and thicker Au/Au films with higher coverage of gold nano-islands, exhibiting monotonically red-shifted plasmon resonances and increasing optical density (FIG. 3A).[18] Digital photographs of Au/Au films were obtained by fixing the concentration of $HAuCl_4$ during "seeding," and varying the film growth conditions. Glass substrates were seeded at 5 mM $HAuCl_4$, and hydroxylamine-mediated growth was performed at (i) 100 µM, (ii) 250 µM, (iii) 500 µM, (iv) 1000 µM, and (v) 2000 µM of both $HAuCl_4$ and $NH_2OH$. Films increase in thickness at higher growth concentrations, accompanied by increased and red-shifted plasmon absorbances (data not shown). It was seen that absorbance spectrum of the surface plasmon resonance of an optimal Au/Au film, seeded on glass at 5 µM $HAuCl_4$ and was grown after reduction at 1 mM $HAuCl_4/NH_2OH$. Surface-enhanced benzenethiol Raman scattering spectrum from the Au/Au film was also observed. The optimal film yields an enhancement factor of $>10^7$. At very high concentrations of $HAuCl_4$ during hydroxylamine-mediated growth, the nano-islands coalesced into a continuous, roughened, gold film.

Deposition of Au/Au films onto unmodified polymeric substrates such as PVC and PDMS showed similar seeding and growth behavior to that which was observed on glass and $SiO_2$. Hydroxylamine-mediated reduction of $HAuCl_4$ onto Au-seeded PVC and PDMS yielded uniform growth of interacting, plasmonic gold isolated island areas, observed by absorbance spectroscopy and SEM imaging. These substrates retained their flexible character following Au/Au film growth, with no obvious signs of cracking upon repeated bending.

Example 4: Optimization of Au/Au Films for Surface-Enhanced Raman Scattering Benzenethiol self-assembled monolayers were used as Raman reporters to study the SERS properties of Au/Au films on glass, PVC and PDMS, as well as on Ag films, prepared on glass. Au/Au films grown from a low density seeding layer yielded only a weak SERS effect at 785 nm excitation, while films seeded at higher densities showed greater enhancement factors. Estimated enhancement factors at 785 nm excitation for benzenethiol on the substrates show $5 \times 10^{6.5}$ enhancement for 100 µm seed and about $1.5 \times 10^7$ enhancement for 500, 1000, and 5000 µM seeds. As expected from their similar plasmon resonances and structural features, the densely seeded Au/Au films demonstrated similar EFs, $\sim 10^7$, as measured by benzenethiol (BT) at 785 nm excitation, where as lower seeding density led to lower EFs. SERS enhancement factors of the various Au/Au films were also dependent upon the hydroxylamine-mediated growth conditions. Au/Au films demonstrated increasing SERS enhancements with increasingly red-shifted plasmons and increasing thickness up to a maximum value, followed by a precipitous drop in SERS resulting from complete coalescence of the gold film at very high concentrations of $HAuCl_4$ during film growth (FIGS. 3B and 3C). Optimal Au/Au films produced on glass, seeded at 5 mM $HAuCl_4$ with selective Au growth of 1 mM of HAuCl4 and $NH_2OH$, exhibited a broad surface plasmon resonance at 610 nm, and enhanced the Raman scattering intensity of benzenethiol by a factor of $\sim 10^7$ at 785 nm excitation. For comparison, silver films were prepared on glass using previously described methods.[7, 17] Silver mirror films yielded a similar benzenethiol Raman scattering intensity as the optimal Au/Au film (FIG. 3B), but visibly oxidized over time, while silver films prepared by evaporation afforded benzenethiol Raman scattering intensity 5-fold lower than optimal Au/Au films.

SERS was also observed from Au/Au films seeded and grown onto unmodified polymeric substrates. SERS measurements of benzenethiol chemisorbed onto Au/Au films supported by glass, PVC, and PDMS revealed that Raman scattering enhancement for Au/Au films on all three support substrates were of a similar order of magnitude. Uniformity and reproducibility of the Au/Au films were excellent, as evidenced by spatially mapping the SERS spectra of benzenethiol-coated films over large areas and on duplicate substrates. Uniformity of Au/Au films was shown by Raman scattering intensity map of the 1575 cm$^{-1}$ benzenethiol (BT) peak over a 1 mm$^2$ area on an Au/Au film prepared by 1 mM Au$^{3+}$ seeding and 1 mM Au$^{3+}$ growth followed by soaking in 1 mM BT in ethanol overnight. Raman spectra were acquired following 80 mW 785 nm excitation through a 10× objective lens with a 50×50 µm laser spot size. X & Y step size is 150 µm. This and other experiments shoed that Raman intensity was essentially uniform across the area of the film. It was, however, observed that the Au/Au films SERS properties were reduced when the film was damaged at extremely high laser power densities (~10 MW/cm$^2$).

Example 5: Au/Au Films can be Deposited from Solution onto Protein-Coated Bioassays Having produced Au/Au films on glass, quartz, $SiO_2$, PVC, and PDMS, the versatility of the method was tested by preparing SERS-active Au/Au films atop protein bioassays. Such SWNT-labeled bioassays, described thoroughly elsewhere[7], are coated by proteins and thus are not suitable substrates for silanization and deposition of pre-made Au NP seeds for film growth[18]. Moreover, while electron-beam evaporation of silver onto protein bioassays has been shown to yield SERS (FIG. 5) the silver film rapidly oxidizes over the course of a few hours, and the SERS effect is eventually lost.

We first performed sandwich immunoassays on glass substrates, using SWNT Raman labels[7] (FIG. 4A) which act as high scattering cross-section Raman tags, with a resonance-enhanced Raman G-band at 1590 cm$^{-1}$. A calibration curve was generated for concentrations from 1 nM-1 fM of the analyte, the cancer biomarker protein carcinoembryonic antigen (CEA),[21] spiked into serum. After tagging the protein microarray spots with SWNTs conjugated to the appropriate secondary antibody, Au seeds were deposited by precipitation of 5 mM of chloroauric acid. Subsequent reduction of the Au$^{3+}$ clusters by sodium borohydride yielded a pink-purple color on the substrate, indicating successful seeding of Au NPs onto the protein bioassay substrate. Soaking of the bioassay slide in hydroxylamine and chloroauric acid resulted in growth of a uniform Au/Au film.

Compared to previous methodologies utilized by our group for obtaining SERS of SWNT-labeled protein bioassays, the Au/Au films showed a marked improvement over vacuum deposited metal films with an enhancement factor up to ~250 fold for the SWNT Raman G-band (FIG. 4B). SERS enhancement of SWNTs on Au/Au films was compared with glass-only substrates and 5 nm silver-coated glass slide. a) Average G-band scattering intensities recorded following SWNT immunoassay of 1 nM CEA as described in FIG. 3. b) SWNT G-band Raman intensities following CEA immunoassay for Au/Au films (recorded at 8 mW) compared with 5 nm-silver on glass substrates (recorded at 20 mW). Note that the data are acquired from separate immunoassay experiments, which introduces slight sample-to-sample variation. c) AFM image of SWNTs immobilized onto a CEA immunoassay microarray spot before deposition of the Au/Au film, and d) SEM image of the immunoassay spot after film deposition. The enhanced signal-to-noise ratio afforded a limit of detection of CEA down to ~5 fM (~1 pg/mL) (FIG. 4C: black squares) with 100 ms Raman scattering integration per pixel. Without Au/Au film enhancement, the detection limit was >10 pM (FIG. 4C: gray triangles).

Example 6: Methods and Materials Used for Preparing Plasmonic Substrates for Protein Microarrays Conjugation of IR800 to Goat Anti-Rabbit IgG IR800cw-NHS ester was dissolved in dry DMSO. IR800cw-NHS ester was mixed with goat anti-rabbit IgG in PBS at a 4:1 mole ratio and incubated in the dark at room temperature for 1 hr following excess removal by G-25 NAP-5 columns, resulting in a loading of ~1 dye/IgG.

Conjugation of IR800/Cy5 to Streptavidin

IRDye800-NHS ester or Cy5-NHS ester was dissolved in dry DMSO, then mixed with streptavidin in PBS at a 10:1 mole ratio and incubated in the dark at room temperature for 1 h following excess removal by G-25 NAP-5 columns, resulting in a loading of ~2 dyes per streptavidin according to the UV-Vis-NIR spectrum measured by a Cary 300 UV-Vis-NIR absorbance spectrometer.

Preparation of Gold-on Gold (Au/Au) Films

Gold-on-gold (Au/Au) films were prepared by immersing a glass slide into a solution of 3 mM $HAuCl_4$ (aq). 20 μL of $NH_4OH$ was added per mL of total volume with rapid shaking for one minute. The substrate was submerged in two clean water baths to remove unbound $Au^{3+}$ precipitate and then was immersed into 1 mM $NaBH_4$ for 1 minute, which completed the seeding step. After washing, the substrate was immersed into a 1:1 aqueous solution of $HAuCl_4$ and $NH_2OH$ (e.g. 750 μM) and uniformly shaken for five minutes, followed by a ten-minute incubation to complete the growth step. The substrate was washed again by immersion into water and blown dry. The plasmon resonance of the resulting Au/Au films was measured using a Cary 300 UV-vis-NIR absorbance spectrometer after correcting for background absorbance from the glass substrate. Scanning electron micrographs were acquired on an FEI XL30 Sirion SEM with FEG source at 5 kV acceleration voltage.

Attachment of 6PEG-COOH to Films and Microarray Printing

Au/Au substrates were immersed into 10 mM cysteamine in ethanol overnight at room temperature. After rinsing with ethanol and drying, the amine-functionalized Au/Au substrate was immersed in a solution of 20 μM 6-arm poly (ethylene glycol)-carboxylate ($M_n$~10,000 Da) and 20 mM each of 1-ethyl-3-(3-dimethylaminopropyl) carbodiimide and N-hydroxysuccinimide (NHS) in DMF. After rinsing the Au/Au substrate with ethanol and drying, NHS-activated Au/Au and bare glass substrates were loaded into a microarray printing robot where 5 uM monoclonal mouse anti-CEA IgG in PBS supplemented with 0.1% glycerol and 0.01% tween-20 was printed via solid pins at 25° C. and 65% humidity, resulting in microarray feature diameters of ~400 μm, printed into 12 sets of 12 spots. The slides were dried with compressed air and blocked shortly after printing. For preparation of autoantigen arrays, functionalized Au/Au films, glass slides and two-pad nitrocellulose slides were loaded into a microarray robot contact printer at 25° C. and 65% humidity. Autoantigens purchased from Diarect, Molecular Probes, Biodesign, Immunovision, or Sigma-Aldrich were printed in triplicate in PBS supplemented with 0.01% tween-20 and glycerol at the concentrations and in the order indicated in Table 1—Example 11.

Construction of Multilayer Surface Chemistry on Gold Film (Cytokine Assay)

Gold slides were immersed into 10 mM mercaptohexadecanoic acid in ethanol overnight at room temperature. After rinsing with ethanol and drying, the carboxylic group functionalized gold slide was immersed in a solution of 20 μM 6-arm poly (ethylene glycol)-amine ($M_n$~10,000 Da) and 20 mM each of 1-ethyl-3-(3-dimethylaminopropyl) carbodiimide and N-hydroxysuccinimide (NHS) in DMF. After rinsing the gold slide with DMF, ethanol and drying, the substrate was immersed in 10 mM succinic anhydride DMF solution with triethylamine at 1 μL per mL. This step transforms the free amine groups on the poly (ethylene glycol) chain into carboxylic groups. Following another washing step with DMF and ethanol, the slide was incubated in 20 mM each of 1-ethyl-3-(3-dimethylaminopropyl) carbodiimide and N-hydroxysuccinimide (NHS) in DMF to activate the carboxylic group.

Microarray CEA Sandwich Assay Procedure

Briefly, slides were blocked overnight at 4° C. in a solution containing 3% fetal bovine serum (FBS) in PBS containing 0.05% tween-20 (PBST). Purified carcinoembryonic antigen (CEA) was diluted into pure FBS and 20 μL of each CEA solution (CEA concentrations varied from 1 nM to 1 fM) was applied to each set of spots along with a control of only pure FBS (blank) and incubated 6 hours at room temperature, followed by washing. Polyclonal rabbit anti-CEA was incubated over each set of array spots at 10 nM in PBS and incubated at room temperature in a humid environment for 1.5 hours. Assays were again washed and 500 pM of Cy5 or IR800-conjugated polyclonal goat anti-rabbit IgG was incubated for ten minutes at room temperature. Assay substrates were washed three times in PBST and once in PBS, followed by immersion in deionized water and were subsequently blown dry with compressed air. When xenograft serum samples were to be included along with a calibration curve, purified CEA was diluted into 10% normal mouse serum supplemented with 3% FBS in PBS rather than pure FBS, and 2 μL of xenograft serum was diluted to 20 μL by 3% FBS in PBS. All other steps remain the same. The resulting 10-fold diluted xenograft CEA serum fluorescence intensities were compared to a sigmoidal fit of the accompanying calibration curve and then corrected for the 10-fold dilution to calculate the original serum concentration.

Microarray Cytokine Microarray Sandwich Assay Procedure

The NHS-activated gold slides above (or nitrocellulose slides) were loaded into a microarray printing robot where 5 μM monoclonal mouse anti human Cytokine IgG in PBS supplemented with 0.5% glycerol was printed using solid pins at 25° C. and 60% humidity, resulting in microarray feature diameters of ~400 μm, printed into 12 sets of 12 spots. The slides were dried in a desiccator and then blocked in PBST solution containing 3% fetal bovine serum. Cytokine antigen was diluted into PBST solution with 10% FBS, and 20 μL of each cytokine solution with concentrations varied from 1 nM to 1 fM was applied to each set of spots along with a blank control composed of 10% FBS in PBST, and incubated for 6 h at room temperature, followed by washing with PBST two times and PBS one time. Polyclonal goat anti-cytokine was then incubated over each set of array spots at 5 nM in PBST with 10% FBS for 1 h at room temperature, followed by washing in PBST twice and PBS once, and incubation in 1 nM IR800 conjugated streptavidin PBST solution with 10% FBS for 30 minutes at room temperature in the dark. Assays were washed two times in PBST and one time in PBS, followed by immersion in deionized water and subsequent drying with compressed air.

Multiplexed Autoantigen Microarray Assay Procedure

Autoantigen arrays (Table 1-Example 11) on µArray/Au, nitrocellulose, and Superfrost Plus glass substrates were blocked overnight at 4° C. in a solution containing 3% FBS in PBST. A equivolume mixture of reactive human sera (Immunovision, used as received) containing characterized autoantibodies against Smith antigen, SS-A antigen, centromere antigen, Ribosomal P antigen, histones, thyroglobulin, myeloperoxidase, proteinase 3, topoisomerase I, mitochondrial antigen, and Jo-1 (included at 0.75 equivalent fractional volume) was diluted 1:300 in 10% FBS and incubated on the autoantigen arrays for 3 hours at room temperature, followed by washing with PBST. Subsequently the array was probed with goat anti-human IgG secondary antibody labeled with IR800 at 1 nM (~1 dye/antibody) in 10% FBS in PBST for 10 minutes at room temperature. Assay substrates were washed three times in PBST and once in PBS, followed by immersion in deionized water and were subsequently blown dry with compressed air.

Multiplexed Antibody-Based Cytokine Microarray Assay Procedure

Instead of printing one type of capture antibody into 12 sets of 12 spots, 8 sets of 48 spots in a 6 rows×8 columns format was printed on NHS-activated gold film. The 8 spots contained in each of the 6 rows was composed of a cytokine-specific capture antibody. The slides were also dried in a desiccator and then blocked in PBST solution containing 3% fetal bovine serum. One cytokine or a mixture of cytokines in PBST with 10% FBS or cell culture medium was applied to each set of multiplexed matrix and incubated for 6 h at room temperature, followed by washing with PBST two times and PBS one time. A mixture of biotinylated polyclonal rabbit anti human VEGF, biotinylated polyclonal mouse anti human IL-1β, biotinylated polyclonal goat anti human IL-4, biotinylated polyclonal goat anti human IL-6, biotinylated polyclonal mouse anti human IFN-γ, polyclonal goat anti human TNF were incubated over each set of array spots at 5 nM each in PBST with 10% FBS for 1 h at room temperature, followed by washing in PBST twice and PBS once, and incubation in 1 nM IR800 conjugated Streptavidin PBST solution with 10% FBS for 30 minutes at room temperature in the dark. Assays were washed two times in PBST and one time in PBS, followed by immersion in deionized water and subsequent drying with compressed air.

Culture of SKOV-3 and OVCAR-3 Cells

SKOV-3 cells were cultured in McCoy's 5A Medium with L-glutamine, and OVCAR-3 cells were cultured in RPMI Medium 1640 with L-glutamine. Both culture media were supplemented with 10% fetal bovine serum, 100 IU·mL-1 penicillin and 100 µg/mL streptomycin. Cells were maintained in a 37° C. incubator with 5% CO2 for 48 hrs at 50-60% confluency, before the supernatant was sampled for microarray sensing. As a control, fresh cell medium without cells growing was also used for sensing.

Fluorescence Measurement and Analysis

A Horiba Jobin Yvon Labram HR800 confocal laser scanning microscope was used for the majority of fluorescence measurements presented herein. Horiba Jobin Yvon Labspec software, or occasionally GenePix 6.0 (Molecular Devices), was used to analyze and quantify fluorescence emission. Using Labspec, the average local background was subtracted and the average spectrum for each array feature or protein spot was averaged. Standard deviations represent the standard error of the means of twelve replicate spot features for each CEA concentration. Fluorescence was quantified by integrating the baseline-corrected, fluorescence emission peak (645 nm-740 nm for Cy5 and 790 nm-875 nm for IR800). The Molecular Devices Genepix 4000B Axon scanner and Licor Odyssey scanner were also used to verify compatibility of µArray/Au assays with commercial systems. Multiplexed autoantigen/autoantibody arrays were scanned using the Licor Odyssey Scanner, 800 nm channel with gain set to 6.0, 42 µm. Genepix 6.1 was used to automatically identify features above composite pixel intensity (CPI) of 5. Fluorescence intensities are the average of mean pixel intensity values for features printed in triplicate.

For fluorescenece detection in antibody-based cytokine microarray assays, the commercial Licor Odyssey scanner was applied on different substrates with the 800 nm channel and gain set to 6.0, 42 µm. Genepix 6.1 was used to automatically identify features above composite pixel intensity of 5. Fluorescence intensity for each set of features was the background corrected average of mean pixel intensity values for features printed in duplicates. Cytokine microarray with detection using secondary antibody labeled with Cy5 Dye were scanned with commercial Genepix 4000B scanner at 635 nm excitation with 33% laser power and PMT 550.

Fluorescence Lifetime Measurement

Fluorescence lifetimes of Cy5 and IR800 conjugated to IgG molecules were measured by time-correlated single photon counting (TCSPC). For sandwich assay lifetime measurements, a CEA sandwich assay was performed as described above on an Au/Au film, as well as on a borosilicate glass coverslip.

Xenograft Models and Animal Handling

Athymic nude female mice obtained from Charles River were housed at Stanford Research Animal Facility (RAF) under Stanford Institutional Animal Care and Use Committee (IACUC) protocols. When the mice reached 8 weeks in age, they were inoculated with approximately 2 million LS174T cells subcutaneously on the shoulder. At the given time points, ~100 µl of blood was collected from the tail of the mice. The blood was then centrifuged at 10,000 g for 20 minutes in order to fractionate the blood and collect the serum. During the tumor inoculation and blood collection, the mice were anesthesized by inhalation of 2% isoflurane mixed with oxygen accordingly to an approved animal protocol. The tumor width and length was measured using a digital caliper. The tumor volume was derived from the modified ellipsoidal formula: Volume=(Width×Width×Length)/2.

Materials

Superfrost Plus glass slides and quartz slides were purchased from Fisher Scientific and rinsed with acetone, IPA, and methanol prior to use. Epoxide-modified (SuperEpoxy2) glass slides were purchased from Arrayit. Two-pad Whatman FAST nitrocellulose slides, chloroauric acid trihydrate, hydroxylamine HCl, sodium borohydride, cysteamine, aminopropyltriethoxysilane (APTES), 1-ethyl-3-(3-dimethylaminopropyl) carbodiimide (EDC), and N-hydroxysuccinimide (NHS) were purchased from Sigma-Aldrich. Ammonium Hydroxide (30% ammonia) and Hyclone fetal bovine serum were purchased from Fisher Chemicals. Purified carcinoembryonic antigen (CEA) was purchased from R&D systems, monoclonal mouse anti-CEA (5910) was purchased from Medix Biochemica (Biospacific) and polyclonal rabbit anti-CEA (ab15987) was purchased from Abcam. Unmodified goat anti-rabbit IgG, as well as the Cy5-conjugate, and goat anti-human IgG were purchased from Jackson Immunoresearch. Autoantigens were purchased from Diarect, Molecular Probes, Biodesign, Immunovision, or Sigma-Aldrich. Autoimmune-reactive sera were purchased from Immunovision. IR800cw-NHS ester was purchased from Licor Biosciences. 6-armed poly(ethylene glycol)-amine was purchased from SunBio and converted to the carboxylate as described previously.[5] IR800cw has a reported free-space quantum yield between 7 and 12% with an inherent fluorescence lifetime between 0.9 and 1.3 nsec.[3] Cy5-conjugates have a reported free space quantum yield of ~20% and lifetime of ~1.5 nsec.

Purified cytokine antigen standards for VEGF, IL-1β, IL-4, IL-6, IFN-γ and TNF were purchased from R&D systems. Sandwich Antibody pairs for IL-1β, IL-4, IL-6, IFN-γ, and TNF were purchased from R&D systems. Sandwich antibody pairs for VEGF were purchased from Peprotech, Inc. Unmodified streptavidin was purchased from Jackson Immunoresearch.

Conjugation of IR800 to Goat Anti-Rabbit IgG and Goat Anti-Human IgG

IR800cw-NHS ester was dissolved in dry dimethylsulfoxide and the concentration was determined by UV-Vis-NIR absorbance spectroscopy ($\epsilon_{774}$~240,000 $M^{-1}cm^{-1}$). IR800cw-NHS ester was mixed with goat anti-rabbit IgG or goat anti-human IgG in PBS at a 4:1 mole ratio and incubated in the dark at room temperature for 1 hr. Free fluorophores were removed by size exclusion chromatography (Sephadex G-25 NAP-5 columns, GE Healthcare), resulting in a loading of ~1 dye/IgG. Specificity of the resulting goat anti-rabbit IgG-IR800 conjugate was tested by drop drying 0.5 µL of 1 µM rabbit anti-CEA IgG and mouse anti-CEA IgG onto an Au/Au film, blocking (as described below), and incubation of 500 pM of goat anti-rabbit IgG-IR800 for 10 minutes, followed by fluorescence intensity mapping.

CEA Sandwich Assay Procedure for all Substrates

Printed, dried sets of assay features (12 microarray spots per set) were circumscribed with hydrophobic marker (PAP pen) to create sample wells. µArray/Au slides were blocked overnight at 4° C. following microarray printing of IgG in 3% fetal bovine serum (FBS) in PBS containing 0.05% tween-20 (PBST), supplemented with 1 mg/mL thiol-terminated methoxy poly(ethylene glycol) ($M_n$~5000 Da) and 1 mM tris. Glass slides were blocked overnight at 4° C. following microarray printing in 3% FBS in PBST.

Purified carcinoembryonic antigen (CEA) was diluted into pure FBS at final concentrations ranging from 100 pM to 1 fM, and 20 µL of each CEA solution was applied to a sample "well" along with a control of only pure FBS (blank). Analyte was incubated at room temperature in a humid environment for six hours on an orbital shaker (100 RPM), followed by removal of the CEA sample solutions by micropipette, two immersions (5 mins each) in PBST, and a brief immersion in PBS. Polyclonal rabbit anti-CEA was applied to each sample "well" at 10 nM in PBS and incubated at room temperature in a humid environment for 1.5 hours on an orbital shaker. Assays were washed as above. 500 pM of Cy5 or IR800-conjugated polyclonal goat anti-rabbit IgG was incubated in each sample "well" for ten minutes at room temperature on an orbital shaker. Assay substrates were washed three times in PBST and once in PBS, followed by immersion in deionized water and was subsequently blown dry with compressed air. When xenograft serum samples were to be included along with a calibration curve, purified CEA was diluted into 10% normal mouse serum supplemented with 3% FBS in PBS rather than pure FBS, and 2 µL of xenograft serum was diluted to 20 µL by 3% FBS in PBS. All other steps remain the same.

Fluorescence Measurement and Analysis

A Horiba Jobin Yvon Labram HR800 confocal laser scanning microscope was used for the majority of fluorescence measurements presented herein. An 80 mW 785 nm diode laser or a 20 mW 633 nm HeNe laser were cleaned by band pass filters and passed through neutral density filters to control the laser power at the sample. For measurement of Cy5 fluorescence, the HeNe laser power was reduced 10-fold, while for IR800 fluorescence the diode laser power was reduced 100-fold. The incident beam was focused onto the sample in an epi-fluorescence configuration through a 100× (NA 0.9) air objective lens and raster scanned over a 5 µm×5 µm area during each spectral acquisition (Horiba Jobin Yvon Duoscan) and fluorescence was collected through the same objective and passed through a long pass, edge filter (~640 nm cutoff for Cy5 and ~790 nm for IR800). The excitation laser beam was scanned over the protein array or spot and the fluorescence peak integrated to generate fluorescence intensity maps.

Fluorescence spectral emission was collected by a TE-cooled silicon array with pixel binning of 2 and acquisition time of 10 msec.

Horiba Jobin Yvon Labspec software, or occasionally GenePix 6.0 (Molecular Devices), was used to analyze and quantify fluorescence emission. Using Labspec, the average local background was subtracted and the average spectrum for each array feature or protein spot was averaged. Fluorescence was quantified by integrating the baseline-corrected, fluorescence emission peak (645 nm-740 nm for Cy5 and 790 nm-875 nm for IR800). Error bars for microarray experiment measurements represent the standard deviation of the means of each of the twelve duplicate assay features. Using GenePix 6.0, the local background was subtracted, and the mean fluorescence intensity and mean fluorescence intensity over baseline was calculated using the algorithm described in the manufacturer's manual. Cy5-labeled µArray/Au assays probed using the Molecular Devices GenePix 4000B microarray scanner or IR800-labeled µArray/Au assays probed with the Licor Odyssey scanner yielded NIR-FE enhancements similar to those quantified on the Horiba Jobin Yvon HR800.

Fluorescence Lifetime Measurement

Fluorescence lifetimes of Cy5 conjugated to IgG molecules were measured by time-correlated single photon counting (TCSPC). For sandwich assay lifetime measurements, a CEA sandwich assay was performed as described above on an Au/Au film, as well as on a borosilicate glass coverslip. Excitation of the samples was provided by a pulsed diode laser (635 nm, PDL 800-B, PicoQuant) yielding pulse lengths of ~100 ps. The laser light was steered into the back-port of a Nikon TE300 microscope and focused with an oil objective (Plan Fluor 100×/1.3 NA, Nikon) to provide an average power of 0.1-1 kW $cm^{-2}$ at the sample plane. Back propagation of the sample fluorescence is collected with the same objective and passed through the following filters (Z710SPRDC dichroic, Z635RDC dichroic, HQ679/60M emission (Chroma), and $3^{RD}$650-710 emission, Omega Optical) and a 25 µm pinhole before being focused onto an APD (SPCM-ARQH-13, Perkin Elmer). TCSPC is achieved using the PicoHarp 300 TCSPC module (Picoquant). The excited state lifetime was extracted from the observed TCSPC histogram by fitting to a mono-exponential decay convolved with the instrument response function measured from scatter from a glass coverslip or Au/Au film that did not contain Cy5 fluorophores.

Example 7: Modification of Gold Solution Phase Films for Near-Infrared Fluorescence Enhancement Gold-on-gold films (Au/Au, referring to Au seeding followed by Au growth) were prepared on standard glass slides by a simple seeding and growth process in solution phase, producing elongated, tortuous nanoscale gold isolated island areas on glass with plasmon resonances in the near-infrared (FIG. 6A).

The gold seeding step was optimized to yield a dense and uniform distribution of Au nanoparticles on the substrate, and variation of the selective gold growth condition onto the gold seeds resulted in Au/Au films with a range of plasmonic resonances exhibiting monotonic red-shifting and increasing film thickness with increasing gold precursor concentrations (FIG. 8). Increasing Au/Au film thickness was accompanied by increasing gold island sizes and reduction in the density of inter-island gaps, followed by eventual coalescence of the gold isolated island areas into a continuous film (FIG. 9).

Enhanced fluorescence of fluorophores on Au/Au films was first gleaned by drop drying immunoglobulin G molecules (IgGs) conjugated to the near-infrared fluorescent dyes cyanine-5 (Cy5) and IR800 onto Au/Au films of various thicknesses, with a range of optical extinction maxima, as well as onto a bare glass slide. Integration of fluorescence resulted in a range of observed relative enhancement factors compared with the glass substrate, initially increasing with increasing film thickness to a maximum, followed by a decrease (FIG. 10). The ensemble fluorescence intensity likely reflects both quenching and enhancement effects, and it was experimentally determined that within the separation distance to the plasmonic film (~0-10 nm) provided by the size of the IgG molecule, Cy5 was maximally enhanced (~3-fold) by Au/Au films with a plasmon resonance peak of 575 nm while IR800 was maximally enhanced (~17-fold) by a slightly thicker film with a plasmon resonance peak of 610 nm (FIG. 6A). Aside from intensification, the emission maxima and spectral shape of both Cy5 and IR800 are unchanged during enhancement. Direct microarray printing of serially diluted dye labeled-IgGs onto optimized Au/Au films or glass slides revealed not only enhanced fluorescence intensity, but also a broadened dynamic range of detectable protein concentrations on Au/Au substrates over glass.

Example 8: NIR-FE Protein Microarray Assays on Au/Au Films Using Anti-CEA

With Au/Au film parameters optimized for NIR-FE of Cy5 and IR800 as described above, protein microarrays on Au/Au films (µArray/Au) were prepared by modifying the surface of the gold film with branched poly(ethylene glycol)-carboxylate (PEG-carboxylate), covalently conjugated to a thiol-containing cysteamine self-assembled monolayer (see Methods). This surface modification increases the hydrophilicity of the gold island film and reduces non-specific interaction of proteins with the gold surface while providing covalent coupling points for proteins via amidation. Monoclonal mouse anti-CEA (MaCEA) IgG was deposited robotically onto N-hydroxysuccinimide-activated PEG-carboxylate-coated Au/Au films, and on glass slides for comparison, by solid-pin contact printing at 5 µM (concentrations below 5 µM typically gave lower assay intensities, in microarray format. Capture antibody concentration dependence on Au/Au films was compared with glass slides. At low microarray printing concentrations very low fluorescence intensity was observed from the Au/Au substrate following a CEA sandwich assay as described in the main text, while higher printing concentrations increased the resulting signal intensity considerably. The same antibody printing concentration dependence was not observed for assays performed on glass.

Following a blocking step, CEA-spiked into pure fetal bovine serum was incubated above the MaCEA array features at concentrations ranging from 100 pM to 1 fM (1 fM=0.2 pg/mL) along with a serum-only blank (see Methods). Detection by polyclonal rabbit anti-CEA IgG (RaCEA) and subsequent labeling by goat anti-rabbit IgG (GaR) conjugated to IR800 demonstrated sensitivity over six orders of magnitude, down to a detection limit of ~5 fM, defined as blank plus three standard deviations (i.e. the standard error of the means of duplicate blank assay features). The resulting µArray/Au assay afforded a relative fluorescence enhancement of IR800 by up to ~100-fold compared to microarrays on glass substrates.

Identical CEA sandwich assays performed on branched PEG-carboxylate-modified glass slides and commercially available epoxide-functionalized glass slides showed slightly worse assay performance than unfunctionalized Superfrost Plus glass slides. CEA microarray on unmodified Superfrost Plus glass slides was compared with PEGylated-Superfrost Plus and Epoxide-modified (SuperEpoxy2, ArrayIt) glass slides. Superfrost Plus glass slides were soaked in 2% (v/v) APTES in ethanol overnight at room temperature to afford an amino-modified surface. Amidation of the amino-modified surface was accomplished by a 2 hr room temperature reaction with 6PEG-COOH via EDC/NHS in DMF, analogous to the amidation of cysteamine-modified Au/Au films described in the main text. Epoxide-glass slides were used as received. Mouse anti-CEA was microarray printed at 5 uM, followed by blocking, CEA incubation, binding of rabbit anti-CEA primary antibody, and finally binding goat anti-rabbit IgG IR800-conjugate. All of the microarrays processed on glass substrates, commercial or home-made, with various surface functionalization, were found inferior to µArray/Au, indicating that NIR-FE, and not surface chemistry, was the major cause of improved signal-to-noise and dynamic range of µArray/Au protein assays.

The ~100-fold increase in signal-to-noise afforded by µArray/Au improved the sensitivity of CEA detection in full serum by ~5000-fold relative to the glass substrate and afforded a broadened dynamic range of 6 orders of magnitude. In addition to IR800, Cy5-labeled µArray/Au assays also demonstrated relative fluorescence enhancements of ~15-fold (FIG. 11-12), affording a similar dynamic range and detection limit of CEA as the IR800-labeled µArray/Au assay.

Example 9: Variables in Obtaining Fluorescence Enhancement from µArray/Au

We investigated the origins of the observed increase in fluorescence intensity of both Cy5 and IR800 fluorophores on µArray/Au assays compared with those on glass. Sandwich assays, including protein microarrays, are inherently dependent on the quantity of antibody (or capture species)

immobilized onto the substrate. Scanning electron microscope (SEM) imaging revealed that the nano-island structure of Au/Au films afforded a ~70% increase in surface area compared with glass slides (FIG. 13), an insufficient difference to account for observed fluorescence enhancements from 15 to 100-fold.

We note that our nanostructured Au/Au films are unique over vapor phase deposited continuous Au films in affording high fluorescence enhancement. On continuous gold films, prepared by high vacuum electron beam evaporation methods, we found that fluorescence quenching, rather than enhancement was observed when protein sandwich assay experiments were performed.

Au/Au film plasmon resonance, gold island size and shape, and inter-island gap spacing were important variables in obtaining optimal fluorescence enhancement in protein microarray assays. SEM imaging revealed that Au/Au films optimal for NIR-FE possessed elongated gold nanoparticle isolated island areas with area ~14,000±11,500 $nm^2$ (i.e. about 2,000 to 30,000 $nm^2$), and small inter-island gap distances of 36±23 nm (i.e. about 10-60 nm), resulting in a broad surface plasmon resonance extending into the near-infrared. The necessity for optimal nanoscopic gold island sizes and small inter-island gaps is exemplified by the fact that thin Au/Au films containing small (~2,200±1,700 $nm^2$) gold isolated island areas (FIG. 9A), or thicker, semi-continuous (Au island size ~38,500±20,000 $nm^2$, FIG. 9C) and continuous (FIG. 9D) Au/Au films afforded little or no fluorescence enhancement for μArray/Au assays. The abundant nanoscale gaps in our optimal Au/Au films (FIG. 9B) could afford enhancement of local excitation electric fields, leading to increased excitation rates of fluorophores, thus contributing to the observed fluorescence enhancement in our microarrays.

We also measured the excited state lifetimes for fluorophores used in our μArray/Au sandwich assays by time-correlated single photon counting (see Methods). The quantum yield ($\eta$) of a fluorophore is defined by the ratio of the radiative decay rate ($k_{rad}$) to the total excited state decay rate, $\eta = k_{rad}/[k_{rad}+k_{nr}]$, where $k_{nr}$ is the non-radiative decay rate. Cy5-labeled CEA sandwich assays were used to probe the excited state lifetime of Cy5 on Au/Au films as well as on glass. A clear reduction in lifetime was observed, with the Cy5 fluorescence lifetime reduced to 0.32 nsec on a μArray/Au assay compared with its longer free space value of ~1.5 nsec.[22] It is possible that both electric field enhancement and increased radiative decay rate due to fluorophore coupling to the dipolar plasmonic modes in the underlying Au/Au film contributed to the observed increase in fluorescence quantum yield. However, further work is needed to discern changes in the radiative and non-radiative decay rates caused by coupling to the plasmonic modes in the nanostructured Au/Au film.

Example 10: μArray/Au Detection of Biomarkers in Xenograft Mouse Serum

To demonstrate the utility of NIR-FE protein microarrays, detection of serum cancer biomarkers was conducted by preparing mouse models bearing xenograft tumors of the LS174T colon cancer model, known to over-express and shed CEA into the bloodstream. Two million LS174T cells per xenograft were inoculated subcutaneously into athymic nude mice and allowed to grow over the course of three weeks. Blood samples were extracted from the tail before inoculation, as well as at several time points during the course of tumor growth, with serum samples isolated by centrifugation (see Methods). 10-fold dilution of just 2 μL of sample serum allowed quantification of serum CEA levels on μArray/Au against a standard curve, obtained with calibration spots (assay spots exposed to known CEA concentrations) on the same μArray/Au substrate. Two mouse models were prepared for this study, and their serum CEA levels were analyzed in separate experiments on μArray/Au assays labeled by IR800. In comparison to calibration curves, serum samples taken prior to inoculation of LS174T indicated no measurable CEA, however detectable levels of CEA were observed in both mice when the xenograft tumor volume reached ~30-50 $mm^3$.

We observed a clear increase in CEA serum concentration with increasing tumor volume. Sera sampled following LS174T inoculation yielded CEA blood pool concentrations ranging from ~30 fM up to 5 pM with tumor volumes ranging from ~35 $mm^3$ to 425 $mm^3$. Under the 10-fold serum sample dilution conditions used in our μArray/Au assays, all serum samples contained CEA at levels undetectable by conventional ELISA, which possesses a limit of detection between 1 and 5 pM. A plot of CEA serum concentrations versus tumor volume demonstrated an exponential growth behavior, suggesting that the mouse model serum CEA levels change rapidly during the initial phase of tumor growth.

Example 11: Multiplexed μArray/Au Assays for Autoantibody Detection

The multiplex capabilities and small sample volume requirements of planar protein microarrays afford a wealth of information regarding both proven and putative protein biomarkers. Autoantigen microarrays have demonstrated utility in proteomic analysis of various human autoimmune disease processes and led towards improved diagnostic tests and a greater understanding of the underlying disease pathophysiology. To explore the multiplex capabilities of μArray/Au assays, we printed a total of 32 analytes in triplicate, including human autoantigens and controls onto μArray/Au, commercial nitrocellulose, and glass substrates.

TABLE 1

μArray/Au arrays of analytes printed in triplicate onto μArray/Au

| Name | Print Conc. (mg/mL) | Print # | Alternative/Expanded Name | Related Disease(s) |
| --- | --- | --- | --- | --- |
| HIgG | 0.2 | 1 | human IgG mixture | print control |
| Ro 60/SS-A | 0.395 | 2 | Ro 60/SS-A, bovine, non-recombinant | Systemic Lupus Erythematosus (SLE), Sjogren Syndrome, Subacute Cutaneous LE |
| U1-A | 0.295 | 3 | U1—Small nuclear ribonucleoprotein complex A | Systemic Lupus Erythematosus (SLE), Mixed Connective Tissue Disease |

TABLE 1-continued

| | μArray/Au arrays of analytes printed in triplicate onto μArray/Au | | | |
|---|---|---|---|---|
| Name | Print Conc. (mg/mL) | Print # | Alternative/Expanded Name | Related Disease(s) |
| Ro 52/SSA | 0.55 | 4 | Ro/SS-A | Systemic Lupus Erythematosus (SLE), Sjogren Syndrome, Subacute Cutaneous LE |
| U1-68 | 0.25 | 5 | U1—Small nuclear ribonucleoprotein complex 68 kDa | Systemic Lupus Erythematosus (SLE), Mixed Connective Tissue Disease |
| La/SSB | 0.2 | 6 | | Systemic Lupus Erythematosus (SLE), Sjogren Syndrome, Subacute Cutaneous LE |
| PM/Scl 100 | 0.2 | 7 | PM/Scl complex 100 | Systemic sclerosis, Polymyositis and Dermatomyositis |
| U1-C | 0.375 | 8 | U1—Small nuclear ribonucleoprotein complex C | Systemic Lupus Erythematosus (SLE), Mixed Connective Tissue Disease |
| BB' | 0.2 | 9 | U1—Small nuclear ribonucleoprotein complex B/B' | Systemic Lupus Erythematosus (SLE), Mixed Connective Tissue Disease |
| genomic ds DNA | 1 | 10 | Double stranded DNA from salmon testes | Systemic Lupus Erythematosus (SLE) |
| plasmid dsDNA | 0.5 | 11 | Double stranded plasmid DNA | Systemic Lupus Erythematosus (SLE) |
| Jo-1 | 0.6 | 12 | Histidyl-tRNA synthetase | Polymyositis and Dermatomyositis, interstitial disease, arthritis, fevers |
| Ku | 0.475 | 13 | Ku—p70/p80 | Systemic Lupus Erythematosus (SLE) |
| PCNA | 0.345 | 14 | Proliferating Cell Nuclear Antigen | Systemic Lupus Erythematosus (SLE) (rare) |
| CENP B | 0.5 | 15 | Centromere Protein B | Systemic sclerosis |
| PL-12 | 0.2 | 16 | Alanyl-tRNA synthetase | Polymyositis and Dermatomyositis |
| TG | 0.25 | 17 | Thyroglobulin | Autoimmune Thyroiditis (e.g. Graves Disease, Hashimoto Thyroiditis) |
| TPO | 0.25 | 18 | Thyroperoxidase | Autoimmune Thyroiditis (e.g. Graves Disease, Hashimoto Thyroiditis) |
| Scl-70 (trunc) | 0.55 | 19 | DNA topoisomerase I - 70 kda truncated | Systemic sclerosis |
| GBM-undis. | 0.75 | 20 | Glomerular Basement Membrane - undissociated | Goodpasture Syndrome |
| Tissue Transglutaminase | 0.525 | 21 | tissue Transglutaminase expressed in baculovirus/Sf9 insect cells | Celiac Disease |
| GBM-dis. | 0.5 | 22 | Glomerular Basement Membrane - dissociated (epitope exposed) | Goodpasture Syndrome |
| Actin | 1 | 23 | Actin from rabbit muscle | Celiac Disease |
| Intrinsic Factor | 0.2 | 24 | | Pernicious Anemia |
| Mumps Ag | 1.13 | 25 | Mumps virus antigen - Enders Strain | Mumps |
| C1q | 0.55 | 26 | Complement C1q protein | Systemic Lupus Erythematosus (SLE) |
| Rubella Ag | 0.25 | 27 | Rubella Strain HPV-77 antigen | Rubella |
| Rubeola Ag | 4.69 | 28 | Edmonston Strain | Measles |
| PM/Scl 75 | 0.55 | 29 | PM/Scl complex 75 | Systemic sclerosis, Polymyositis and Dermatomyositis |
| Sm/RNP | 0.38 | 30 | Sm/RNP complex | Systemic Lupus Erythematosus (SLE), Mixed Connective Tissue Disease |
| HIgG | 1 | 31 | human IgG mixture | print control |
| HIgG | 1 | 32 | human IgG mixture | print control |

The resulting autoantigen array was incubated with a mixture of human sera, containing both characterized autoantibodies with reactivity towards several autoantigen targets as well as poorly characterized antibodies with unknown reactivities (see Methods), at 1:300 dilution, and probed with IR800-conjugated goat anti-human IgG. The arrays were scanned and analyzed using commercially available equipment and software (see Methods).

Figures 7A, 7B, 7C:
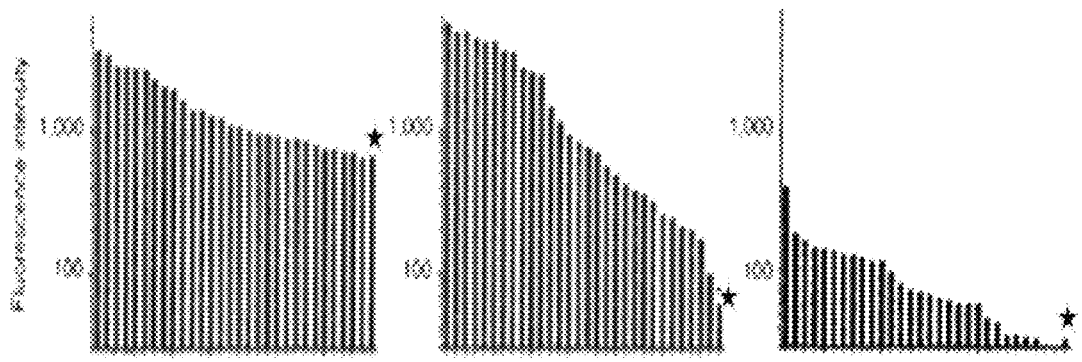
FIGS. 7A, 7B and 7C are bar graphs showing the log scale plot of mean pixel intensity of autoantigen/autoantibody arrays on nitrocellulose, µArray/Au, and glass, and average background (denoted by asterisk) for features printed in triplicate.

Compared to both highly porous nitrocellulose and planar glass substrates, our autoantigen μArray/Au afforded increased feature intensities owing to NIR-FE (FIG. 7) according to the intensity heatmap we obtained comparing the mean feature intensities of the same autoantigens on μArray/Au, nitrocellulose and glass. Notably, the high background intensity of nitrocellulose was a result of the combined effects of autofluorescence and non-specific binding. Background intensity of μArray/Au substrates and glass under 785 nm excitation were approximately 10-fold lower than nitrocellulose. On nitrocellulose films, the 32-autoantigen array showed intensities spanning merely half of an order of magnitude, while the same array formed on gold exhibited intensities spanning 2 orders of magnitude (FIG. 7). The autoantigen microarray intensities of μArray/Au were 25-50 times higher than on glass. Clearly, the NIR fluorescence enhancement and reduced background afforded by the multiplexed μArray/Au assay afforded increased sensitivity for autoantibody reactivity and broadened dynamic range (FIG. 7).

Good agreement in autoantigen-antibody reactivity was observed between the three assay substrates, however features on glass often failed to provide sufficient signal-to-background for quantification. The incubated serum mixture (see Methods) contained characterized human autoantibodies against SS-A, Jo-1, centromere protein B (CENP B), thyroglobulin (TG), and DNA topoisomerase-1 (scl-70, truncated fragment), all of which were detected with high intensity as expected on their conjugate antigen feature (Table 1). Several other autoantigen features on μArray/Au, but not on nitrocellulose or glass substrates, could be easily distinguished from background with significant signal-to-background ratios. The sera sample was not known or characterized to exhibit reactivity towards these autoantigens.

Example 12: Multiplexed μArray/Au Assays for Cytokine Detection

Chemical Modification of Plasmonic Gold Substrates for Cytokine Detection

A tortuous gold film comprised of gold nano-islands with abundant nanogaps was synthesized on glass slide using a solution phase method as described in Tabakman et al *Small*, referenced above, and in Section I hereof. The resulting gold film exhibited surface plasmon resonances in the NIR region, capable of enhancing the fluorescence intensity of several NIR fluorophores placed atop including IRDye800 and single-walled carbon nanotubes[36, 40-43]. For cytokine detection, we chemically modified the plasmonic gold film by covalently conjugating 6-arm branched poly(ethylene glycol) (PEG)-amine polymer stars to a self-assembled monolayer of mercaptohexadecanoic acid on the gold surface. The remaining free amine groups on the PEG star were converted to carboxylic acid groups through modification by succinic anhydride, and were subsequently activated through reaction with 1-Ethyl-3-(3-dimethylaminopropyl) carbodiimide (EDC) and N-hydroxysuccinimide (NHS), resulting in a layer of NHS groups for conjugating to the amine groups and immobilization of capture antibodies specific for cytokines (FIGS. 17A and 17B). This functionalization method was capable of efficient immobilization of capture antibodies while increasing the hydrophilicity of the plasmonic gold film through PEG-stars to minimize non-specific binding (NSB) effects. Enhancement of specific binding signals through a physical principle, i.e., plasmonic fluorescence enhancement and chemical minimization of background signals by PEG-star blocking of NSB are important factors contributing to sensitive cytokine detections.

Single Cytokine Detection with Femtomolar Sensitivity on Plasmonic Gold Substrates Cytokine measurement was performed using a 4-layer immunoassay approach (FIG. 17B). Referring now to FIG. 17B, capture antibodies (1902) specific for a human cytokine (VEGF, IL-1β, IL-4, IL-6, IFN-γ or TNF) were immobilized by contact printing onto a PEG-star coated plasmonic gold substrate through the formation of covalent amide bonds between amine groups on the capture antibodies and EDC/NHS activated carboxylic acid group on the PEG-stars. A blocking step was added by treating the substrate with a fetal bovine serum (FBS) solution in PBS solution. Second, the substrate was exposed to PBS solutions containing 10% FBS and serially diluted cytokine in 1 fM-1 nM concentration range together with a blank control. For the third and fourth layers, biotin conjugated antibodies (1906) specific for the cytokine was incubated followed by incubation with IRDye800 labeled streptavidin (1908). Fluorescence detection of IRDye800 was then performed using a commercial scanner (Online Methods). For each of the VEGF, IL-1β, IL-4, IL-6, IFN-γ and TNF cytokines, we observed a dynamic range >5 orders of magnitude with excellent linearity. Cytokine measurement reached down to ~1 pg/ml detection limit defined as the concentration corresponding to the blank signal plus two standard deviations.

The same assays were performed on commercial nitrocellulose slides and glass slides to compare with the plasmonic gold substrate. Owing to higher fluorescence of the IRDye800 by up to ~100-fold, cytokine assays on gold afforded 2-3 order broader dynamic range compared to assays on glass. Nitrocellulose has been the substrate of choice for biological assays due to high surface area and porous structures, affording higher protein immobilization and binding capacity and thus increasing signal intensities. However, the relatively high background on nitrocellulose caused by autofluorescence of nitrocellulose and the lack of chemistry for blocking nonspecific binding limited the dynamic range and sensitivity of cytokine detection. Notably, switching from the widely used Cy5 dye to IRDye800 for fluorescence labeling of cytokines on nitrocellulose improved the sensitivity by nearly an order of magnitude due to reduced autofluorescence in the NIR region. However, the detection sensitivity for cytokine was still at least an order of magnitude lower than on the plasmonic gold substrate.

Cytokine assays on plasmonic Au substrates were about an order of magnitude more sensitive than ELISA data provided by the ELISA kit manufacturer (Table 2). Nevertheless, we performed our own ELISA measurements in parallel with the assay on gold using the same reagents for each cytokine and obtained somewhat lower sensitivity for ELISA than data provided by the manufacturer (Table 2).

TABLE 2

Detection limit of cytokine sensing through different approaches

| Cytokine | ELISA sensitivity (pg/ml) | Nitrocellulose sensitivity (pg/ml) | Plasmonic gold slide sensitivity (pg/ml) | Glass slide sensitivity (pg/ml) |
| --- | --- | --- | --- | --- |
| VEGF | 100 (vendor) 331 (this work) | 91 | 4.8 | 192 |
| IL-1β | 1 (vendor) 4 (this work) | 0.8 | 0.07 | 9 |
| IL-4 | 10 (vendor) 29 (this work) | 7 | 1.3 | 52 |
| IL-6 | 0.7 (vendor) 19 (this work) | 2.3 | 0.06 | 10 |
| IFN-γ | 8 (vendor) 36 (this work) | 3.2 | 0.25 | 27 |
| TNF | 4.4 | 3.7 | 0.47 | 41 |

Multiplexed Cytokine Detection on Plasmonic Au Substrates

Figure 18A:
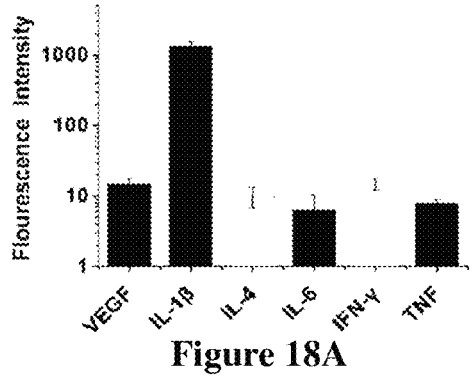
FIG. 18A-D shows results for a multiplexed cytokine assay.
Figure 18B:
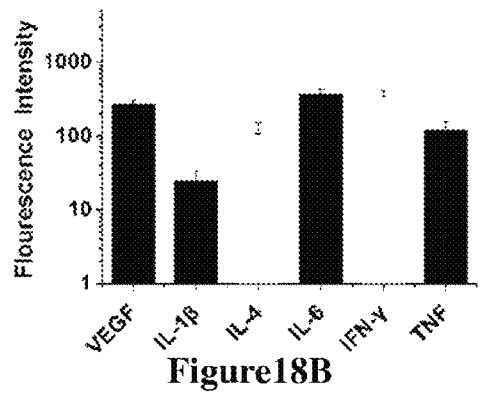
Figure 18C:
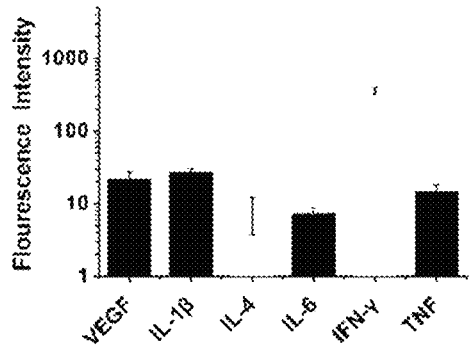
Figure 18D:
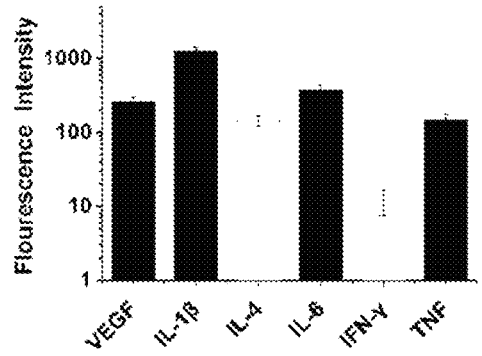

To demonstrate specificity of the multiplexed cytokine array, solutions containing a single cytokine were first measured at the ~10 pg/ml (1 pM) level (near the detection limit of ELISA). Only the corresponding row of the microarray showed bright fluorescence signal (data not shown) after exposure to the cytokine, a mixture of all six biotinylated detection antibodies and IRDye800 labeled streptavidin. Fluorescence images of spots from an array showed clear fluorescent signals when a multiplexed antibody chip (6 rows, 6 different antibodies against cytokines labeled at the left of the image) was incubated in a solution containing the corresponding cytokine at 1 pM (10 pM for VEGF) without any other cytokines. Also, the same multiplexed antibody array showed 5 brightly fluorescent rows with one dark row after the array was incubated in a solution containing corresponding 5 cytokines at 1 pM (10 pM for VEGF) to the bright rows. FIG. 18A shows the averaged fluorescence intensity over spots in each row of capture antibodies when only IL-1β was incubated on the antibody microarray at 1 pM. FIG. 18B shows the averaged fluorescence over spots in each row when a cocktail (without IL-1β) of VEGF, IL-4, IL-6, IFN-γ, and TNF were incubated on the microarray at 1 pM each (10 pM for VEGF). FIG. 18C shows averaged fluorescence intensity over spots in each row of capture antibodies when only IFN-γ was incubated on the antibody microarray at 1 pM. FIG. 18D shows averaged fluorescence over spots in each row when a cocktail (without IFN-γ) of VEGF, IL-1β, IL-4, IL-6, TNF were incubated on the microarray at 1 pM each (10 pM for VEGF).

This clearly suggested high specificity of the array. A high positive to negative signal ratio of 10-100 at ~10 pg/ml (1 pM) cytokine concentration (FIG. 18A and FIG. 18C) were measured, outperforming on nitrocellulose or glass slides where positive signals were only slightly higher than the negative signal or the background level.

An additional specificity test was performed by incubation of the multiplexed microarrays on gold to a mixture of five cytokines spiked into 10% FBS/PBS with the sixth cytokine excluded. In this case, five rows of the spotted capture antibodies exhibited bright fluorescent spots with one missing row corresponding to the excluded sixth cytokine. These results clearly demonstrated the capability of performing cytokine assays on plasmonic gold substrates in a multiplexed format with high specificity Multiplexed Cytokine Detection in Cancer Cell Culture Media To demonstrate the utility of cytokine assays on plasmonic gold substrates, we measured cytokine expression levels in conditioned media collected from the culture medium of several cancer cell lines. The ovarian cancer OVCAR3 cell line was cultured for 48 hours, after which the cell culture medium was collected, and the concentration of each secreted cytokine was measured with an antibody-based cytokine microarray on a plasmonic gold slide against calibration curve for each cytokine spiked into fresh cell medium in 100 pM-1 pM concentrations.

Out of the 6 cytokines, VEGF, IL-6 and TNF were clearly detected in the OVCAR3 cell conditioned medium compared to fresh cell medium as blank control. Concentrations of the 3 cytokines were ~770 pg/ml (40 pM) for VEGF, ~510 pg/ml (25 pM) for IL-6 and ~32 pg/ml (1.8 pM) for TNF based on calibration curves simultaneously obtained on the same chip. Detection of cytokine expression levels in the cell culture medium from the ovarian cancer SKOV3 cell line were also performed in a similar manner. In this case, only VEGF and IL-6 expressions were detected at ~1030 pg/ml (53 pM) and ~890 pg/ml (44 pM) respectively.

Microarrays on nitrocellulose slides and glass were also constructed for cytokine detection in cell media. Compared to the arrays on plasmonic gold substrate, the background intensity on nitrocellulose was higher, and the spots corresponding to fresh medium negative control showed non-specific signals higher than the background. Due to the low signals on glass slides, only IL-6 can be quantitatively measured in the cell media.

Serum Cytokine Profiling for Inflammatory Disease Patients

Cytokines regulate many inflammatory processes involved in the pathogenesis of inflammatory diseases and autoimmune diseases. Imbalance between pro- and anti-inflammatory cytokines plays a key role in autoimmunity and chronic inflammation[44]. Knowledge of cytokine levels in human serum will help greatly in the investigation and treatment of various human diseases. ELISA, the current gold-standard method, has been widely applied for measurement of cytokines in disease research and clinical diagnosis. However, ELISA lacks the capability to detect multiple analytes in the same assay and requires a large amount of human serum. The sample required for ELISA is typically ≥50 μl, making it impractical for measurement of multiple cytokines in the serum of a patient. Moreover, the sensitivity of ELISA for cytokine measurement is limited to the pg/ml range, incapable of quantifying cytokine concentration below that level.

To attain the goal of multiplexed cytokine detection of human serum with pg/ml to sub-pg/ml sensitivity, we extended our cytokine microarrays on plasmonic substrate to measuring complex human samples. 20 human serum samples from 17 patients in three different disease categories plus healthy controls were analyzed for cytokine expression level. These patients were divided into 4 groups: rheumatoid arthritis (patient RA #1, RA #1-2, RA #2, RA #3 and RA #4, where RA #1 and RA #1-2 were sera taken from the same rheumatoid arthritis patient at different times. This nomenclature also applies to the description of MCTD and gout patient groups); mixed connective tissue disease (patient MCTD #1, MCTD #1-2, MCTD #2, MCTD #3 and MCTD #4); gout (patient Gout #1, Gout #1-2, Gout #2, Gout #3 and Gout #4); and healthy control (patient Control #1, Control #2, Control #3, Control #4 and Control #5).

Six inflammatory disease related cytokines were detected simultaneously with pg/ml to sub-pg/ml sensitivity using only 20 μl of serum per patient. Cytokine levels were analyzed by converting fluorescence intensity of spots on the microarray to concentration using the calibration curves based on serial dilutions of a mixture of six cytokine standards in bulk human serum. VEGF is a potent stimulating factor for angiogenesis and vascular permeability and plays important roles in inflammatory diseases[45]. We observed higher VEGF levels (several hundred pg/ml) in serum samples from all three groups of inflammatory disease patients compared to healthy controls (p<0.05). IL-1β, IL-6, IFN-γ and TNF are hallmark pro-inflammatory cytokines involved in the pathogenesis of inflammatory processes[44,46], and we observed a range of expression levels for these cytokines in patients' sera from hundreds of pg/ml to <10 pg/ml. IL-4 has various biological effects, depending upon the context of its expression, and has been implicated in inflammatory diseases[47-48]. The outcome of IL-4 detection on plasmonic slides demonstrated a higher level of IL-4 in inflammatory patients relative to healthy controls, especially for most of the rheumatoid arthritis patients, with IL-4 levels at thousands/hundreds of pg/ml range. These cytokine levels were in similar ranges measured previously by ELISA in non-multiplexed fashions[49-54], establishing high-throughput cytokine sensing on plasmonic gold slides with pg/ml sensitivity in a dynamic range of 1 pg/ml-$10^4$ pg/ml.

The patient samples were also profiled with Luminex xMAP. We detected similar levels of IL-1β, IFN-γ and TNF as with plasmonic substrate supported microarrays. However, the Luminex xMAP barely detected any IL-6 in most of the human sera, which was quantified at a range of sub-pg/ml to several hundred pg/ml by microarrays on gold (Table 3). Moreover, thousands of pg/ml levels of IL-4 in RA patient sera were observed on gold based microarrays, much higher than tens of pg/ml IL-4 level measured by Luminex xMAP. To validate the measurements, we performed ELISA measurements with the RA patient sera for IL-4 level, and observed high levels of IL-4 in accordance with the gold microarray data. We also quantified VEGF levels by the gold microarray approach for patients with inflammatory diseases, with the measured concentrations higher than those measured by Luminex xMAP (Table 3).

TABLE 3

Result for multiplexed cytokine measurements in the sera of patients with rheumatoid arthritis, mixed connective tissue disease, gout diseases and health control by Luminex xMAP.

| Disease type | Patient # | VEGF | IL-1β | IL-4 | IL-6 | IFN-γ | TNF |
|---|---|---|---|---|---|---|---|
| RA | RA #1 | 62.24 | 18.42 | 38.93 | N.D. | 104.6 | 25.99 |
| RA | RA #1-2 | 68.04 | 24.96 | 42.54 | N.D. | 103.26 | 33.21 |
| RA | RA #2 | 91.67 | 5.95 | 21.79 | 9.7 | 123.43 | 17 |
| RA | RA #3 | 34.47 | 29.49 | 61.36 | N.D. | 81.19 | 38.93 |
| RA | RA #4 | 13.04 | N.D. | 5.48 | N.D. | 13.56 | 0.45 |
| MCTD | MCTD #1 | 47.93 | 2.49 | 2.72 | 1.66 | 17.55 | 2.85 |
| MCTD | MCTD #1-2 | 44.68 | 2.41 | 3.47 | 2.07 | 16.17 | 3.64 |
| MCTD | MCTD #2 | 45.29 | 2.07 | 5.48 | N.D. | 12.07 | 3.72 |
| MCTD | MCTD #3 | 12.14 | 1.48 | 2.6 | 9.56 | 12.31 | 1.2 |
| MCTD | MCTD #4 | 20.32 | 1.67 | 6.75 | N.D. | 14.08 | 2.39 |
| Gout | Gout #1 | 110.45 | 4.1 | 5.82 | 16.34 | 35.21 | 2.4 |
| Gout | Gout #1-2 | 142.77 | 4.35 | 7.98 | N.D. | 26.26 | 3.16 |
| Gout | Gout #2 | 69.09 | 3.78 | 9.29 | N.D. | 24.21 | 4.55 |
| Gout | Gout #3 | 240.27 | 5.06 | 9.87 | N.D. | 33.7 | 3.03 |
| Gout | Gout #4 | 39.94 | 2.48 | 5.87 | N.D. | 26.81 | 1.29 |
| Healthy | Control #1 | N.D. | N.D. | N.D. | N.D. | N.D. | N.D. |
| Healthy | Control #2 | 0.28 | N.D. | N.D. | N.D. | N.D. | N.D. |
| Healthy | Control #3 | 26.39 | 1.99 | 5.78 | N.D. | 15.16 | 4.47 |
| Healthy | Control #4 | 8.98 | 1.3 | 3.01 | N.D. | 6.73 | 2.16 |
| Healthy | Control #5 | 21.17 | 1.43 | 3.57 | N.D. | 7.67 | 3.06 |

N.D. means non-detectable and the data is in unit of pg/ml.

The present multiplexed cytokine and chemokine measurements using plasmonic gold slides are applicable to the field of autoimmunity. Diseases such as rheumatoid arthritis, juvenile idiopathic arthritis, ankylosing spondylitis and inflammatory bowel disease are driven in part by cytokines such as TNF, IL-1, and IL-6, whose inhibition using monoclonal antibody therpaeutics is highly efficacious. Multiplexed cytokine measurements have already been reported in RA using less-sensitive methods, identifying signatures associated with disease severity[55]. Another autoimmune disease, systemic lupus erythematosus, is characterized by high levels of many different cytokines and chemokines that are themselves induced by the inflammatory cytokine interferon alpha[56]. Accurate measurement of only 3 of these chemokines has been shown to correlate with disease severity and flares[57]. Finally, multiple sclerosis is treated with the anti-viral cytokine beta interferon, and it has been shown recently that patients who fail to respond to interferon have elevated levels of several other inflammatory cytokines, including interleukin-17F[58]. Taken together, it should be evident that plasmonic gold array methodology is well suited to measure multiple cytokines and chemokines in diseases that are driven by such molecules.

Example 13: Detection of Diagnostic Biomarkers of Type 1 Diabetes and Related Autoimmune Diseases This example employs protein microarray printing onto a gold plasmonic substrate on a glass chip as described in the examples above. This array allows detection of autoantibodies in a patient sample. The antibodies associated with diabetes type I are raised against small volumes of antigen. The present array and use of the plasmonic substrate with enhanced near-infrared fluorescence provides significantly improved sensitivity, as the gold film amplifies the fluorescent signal labels on detection antibodies. Additionally, this platform allows for multiplexed testing for more than one diabetes autoantibody from a single patient sample, in addition to testing for diagnostic autoantibodies for other autoimmune diseases known to have increased prevalence in patients with type 1 diabetes from the same sample (including celiac disease, autoimmune hypothyroidism, and Addison disease).

Three diabetes autoantibodies are detected, based on the antigens ICA512, Insulin and GAD65. Autoantibodies to insulin and GAD 65 were detected in test subjects and the results confirmed by RIA.

Example 14: Preparation of Au/Au Films from Solution Phase for Cell Imaging

The solution-phase Au/Au film synthesis was done as described in the examples above. Briefly, the substrates of quartz slides were immersed in a 3 mM solution of chloroauric acid, to which ammonia was added to reach 0.6 wt % under vigorous agitation. The quartz substrates were allowed to sit in the seeding solution with gentle shaking for 1 min, after which the substrates were washed with water. Then the substrates were submerged into a 1 mM solution of sodium borohydride on an orbital shaker at 100 rpm for 5 min. Following a second wash step for the substrates from the sodium borohydride solution, the seeded substrates were soaked in different growth solutions of 1:1 chloroauric acid and hydroxylamine at four different fixed concentrations: 250 μM, 500 μM, 1000 μM and 3000 μM under agitation for 15 minutes. Au/Au substrates were rinsed with water and dried with air. The ability of the various Au/Au substrates to enhance the fluorescence of SWNTs and IR800 were determined to give the optimized enhancing substrate, which was the one grown in 3000 μM chloroauric acid and hydroxylamine at a 1:1 molar ratio. Unless otherwise specified, all near-infrared fluorescence enhanced (NIR-FE) cell imaging was carried out on this substrate.

Scanning Electron Microscopy (SEM) Imaging of Au/Au Film on Quartz

Au/Au film grown on quartz was imaged via SEM. Image was acquired on an FEI XL30 Sirion SEM with FEG source at 5 kV acceleration voltage. False color was added using MATLAB software.

UV-Vis-NIR Extinction Measurements

UV-Vis-NIR extinction curve of Au/Au film was measured by a Cary 6000i UV-Vis-NIR spectrophotometer, background-corrected for any quartz contribution.

Example 15: Preparation of Water Soluble SWNT-IR800-RGD Bioconjugate Used in Cell Imaging The preparation of water soluble SWNT fluorophores can be found in detail in S. M. Tabakman, K. Welsher, G. S. Hong, H. J. Dai, *J. Phys. Chem. C* 2010, 114, 19569. Generally, raw HiPC® SWNTs (Unidym) were suspended in 1 wt % sodium deoxycholate aqueous solution by 1 hour of bath sonication. This suspension was ultracentrifuged at 300,000 g to remove the bundles and other large aggregates. The supernatant was concentrated and then layered to the top of a 10 wt %/20 wt %/30 wt %/40 wt % sucrose step gradient, followed by ultracentrifugation at 300,000 g for 1 hour. Only the top 1 mL was retained by careful fractionation and 0.75 mg/mL of C18-PMH-mPEG(90 k) (poly(maleic anhydride-alt-1-octadecene)-methoxy (polyethyleneglycol)90,000), synthesized by our group) along with 0.25 mg/mL of DSPE-PEG(5 k)-NH$_2$ (1,2-distearoyl-sn-glycero-3-phosphoethanolamine-N-[amino (polyethyleneglycol)5,000], Laysan Bio) was added. The resulting suspension was sonicated briefly for 5 min and then dialyzed against a 3500 Da membrane (Fisher) with a minimum of six water changes and a minimum of two hours between water changes. To remove aggregates, the suspension was ultracentrifuged again for 1 hour at 300,000 g. This surfactant-exchanged SWNT sample has lengths ranging from 100 nm up to 3.0 μm, with the average length of ~1 μm.

These amino-functionalized SWNTs were further conjugated with IR800 dye molecule and RGD peptide according to the protocol that described in Z. Liu, S. M. Tabakman, Z. Chen, H. J. Dai, *Nat. Protoc.* 2009, 4, 1372. Briefly, an SWNT solution with amine functionality at 300 nM after removal of excess surfactant, was mixed with 0.1 mM IR800 and 1 mM sulfo-SMCC at pH 7.4 for 2 h in PBS. After removing excess sulfo-SMCC by filtration through 100-kDa filters (Amicon), RGD-SH (cyclo-RGDFC, Peptides International) was added together with tris(2-carboxyethyl)phosphine (TCEP) at pH 7.4. The final concentration of SWNT, RGD-SH and TCEP were 300 nM, 0.1 mM and 1 mM, respectively. The reaction was allowed to proceed for 2 days before purification to remove excess RGD and TCEP by filtration through 100-kDa filters.

Atomic Force Microscopy (AFM) Imaging of SWNT-IR800-RGD Bioconjugate

AFM image of the as-made SWNT conjugate was acquired with a Nanoscope Ma multimode instrument in the tapping mode. The sample for imaging was prepared by soaking the SiO$_2$/silicon substrate in the SWNT-IR800-RGD conjugate suspension for 30 seconds, followed by rinsing with water and isopropanol, blow-drying and calcination.

Photoluminescence Versus Excitation Spectra (PLE) of SWNT-IR800-RGD Conjugate on Different Substrates PLE spectra were taken using a home-built NIR spectroscopy setup. The excitation source was a 150 W ozone-free Xenon lamp (Oriel), which was dispersed by a monochromator (Oriel) to generate excitation lines with a bandwidth of 15 nm. The excitation light in the range of 550-840 nm was focused onto two samples, SWNT-IR800-RGD drop-dried on Au/Au film and on quartz, and emission was collected in a 90-degree reflection geometry. The excitation light was rejected using a 900-nm long-pass filter (Thorlabs) so that the fluorescence of both IR800 and SWNTs could be collected in the 900-1500 nm emission range. The emitted light was directed into a spectrometer (Acton SP2300i) equipped with a liquid-nitrogen-cooled InGaAs linear array detector (Princeton OMA-V). Spectra were corrected post-collection to account for the sensitivity of the detector, extinction feature of the filter and the power of the excitation using the MATLAB software.

Example 16: Cell Incubation and Staining

All culture media were supplemented with 10% fetal bovine serum, 100 IU·mL$^{-1}$ penicillin, 100 μg·mL$^{-1}$ streptomycin and L-glutamine. U87-MG cells were cultured in Low Glucose Dulbecco's Modified Eagle Medium (DMEM), with 1 g·L$^{-1}$ D-glucose and 110 mg·L$^{-1}$ sodium pyruvate. MCF-7 cells were cultured in High Glucose DMEM, with 4.5 g·L$^{-1}$ D-glucose and 110 mg·L$^{-1}$ sodium pyruvate. Cells were maintained in a 37° C. incubator with 5% CO$_2$. For cell staining experiments, cells were trypsinized before the as-made SWNT-IR800-RGD conjugate was incubated with both α$_v$β$_3$-positive (U87-MG) and α$_v$β$_3$-negative (MCF-7) cell lines at a series of concentrations (30 nM, 6 nM, 1.2 nM, 240 pM and 48 pM) at 4° C. for 1 h, followed by washing the cells with 1×PBS to remove all free conjugates in the suspension. Then the cells were kept at 4° C. to prevent endocytosis before being imaged. Note that for control experiment, cells were stained at 37° C. for 1 h instead, also followed by washing the cells with 1×PBS to remove all free conjugates in the suspension.

Example 17: High-Magnification NIR Photoluminescence Imaging of Cancer Cells

Targeted cell imaging in the NIR II window (1100-1700 nm, i.e., SWNT fluorescence window) was done using a 658-nm laser diode with a 150 μm diameter spot focused by a 50× objective lens (Olympus) to get decent number of cells while not losing spatial resolution. The resulting NIR photoluminescence was collected using a liquid-nitrogen-cooled, 320×256 pixel, two-dimensional InGaAs camera (Princeton Instruments) with a sensitivity ranging from 800 to 1,700 nm. The excitation light was filtered out using an 1100 nm long-pass filter (Thorlabs) so that the intensity of each pixel represented light in the 1,100-1,700 nm range. The exposure time could be as short as 300 ms for the positive U87-MG cells stained at 30 nM and 6 nM on Au/Au film; while for all images taken on quartz or at lower staining concentrations, longer exposure of up to 3 s was needed to obtain images with comparable quality. After images were taken, they were flat-field-corrected to account for non-uniform laser excitation. On the other hand, targeted cell imaging in the NIR I window (800-1100 nm, i.e., IR800 fluorescence window) was taken with a Horiba Labram HR800 equipped with a 300 line/mm grating set to pixel binning of 3, with 0.8 mW (1% power) 785 nm excitation laser, through a ×50 long working distance objective lens. Emission was collected in the range of 790-820 nm using a band-rejection 785 nm filter. Exposure time was 0.05 s with no iteration. Mapping of the cells was carried out by taking 2 μm steps, and based on the baseline-corrected fluorescence intensity. Average fluorescence intensity in each stained cell was analyzed using the roipolyarray function in Matlab.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

1. G. C. Schatz, M. A. Young, R. P. V. Duyne, *Physics* 2006, 46, 19.
2. S. M. Nie, S. R. Emery, *Science* 1997, 275, 1102.
3. C. R. Yonzon, C. L. Haynes, X. Y. Zhang, J. T. Walsh, R. P. Van Duyne, *Analytical Chemistry* 2004, 76, 78.
4. Y. W. C. Cao, R. C. Jin, C. A. Mirkin, *Science* 2002, 297, 1536.
5. J. M. Sylvia, J. A. Janni, J. D. Klein, K. M. Spencer, *Analytical chemistry* 2000, 72, 5834.
6. Q. Zhou, Y. Yang, J. E. Ni, Z. C. Li, Z. J. Zhang, *Nano Research* 2010, 3, 423.
7. Z. Chen, S. M. Tabakman, A. P. Goodwin, M. G. Kattah, D. Daranciang, X. R. Wang, G. Y. Zhang, X. L. Li, Z. Liu, P. J. Utz, K. L. Jiang, S. S. Fan, H. J. Dai, *Nature Biotechnology* 2008, 26, 1285.
8. J. C. Hulteen, V. R. P. Duyne, *Vacuum Sci. Tech. A* 1995, 13, 1553.
9. C. J. L. Constantino, T. Lemma, P. A. Antunes, R. Aroca, *Analytical Chemistry* 2001, 73, 3674.
10. A. Tao, F. Kim, C. Hess, J. Goldberger, R. R. He, Y. G. Sun, Y. N. Xia, P. D. Yang, *Nano Lett* 2003, 3 pp, 1229.
11. R. G. Freeman, K. C. Grabar, K. J. Allison, R. M. Bright, J. A. Davis, A. P. Guthrie, M. B. Hommer, M. A. Jackson, P. C. Smith, D. G. Walter, M. J. Natan, *Science* 1995, 267, 1629.
12. G. Chumanov, K. Sokolov, B. W. Gregory, T. M. Cotton, *Journal of Physical Chemistry* 1995, 99, 9466.
13. S. B. Chaney, S. Shanmukh, R. A. Dluhy, Y. P. Zhao, *Applied Physics Letters* 2005, 87, 031908.
14. J. Neddersen, G. Chumanov, T. M. Cotton, *Appl. Spectrosc.* 1993, 47, 1959.
15. J. B. Jackson, N. J. Halas, *Proceedings of the National Academy of Sciences of the United States of America* 2004, 101, 17930.
16. L. Au, Y. C. Chen, F. Zhou, P. H. C. Camargo, B. Lim, Z. Y. Li, D. S. Ginger, Y. A. Xia, *Nano Research* 2008, 1, 441.
17. F. Ni, T. M. Cotton, *Analytical Chemistry* 1986, 58, 3159.
18. K. R. Brown, L. A. Lyon, A. P. Fox, B. B. Reiss, M. J. Natan, *Chemistry of Materials* 2000, 12, 314.
19. L. Supriya, R. O. Claus, *Langmuir* 2004, 20, 8870.
20. P. Schuck, D. Fromm, a. Sundaramurthy, G. Kino, W. Moerner, *Physical Review Letters* 2005, 94, 14.
21. I. Chau, M. J. Allen, D. Cunningham, A. R. Norman, G. Brown, H. E. R. Ford, N. Tebbutt, D. Tait, M. Hill, P. J. Ross, J. Oates, *Journal of Clinical Oncology* 2004, 22, 1420.
22. F. Somodi, I. Borbath, M. Hegedus, A. Tompos, I. E. Sajo, A. Szegedi, S. Rojas, J. L. G. Fierro, J. L. Margitfalvi, *Applied Catalysis a-General* 2008, 347, 216.
23. B. Bronnum, H. S. Johansen, L. H. Skibsted, *Inorganic Chemistry* 1988, 27, 1859.
24. B. E. Baker, N. J. Kline, P. J. Treado, M. J. Natan, *Journal of the American Chemical Society* 1996, 118, 8721.
25. N. Felidj, J. Aubard, G. Levi, J. R. Krenn, A. Hohenau, G. Schider, A. Leitner, F. R. Aussenegg, *Applied Physics Letters* 2003, 82, 3095.
26. J. P. Camden, J. A. Dieringer, Y. M. Wang, D. J. Masiello, L. D. Marks, G. C. Schatz, R. P. Van Duyne, *Journal of the American Chemical Society* 2008, 130, 12616.
27. F. J. Garcia-Vidal, J. B. Pendry, *Physical Review Letters* 1996, 77, 1163.
28. Z. Liu, S. Tabakman, S. Sherlock, X. L. Li, Z. Chen, K. L. Jiang, S. S. Fan, H. J. Dai, *Nano Research* 2010, 3, 222.
29. Z. Liu, S. Tabakman, K. Welsher, H. J. Dai, *Nano Research* 2009, 2, 85.
30. Z. A. Liu, X. L. Li, S. M. Tabakman, K. L. Jiang, S. S. Fan, H. J. Dai, *Journal of the American Chemical Society* 2008, 130, 13540.
31. Kindt, T. J., Goldsby, R. A., Osborne, B. A. & Kuby, J. *Kuby immunology.* 6th edn, (W.H. Freeman, 2007).
32. Oppenheim, J. J., Rossio, J. L. & Gearing, A. J. H. *Clinical applications of cytokines: role in pathogenesis, diagnosis, and therapy.* (Oxford University Press, 1993).
33. Lequin, R. M. Enzyme Immunoassay (EIA)/Enzyme-Linked Immunosorbent Assay (ELISA). *Clin Chem* 2005, 51, 2415-2418.
34. Diaz-Mitoma, F. et al. Expression of IL-10, IL-4 and interferon-gamma in unstimulated and mitogen-stimulated peripheral blood lymphocytes from HIV-seropositive patients. *Clin Exp Immunol* 1995, 102, 31-39.
35. Schweitzer, B. et al. Multiplexed protein profiling on microarrays by rolling-circle amplification. *Nat Biotechnol* 2002, 20, 359-365.
36. Tabakman, S. M. et al. Plasmonic substrates for multiplexed protein microarrays with femtomolar sensitivity and broad dynamic range. *Nat Commun* 2011, 2.
37. Fort, E. & Gresillon, S. Surface enhanced fluorescence. *J Phys D Appl Phys* 2008, 41.
38. Anger, P., Bharadwaj, P. & Novotny, L. Enhancement and quenching of single-molecule fluorescence. *Phys Rev Lett* 2006, 96.
39. Mertens, H., Koenderink, A. F. & Polman, A. Plasmon-enhanced luminescence near noble-metal nanospheres: Comparison of exact theory and an improved Gersten and Nitzan model. *Phys Rev B* 2007, 76.
40. Tabakman, S. M., Chen, Z., Casalongue, H. S., Wang, H. L. & Dai, H. J. A New Approach to Solution-Phase Gold Seeding for SERS Substrates. *Small* 2012, 7, 499-505.
41. Hong, G. S. et al. Metal-Enhanced Fluorescence of Carbon Nanotubes. *J Am Chem Soc* 132, 15920-15923 (2010).
42. Hong, G. S. et al. Near-Infrared-Fluorescence-Enhanced Molecular Imaging of Live Cells on Gold Substrates. *Angew Chem Int Edit* 50, 4644-4648 (2011).

43. Hong, G. et al. Three-dimensional imaging of single nanotube molecule endocytosis on plasmonic substrates. *Nat Commun* 2012, 3, 700.
44. McInnes, I. B. & Schett, G. Cytokines in the pathogenesis of rheumatoid arthritis. *Nat Rev Immunol* 2007, 7, 429-442.
45. Szekanecz, Z. & Koch, A. E. Mechanisms of Disease: angiogenesis in inflammatory diseases. *Nat Clin Pract Rheum* 2007, 3, 635-643.
46. Church, L. D., Cook, G. P. & McDermott, M. F. Primer: inflammasomes and interleukin 1beta in inflammatory disorders. *Nat Clin Pract Rheumatol* 4, 34-42 (2008).
47. Cicuttini, F. M. et al. Serum Il-4, Il-10 and Il-6 Levels in Inflammatory Arthritis. *Rheumatol Int* 14, 201-206 (1995).
48. Tepper, R. I. et al. Il-4 Induces Allergic-Like Inflammatory Disease and Alters T-Cell Development in Transgenic Mice. *Cell* 62, 457-467 (1990).
49. Rivas, D. et al. Upregulated expression of IL-4 receptors and increased levels of IL-4 in rheumatoid arthritis patients. *J Autoimmun* 8, 587-600 (1995).
50. Fava, R. A. et al. Vascular permeability factor/endothelial growth factor (VPF/VEGF): accumulation and expression in human synovial fluids and rheumatoid synovial tissue. *J Exp Med* 180, 341-346 (1994).
51. Distler, J. H. et al. Dysbalance of angiogenic and angiostatic mediators in patients with mixed connective tissue disease. *Ann Rheum Dis* 70, 1197-1202 (2011).
52. Bodolay, E. et al. Serum cytokine levels and type 1 and type 2 intracellular T cell cytokine profiles in mixed connective tissue disease. *J Rheumatol* 29, 2136-2142 (2002).
53. McNearney, T. et al. Excitatory amino acids, TNF-alpha, and chemokine levels in synovial fluids of patients with active arthropathies. *Clin Exp Immunol* 137, 621-627 (2004).
54. Tsai, P. C., Chen, C. J., Lai, H. M. & Chang, S. J. Analysis of polymorphisms in the promoter region and protein levels of interleukin-6 gene among gout patients. *Clin Exp Rheumatol* 26, 841-847 (2008).
55. Hueber, W. et al. Blood autoantibody and cytokine profiles predict response to anti-tumor necrosis factor therapy in rheumatoid arthritis. *Arthritis Res Ther* 11, R76 (2009).
56. Bauer, J. W. et al. Elevated serum levels of interferon-regulated chemokines are biomarkers for active human systemic lupus erythematosus. *PLoS Med* 3, e491 (2006).
57. Bauer, J. W. et al. Interferon-Regulated Chemokines as Biomarkers of Systemic Lupus Erythematosus Disease Activity A Validation Study. *Arthritis Rheum-Us* 60, 3098-3107 (2009).
58. Axtell, R. C. et al. T helper type 1 and 17 cells determine efficacy of interferon-beta in multiple sclerosis and experimental encephalomyelitis. *Nat Med* 16, 406-412 (2010).

What is claimed is:

1. A microarray for enhancing near-IR fluorescence of a near-IR fluorescently labeled analyte, comprising:
   (a) a solid substrate;
   (b) a discontinuous gold film applied to said substrate, said discontinuous gold film having isolated island areas of irregular shapes from 2000 nm$^2$ to 30,000 nm$^2$ in area, as measured from a scanning electron microscope (SEM) image of said film, viewed from the top down, and said islands having heights from 30 to 100 nm, and said islands having shape-conformal edges to form gaps between said islands of 10 to 60 nm extending along said edges and said film having a plasmonic resonance peak from 525 nm to 1400 nm; and
   (c) an array of biological molecule capture agents that specifically bind near-IR fluorescently labelled analytes in a sample, said capture agents coupled to the discontinuous gold film at discrete locations.

2. The microarray of claim 1, wherein the isolated island areas are between 10,000 nm$^2$ and 25,000 nm$^2$ in area.

3. The microarray of claim 1, wherein the isolated island areas are selected from the group consisting of (a) separated gold portions of a solution phase deposition; (b) separated gold islands etched on the film; (c) discrete gold particles assembled on the substrate; (d) gold nanorods assembled on the substrate; and (e) gold nanoplates assembled on the substrate.

4. The microarray of claim 1, further comprising a self-assembled monolayer between the discontinuous gold film and the biological molecule capture agents.

5. The microarray of claim 4, further comprising a branched polyethylene glycol (PEG) layer between the self-assembled monolayer and the biological molecule capture agents.

6. The microarray of claim 1, further comprising an avidin or streptavidin layer between the discontinuous gold film and the biological molecule capture agents.

7. The microarray of claim 1, wherein the biological molecule capture agents are one of proteins, peptides, antigens, antibodies, nucleic acids, polysaccharides, carbohydrates, or biomolecules in whole cells.

8. The microarray of claim 7, wherein the biological molecule capture agents are proteins that are cytokines.

9. The microarray of claim 1, further comprising, at the discrete locations, a self-assembled monolayer on the discontinuous gold film, a hydrophilic polymer linked to a self-assembled monolayer on the discontinuous gold film, wherein the biological molecule capture agents are linked to the hydrophilic polymer.

10. The microarray of claim 1, wherein the array of biological molecule capture agents is an array of different species of biological molecule capture agents.

11. The microarray of claim 10, wherein the biological molecule capture agents are different specific proteins, different cytokines, different DNA sequences, or antibodies of different specificities.

12. The microarray of claim 1, wherein the substrate is selected from glass, polymeric, quartz, silicon, or silicon dioxide.

13. The microarray of claim 12, wherein the substrate is polymeric and is selected from polyvinyl chloride (PVC) or polydimethyl siloxane (PDMS).

14. The microarray of claim 12, wherein the substrate is glass.

15. The microarray of claim 1, wherein the heights of said isolated island areas are measured from a scanning electron microscope (SEM) image viewed from the side of said microarray.

16. The microarray of claim 1, wherein the said isolated island areas appear two-dimensional from said top down scanning electron microscope (SEM) image of said film.

17. The microarray of claim 1, wherein the plasmonic resonance peak is in the range of 575 nm to 610 nm.

18. The microarray of claim 1, wherein said gaps of from 10 to 60 nm are measured from a scanning electron microscope (SEM) image of said film viewed from the top down.

* * * * *